United States Patent
Pennell et al.

(10) Patent No.: US 10,876,129 B2
(45) Date of Patent: Dec. 29, 2020

(54) METHODS AND MATERIALS FOR HIGH THROUGHPUT TESTING OF MUTAGENIZED ALLELE COMBINATIONS

(71) Applicant: Ceres, Inc., Thousand Oaks, CA (US)

(72) Inventors: Roger I. Pennell, Thousand Oaks, CA (US); Richard Hamilton, Thousand Oaks, CA (US); Delin Liang, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 4 days.

(21) Appl. No.: 16/077,024

(22) PCT Filed: Feb. 8, 2017

(86) PCT No.: PCT/US2017/016908
§ 371 (c)(1),
(2) Date: Aug. 9, 2018

(87) PCT Pub. No.: WO2017/139309
PCT Pub. Date: Aug. 17, 2017

(65) Prior Publication Data
US 2019/0032071 A1 Jan. 31, 2019

Related U.S. Application Data

(60) Provisional application No. 62/294,539, filed on Feb. 12, 2016.

(51) Int. Cl.
*C12N 15/82* (2006.01)
*A01H 1/06* (2006.01)
*A01H 6/46* (2018.01)

(52) U.S. Cl.
CPC ............ *C12N 15/8247* (2013.01); *A01H 1/06* (2013.01); *A01H 6/4636* (2018.05); *A01H 6/4666* (2018.05); *A01H 6/4678* (2018.05); *A01H 6/4684* (2018.05); *C12N 15/8213* (2013.01); *C12N 15/8271* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,906,616 B2 | 12/2014 | Zhang et al. |
| 8,993,233 B2 | 3/2015 | Zhang et al. |
| 8,999,641 B2 | 4/2015 | Zhang et al. |
| 9,115,348 B2 | 8/2015 | Haurwitz et al. |
| 9,688,971 B2 | 6/2017 | Doudna et al. |
| 9,745,610 B2 | 8/2017 | Doudna et al. |
| 10,087,431 B2 | 10/2018 | Wiedenheft et al. |
| 2014/0068797 A1 | 3/2014 | Doudna et al. |
| 2014/0315985 A1 | 10/2014 | May et al. |
| 2016/0017365 A1* | 1/2016 | Cigan ............... C07K 14/415 800/260 |

FOREIGN PATENT DOCUMENTS

| | | | |
|---|---|---|---|
| WO | WO 2014144155 A1 | 9/2014 | |
| WO | WO-2015171894 A1 * | 11/2015 | ......... C12N 15/8213 |
| WO | WO 2015171894 A1 | 11/2015 | |

OTHER PUBLICATIONS

Bateman, et al., "Pfam 3.1: 1313 Multiple Alignments and Profile HMMs Match the Majority of Proteins," Nucleic Acids Research 27(1):260-262 (1999).
Bortesi and Fischer, "The CRISPR/Cas9 System for Plant Genome Editing and Beyond," Biotechnology Advances 33(1):41-52 (2015).
Feng, et al., "Efficient Targeted Genome Modification in Maize Using CRISPR/Cas9 System," Journal of Genetics and Genomics 43(1):37-43 (2016).
International Preliminary Report on Patentability regarding International Application No. PCT/US2017/016908, dated Aug. 23, 2017.
International Search Report and Written Opinion regarding International Application No. PCT/US2017/016908, dated Jun. 28, 2017.
Ran, et al., "Genome Engineering Using the CRISPR-Cas9 System," Nature Protocols 8(11):2281-2308 (2013).
Schaeffer and Nakata, "CRISPRCas9-mediated Genome Editing and Gene Replacement in Plants: Transitioning From Lab to Field," Plant Science 240:130-142 (2015).
Smith, "Embryo Culture of a Tomato Species Hybrid," Proceedings of the American Society for Horticultural Science 44:413-16 (1944).
Sonnhammer, et al., "Pfam: A Comprehensive Database of Protein Domain Families Based on Seed Alignments," Proteins 28(3):405-420 (1997).
Sonnhammer, et al., "Pfam: Multiple Sequence Alignments and HMM-profiles of Protein Domains," Nucleic Acids Research 26(1):320-322 (1998).
Svitashev, et al., "Targeted Mutagenesis, Precise Gene Editing, and Site-Specific Gene Insertion in Maize Using Cas9 and Guide RNA," Plant Physiology 169(2):931-945 (2015).
Woo, et al., "DNA-free Genome Editing in Plants With Preassembled CRISPR-Cas9 Ribonucleoproteins," Nature Biotechnology 33(11):1162-1164 (2015).
Zetscje, et al., "Cpf1 Is a Single RNA-Guided Endonuclease of a Class 2 CRISPR-Cas System," Cell 163(3):759-771 (2015).

* cited by examiner

*Primary Examiner* — Brent T Page
(74) *Attorney, Agent, or Firm* — Dentons US LLP

(57) ABSTRACT

High throughput methods are described for identifying combinations of mutations that can be used to improve a phenotypic feature in an organism. Large populations of organisms (e.g., plants) containing different combinations of mutations can be assessed using the methods.

23 Claims, 1 Drawing Sheet
Specification includes a Sequence Listing.

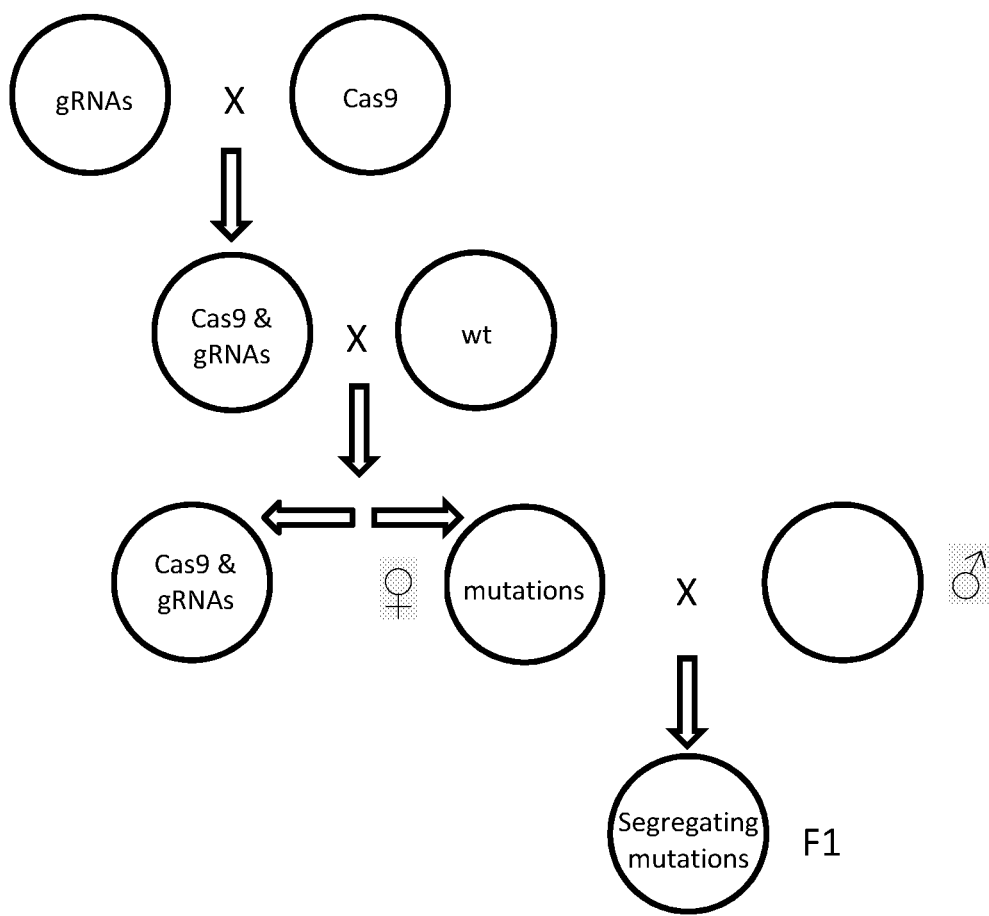

SEQUENCE LISTING

<160> NUMBER OF SEQ ID NOS: 39

<210> SEQ ID NO 1
<211> LENGTH: 4395
<212> TYPE: DNA
<213> ORGANISM: Streptococcus pyogenes

<400> SEQUENCE: 1
atgggcggta ggcgtgtacg gtgggaggtc tatataagca gagctcgttt agtgaaccgt    60

```
cagaattttg taatacgact cactataggg cggccgggaa ttcgtcgact ggaaccggta    120
ccgaggagat ctgccgccgc gatcgccatg gataagaaat actcaatagg actggatatt    180
ggcacaaata gcgtcggatg ggctgtgatc actgatgaat ataaggttcc ttctaaaaag    240
ttcaaggttc tgggaaatac agaccgccac agtatcaaaa aaaatcttat aggggctctt    300
ctgtttgaca gtggagagac agccgaagct actagactca aacggacagc taggagaagg    360
tatacaagac ggaagaatag gatttgttat ctccaggaga ttttttcaaa tgagatggcc    420
aaagtggatg atagtttctt tcatagactt gaagagtctt ttttggtgga agaagacaag    480
aagcatgaaa gacatcctat ttttggaaat atagtggatg aagttgctta tcacgagaaa    540
tatccaacta tctatcatct gagaaaaaaa ttggtggatt ctactgataa agccgatttg    600
cgcctgatct atttggccct ggcccacatg attaagttta gaggtcattt tttgattgag    660
ggcgatctga atcctgataa tagtgatgtg acaaactgt ttatccagtt ggtgcaaacc     720
tacaatcaac tgtttgaaga aaacccctatt aacgcaagtg gagtggatgc taaagccatt    780 cttctctgcaa gattgagtaa atcaagaaga ctggaaaatc tcattgctca gctccccggt    840
gagaagaaaa atggcctgtt tgggaatctc attgcttttgt cattgggttt gaccccctaat    900 tttaaatcaa attttgattt ggcagaagat gctaaactcc agctttcaaa agatacttac    960
gatgatgatc tggataatct gttggctcaa attggggatc aatatgctga tttgtttttg    1020
gcagctaaga atctgtcaga tgctattctg ctttcagaca tcctgagagt gaatactgaa    1080
ataactaagg ctcccctgtc agcttcaatg attaaacgct acgatgaaca tcatcaagac    1140
ttgactcttc tgaaagccct ggttagacaa caacttccag aaaagtataa agaaatcttt    1200
tttgatcaat caaaaaacgg atatgcaggt tatattgatg gcggcgcaag ccaagaagaa    1260
ttttataaat ttatcaaacc aattctggaa aaaatggatg gtactgagga actgttggtg    1320
aaactgaata gagaagattt gctgcgcaag caacggacct ttgacaacgg ctctattccc    1380
catcaaattc acttgggtga gctgcatgct atttttgagaa acaagaaga cttttatcca    1440 tttctgaaag acaatagaga gaagattgaa aaaatcttga cttttaggat tccttattat    1500
gttggtccat tggccagagg caatagtagg tttgcatgga tgactcggaa gtctgaagaa    1560
acaattaccc catggaattt tgaagaagtt gtcgataaag gtgcttcagc tcaatcattt    1620
attgaacgca tgacaaactt tgataaaaat cttccaaatg aaaaagtgct gccaaaacat    1680
agtttgcttt atgagtattt taccgtttat aacgaattga caaaggtcaa atatgttact    1740
gaaggaatga gaaaaccagc atttctttca ggtgaacaga gaaagccat tgttgatctg    1800 ctcttcaaaa caaataggaa agtgaccgtt aagcaactga agaagatta tttcaaaaaa    1860 atagaatgtt ttgatagtgt tgaaatttca ggagttgaag atagatttaa tgcttcactg    1920
ggtacatacc atgatttgct gaaaattatt aaagataaag attttttgga taatgaagaa    1980
aatgaagaca tcctggagga tattgttctg acattgaccc tgtttgaaga tagggagatg    2040
attgaggaaa gacttaaaac atacgctcac ctctttgatg ataaggtgat gaaacagctt    2100
aaaagacgca gatatactgg ttggggaagg ttgtccagaa aattgattaa tggtattagg    2160
gataagcaat ctggcaaaac aatactggat tttttgaaat cagatggttt tgccaatcgc    2220
aattttatgc agctcatcca tgatgatagt ttgacattta agaagacat ccaaaaagca     2280 caagtgtctg acaaggcga tagtctgcat gaacatattg caaatctggc tggtagccct    2340
gctattaaaa aaggtattct ccagactgtg aaagttgttg atgaattggt caaagtgatg    2400
gggcggcata agccagaaaa tatcgttatt gaaatggcaa gagaaaatca gacaactcaa    2460
```

-continued

```
aagggccaga aaaattccag agagaggatg aaaagaatcg aagaaggtat caaagaactg    2520
ggaagtcaga ttcttaaaga gcatcctgtt gaaaatactc aattgcaaaa tgaaaagctc    2580
tatctctatt atctccaaaa tggaagagat atgtatgtgg accaagaact ggatattaac    2640
aggctgagtg attatgatgt cgatcacatt gttccacaaa gtttccttaa agacgattca    2700
atagacaata aggtcctgac caggtctgat aaaaatagag gtaaatccga taacgttcca    2760
agtgaagaag tggtcaaaaa gatgaaaaac tattggagac aacttctgaa cgccaagctg    2820
atcactcaaa ggaagtttga taatctgacc aaagctgaaa gaggaggttt gagtgaactt    2880
gataaagctg gttttatcaa cgccaattg gttgaaactc gccaaatcac taagcatgtg    2940
gcacaaattt tggatagtcg catgaatact aaatacgatg aaaatgataa acttattaga    3000
gaggttaaag tgattaccct gaaatctaaa ctggtttctg acttcagaaa agatttccaa    3060
ttctataaag tgagagagat taacaattac catcatgccc atgatgccta tctgaatgcc    3120
gtcgttggaa ctgctttgat taagaaatat ccaaaacttg aaagcgagtt tgtctatggt    3180
gattataaag tttatgatgt taggaaaatg attgctaagt ctgagcaaga ataggcaaa    3240 gcaaccgcaa agtatttctt ttactctaat atcatgaact tcttcaaaac agaaattaca    3300
cttgcaaatg gagagattcg caaacgccct ctgatcgaaa ctaatgggga aactggagaa    3360
attgtctggg ataaagggag agattttgcc acagtgcgca aagtgttgtc catgccccaa    3420
gtcaatatcg tcaagaaaac agaagtgcag acaggcggat tctctaagga gtcaattctg    3480
ccaaaaagaa attccgacaa gctgattgct aggaaaaaag actgggaccc aaaaaaatat    3540
ggtggttttg atagtccaac cgtggcttat tcagtcctgg tggttgctaa ggtggaaaaa    3600
gggaaatcca agaagctgaa atccgttaaa gagctgctgg ggatcacaat tatgaaaga    3660 agttcctttg aaaaaaatcc cattgacttt ctggaagcta aggatataa ggaagttaaa    3720 aaagacctga tcattaaact gcctaaatat agtcttttg agctggaaaa cggtaggaaa    3780
cggatgctgg ctagtgccgg agaactgcaa aaggaaatg agctggctct gccaagcaaa    3840
tatgtgaatt ttctgtatct ggctagtcat tatgaaaagt tgaagggtag tccagaagat    3900
aacgaacaaa acaattgtt tgtggagcag cataagcatt atctggatga gattattgag    3960
caaatcagtg aatttttctaa gagagttatt ctggcagatg ccaatctgga taaagttctt    4020
agtgcatata caaacatag agacaaacca ataagagaac aagcagaaaa tatcattcat    4080
ctgtttacct tgaccaatct ggagcaccc gctgctttta aatactttga tacaacaatt    4140
gataggaaaa gatataccct acaaaagaa gttctggatg ccactcttat ccatcaatcc    4200
atcactggtc tttatgaaac acgcattgat ttgagtcagc tgggaggtga ccccaagaaa    4260
aaacgcaagg tggaagatcc taagaaaaag cggaaagtgg acacgcgtac gcggccgctc    4320
gagcagaaac tcatctcaga agaggatctg gcagcaaatg atatcctgga ttacaaggat    4380
gacgacgata aggtt                                                    4395
```

```
<210> SEQ ID NO 2
<211> LENGTH: 1465
<212> TYPE: PRT
<213> ORGANISM: Streptococcus pyogenes

<400> SEQUENCE: 2

Met Gly Gly Arg Arg Val Arg Trp Glu Val Tyr Ile Ser Arg Ala Arg
1               5                   10                  15

Leu Val Asn Arg Gln Asn Phe Val Ile Arg Leu Thr Ile Gly Arg Pro
```

-continued

```
                     20                  25                  30
Gly Ile Arg Arg Leu Glu Pro Val Pro Arg Ser Ala Ala Ile
                 35                  40                  45

Ala Met Asp Lys Lys Tyr Ser Ile Gly Leu Asp Ile Gly Thr Asn Ser
 50                  55                  60

Val Gly Trp Ala Val Ile Thr Asp Glu Tyr Lys Val Pro Ser Lys Lys
 65                  70                  75                  80

Phe Lys Val Leu Gly Asn Thr Asp Arg His Ser Ile Lys Lys Asn Leu
                 85                  90                  95

Ile Gly Ala Leu Leu Phe Asp Ser Gly Glu Thr Ala Glu Ala Thr Arg
                100                 105                 110

Leu Lys Arg Thr Ala Arg Arg Tyr Thr Arg Arg Lys Asn Arg Ile
                115                 120                 125

Cys Tyr Leu Gln Glu Ile Phe Ser Asn Glu Met Ala Lys Val Asp Asp
                130                 135                 140

Ser Phe Phe His Arg Leu Glu Glu Ser Phe Leu Val Glu Glu Asp Lys
145                 150                 155                 160

Lys His Glu Arg His Pro Ile Phe Gly Asn Ile Val Asp Glu Val Ala
                165                 170                 175

Tyr His Glu Lys Tyr Pro Thr Ile Tyr His Leu Arg Lys Lys Leu Val
                180                 185                 190

Asp Ser Thr Asp Lys Ala Asp Leu Arg Leu Ile Tyr Leu Ala Leu Ala
                195                 200                 205

His Met Ile Lys Phe Arg Gly His Phe Leu Ile Glu Gly Asp Leu Asn
                210                 215                 220

Pro Asp Asn Ser Asp Val Asp Lys Leu Phe Ile Gln Leu Val Gln Thr
225                 230                 235                 240

Tyr Asn Gln Leu Phe Glu Glu Asn Pro Ile Asn Ala Ser Gly Val Asp
                245                 250                 255

Ala Lys Ala Ile Leu Ser Ala Arg Leu Ser Lys Ser Arg Arg Leu Glu
                260                 265                 270

Asn Leu Ile Ala Gln Leu Pro Gly Glu Lys Lys Asn Gly Leu Phe Gly
                275                 280                 285

Asn Leu Ile Ala Leu Ser Leu Gly Leu Thr Pro Asn Phe Lys Ser Asn
                290                 295                 300

Phe Asp Leu Ala Glu Asp Ala Lys Leu Gln Leu Ser Lys Asp Thr Tyr
305                 310                 315                 320

Asp Asp Asp Leu Asp Asn Leu Leu Ala Gln Ile Gly Asp Gln Tyr Ala
                325                 330                 335

Asp Leu Phe Leu Ala Ala Lys Asn Leu Ser Asp Ala Ile Leu Leu Ser
                340                 345                 350

Asp Ile Leu Arg Val Asn Thr Glu Ile Thr Lys Ala Pro Leu Ser Ala
                355                 360                 365

Ser Met Ile Lys Arg Tyr Asp Glu His His Gln Asp Leu Thr Leu Leu
                370                 375                 380

Lys Ala Leu Val Arg Gln Gln Leu Pro Glu Lys Tyr Lys Glu Ile Phe
385                 390                 395                 400

Phe Asp Gln Ser Lys Asn Gly Tyr Ala Gly Tyr Ile Asp Gly Gly Ala
                405                 410                 415

Ser Gln Glu Glu Phe Tyr Lys Phe Ile Lys Pro Ile Leu Glu Lys Met
                420                 425                 430

Asp Gly Thr Glu Glu Leu Leu Val Lys Leu Asn Arg Glu Asp Leu Leu
                435                 440                 445
```

```
Arg Lys Gln Arg Thr Phe Asp Asn Gly Ser Ile Pro His Gln Ile His
        450                 455                 460

Leu Gly Glu Leu His Ala Ile Leu Arg Arg Gln Glu Asp Phe Tyr Pro
465                 470                 475                 480

Phe Leu Lys Asp Asn Arg Glu Lys Ile Glu Lys Ile Leu Thr Phe Arg
                485                 490                 495

Ile Pro Tyr Tyr Val Gly Pro Leu Ala Arg Gly Asn Ser Arg Phe Ala
                500                 505                 510

Trp Met Thr Arg Lys Ser Glu Glu Thr Ile Thr Pro Trp Asn Phe Glu
            515                 520                 525

Glu Val Val Asp Lys Gly Ala Ser Ala Gln Ser Phe Ile Glu Arg Met
530                 535                 540

Thr Asn Phe Asp Lys Asn Leu Pro Asn Glu Lys Val Leu Pro Lys His
545                 550                 555                 560

Ser Leu Leu Tyr Glu Tyr Phe Thr Val Tyr Asn Glu Leu Thr Lys Val
                565                 570                 575

Lys Tyr Val Thr Glu Gly Met Arg Lys Pro Ala Phe Leu Ser Gly Glu
                580                 585                 590

Gln Lys Lys Ala Ile Val Asp Leu Leu Phe Lys Thr Asn Arg Lys Val
            595                 600                 605

Thr Val Lys Gln Leu Lys Glu Asp Tyr Phe Lys Lys Ile Glu Cys Phe
        610                 615                 620

Asp Ser Val Glu Ile Ser Gly Val Glu Asp Arg Phe Asn Ala Ser Leu
625                 630                 635                 640

Gly Thr Tyr His Asp Leu Leu Lys Ile Ile Lys Asp Lys Asp Phe Leu
                645                 650                 655

Asp Asn Glu Glu Asn Glu Asp Ile Leu Glu Asp Ile Val Leu Thr Leu
                660                 665                 670

Thr Leu Phe Glu Asp Arg Glu Met Ile Glu Glu Arg Leu Lys Thr Tyr
            675                 680                 685

Ala His Leu Phe Asp Asp Lys Val Met Lys Gln Leu Lys Arg Arg Arg
690                 695                 700

Tyr Thr Gly Trp Gly Arg Leu Ser Arg Lys Leu Ile Asn Gly Ile Arg
705                 710                 715                 720

Asp Lys Gln Ser Gly Lys Thr Ile Leu Asp Phe Leu Lys Ser Asp Gly
                725                 730                 735

Phe Ala Asn Arg Asn Phe Met Gln Leu Ile His Asp Asp Ser Leu Thr
                740                 745                 750

Phe Lys Glu Asp Ile Gln Lys Ala Gln Val Ser Gly Gln Gly Asp Ser
            755                 760                 765

Leu His Glu His Ile Ala Asn Leu Ala Gly Ser Pro Ala Ile Lys Lys
770                 775                 780

Gly Ile Leu Gln Thr Val Lys Val Val Asp Glu Leu Val Lys Val Met
785                 790                 795                 800

Gly Arg His Lys Pro Glu Asn Ile Val Ile Glu Met Ala Arg Glu Asn
                805                 810                 815

Gln Thr Thr Gln Lys Gly Gln Lys Asn Ser Arg Glu Arg Met Lys Arg
            820                 825                 830

Ile Glu Glu Gly Ile Lys Glu Leu Gly Ser Gln Ile Leu Lys Glu His
                835                 840                 845

Pro Val Glu Asn Thr Gln Leu Gln Asn Glu Lys Leu Tyr Leu Tyr Tyr
850                 855                 860
```

Leu Gln Asn Gly Arg Asp Met Tyr Val Asp Gln Glu Leu Asp Ile Asn
865                 870                 875                 880

Arg Leu Ser Asp Tyr Asp Val Asp His Ile Val Pro Gln Ser Phe Leu
            885                 890                 895

Lys Asp Asp Ser Ile Asp Asn Lys Val Leu Thr Arg Ser Asp Lys Asn
                900                 905                 910

Arg Gly Lys Ser Asp Asn Val Pro Ser Glu Glu Val Val Lys Lys Met
        915                 920                 925

Lys Asn Tyr Trp Arg Gln Leu Leu Asn Ala Lys Leu Ile Thr Gln Arg
930                 935                 940

Lys Phe Asp Asn Leu Thr Lys Ala Glu Arg Gly Gly Leu Ser Glu Leu
945                 950                 955                 960

Asp Lys Ala Gly Phe Ile Lys Arg Gln Leu Val Glu Thr Arg Gln Ile
                965                 970                 975

Thr Lys His Val Ala Gln Ile Leu Asp Ser Arg Met Asn Thr Lys Tyr
            980                 985                 990

Asp Glu Asn Asp Lys Leu Ile Arg Glu Val Lys Val Ile Thr Leu Lys
            995                1000                1005

Ser Lys Leu Val Ser Asp Phe Arg Lys Asp Phe Gln Phe Tyr Lys
    1010                1015                1020

Val Arg Glu Ile Asn Asn Tyr His His Ala His Asp Ala Tyr Leu
    1025                1030                1035

Asn Ala Val Val Gly Thr Ala Leu Ile Lys Lys Tyr Pro Lys Leu
    1040                1045                1050

Glu Ser Glu Phe Val Tyr Gly Asp Tyr Lys Val Tyr Asp Val Arg
    1055                1060                1065

Lys Met Ile Ala Lys Ser Glu Gln Glu Ile Gly Lys Ala Thr Ala
    1070                1075                1080

Lys Tyr Phe Phe Tyr Ser Asn Ile Met Asn Phe Phe Lys Thr Glu
    1085                1090                1095

Ile Thr Leu Ala Asn Gly Glu Ile Arg Lys Arg Pro Leu Ile Glu
    1100                1105                1110

Thr Asn Gly Glu Thr Gly Glu Ile Val Trp Asp Lys Gly Arg Asp
    1115                1120                1125

Phe Ala Thr Val Arg Lys Val Leu Ser Met Pro Gln Val Asn Ile
    1130                1135                1140

Val Lys Lys Thr Glu Val Gln Thr Gly Gly Phe Ser Lys Glu Ser
    1145                1150                1155

Ile Leu Pro Lys Arg Asn Ser Asp Lys Leu Ile Ala Arg Lys Lys
    1160                1165                1170

Asp Trp Asp Pro Lys Lys Tyr Gly Gly Phe Asp Ser Pro Thr Val
    1175                1180                1185

Ala Tyr Ser Val Leu Val Val Ala Lys Val Glu Lys Gly Lys Ser
    1190                1195                1200

Lys Lys Leu Lys Ser Val Lys Glu Leu Leu Gly Ile Thr Ile Met
    1205                1210                1215

Glu Arg Ser Ser Phe Glu Lys Asn Pro Ile Asp Phe Leu Glu Ala
    1220                1225                1230

Lys Gly Tyr Lys Glu Val Lys Lys Asp Leu Ile Ile Lys Leu Pro
    1235                1240                1245

Lys Tyr Ser Leu Phe Glu Leu Glu Asn Gly Arg Lys Arg Met Leu
    1250                1255                1260

Ala Ser Ala Gly Glu Leu Gln Lys Gly Asn Glu Leu Ala Leu Pro

```
                        1265                 1270                1275
Ser Lys Tyr Val Asn Phe Leu Tyr Leu Ala Ser His Tyr Glu Lys
            1280                1285                1290
Leu Lys Gly Ser Pro Glu Asp Asn Glu Gln Lys Gln Leu Phe Val
            1295                1300                1305
Glu Gln His Lys His Tyr Leu Asp Glu Ile Ile Glu Gln Ile Ser
            1310                1315                1320
Glu Phe Ser Lys Arg Val Ile Leu Ala Asp Ala Asn Leu Asp Lys
            1325                1330                1335
Val Leu Ser Ala Tyr Asn Lys His Arg Asp Lys Pro Ile Arg Glu
            1340                1345                1350
Gln Ala Glu Asn Ile Ile His Leu Phe Thr Leu Thr Asn Leu Gly
            1355                1360                1365
Ala Pro Ala Ala Phe Lys Tyr Phe Asp Thr Thr Ile Asp Arg Lys
            1370                1375                1380
Arg Tyr Thr Ser Thr Lys Glu Val Leu Asp Ala Thr Leu Ile His
            1385                1390                1395
Gln Ser Ile Thr Gly Leu Tyr Glu Thr Arg Ile Asp Leu Ser Gln
            1400                1405                1410
Leu Gly Gly Asp Pro Lys Lys Lys Arg Lys Val Glu Asp Pro Lys
            1415                1420                1425
Lys Lys Arg Lys Val Asp Thr Arg Thr Arg Pro Leu Glu Gln Lys
            1430                1435                1440
Leu Ile Ser Glu Glu Asp Leu Ala Ala Asn Asp Ile Leu Asp Tyr
            1445                1450                1455
Lys Asp Asp Asp Asp Lys Val
            1460                1465

<210> SEQ ID NO 3
<211> LENGTH: 1000
<212> TYPE: DNA
<213> ORGANISM: Zea mays

<400> SEQUENCE: 3
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga ggggcatca     480 aagatctggc tgtgttttcca gctgttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaatgct      660 attcgaattt ctactagcag taagtcgtgt ttagaaatta tttttttata tacctttttt     720
ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
```

| | |
|---|---|
| ggtggagcaa agcgctgggt aatacgcaaa cgttttgtcc caccttgact aatcacaaga | 960 |
| gtggagcgta ccttataaac cgagccgcaa gcaccgaatt | 1000 |

<210> SEQ ID NO 4
<211> LENGTH: 381
<212> TYPE: DNA
<213> ORGANISM: Sorghum bicolor

<400> SEQUENCE: 4

| | |
|---|---|
| gcttgctcaa cttagcactt agcagtaaca ttttagtaca ctgattgcga ttgttagcag | 60 |
| tactccgggt tagcacctag cagtactccg ggagctctgt gaactgtgaa gagtgaacta | 120 |
| caaccatcta ggaatcagct gagcttatta ttatcttacc ttcttttta cctcaggtg | 180 |
| aggcattagc attaagccac caacaggggt aaagctaatg cagcatcgat gggctcgacc | 240 |
| tgaactctga acttctgaag cccacacata caacaagtgg cccagtgcgc aatatgctgg | 300 |
| ccactcccac cgattagtac caccctcggct cctcaaatgc gtagaagcta acttaaaagc | 360 |
| tcagttctcc agccattcag c | 381 |

<210> SEQ ID NO 5
<211> LENGTH: 2000
<212> TYPE: DNA
<213> ORGANISM: Zea mays

<400> SEQUENCE: 5

| | |
|---|---|
| cgccgagcaa gtcaatcgcc ccatcatgcg gacttgctcg gcaaatgggc tagagagagg | 60 |
| tttatgggcc tcgccttggg taccctgttc ccggtacccg acaatgacct tcctcggatg | 120 |
| ctgataggtc aattaaagaa acaacaatgg atatatatgg ataggtatag aggtgtaagg | 180 |
| ctatctctag aacgttgcct attcttatac ccatattcaa actttattga taaaatgttg | 240 |
| gacaggtctg gtgcccttgg aacaagtgtt gtttccattc tccagagtgg actacttctt | 300 |
| gcgctgattt gtttggtgag ttaccgaagg agatttaggg gaagaaaaac agggcactta | 360 |
| taagtgatat attgtttatc tcagatgtat tgatcacttc tctggtattg gtgcaatgta | 420 |
| ttggggtacc gatcactgag taatcacgca atgtattggg gtactaaatc ctctctggta | 480 |
| tcgattattc atgcaatgta ttgacgattt taataagtga atcgccaatg tatatgatat | 540 |
| ttccactggc ggtgtactta atacagccgc cagtgtatat acatcatttc cactgacggt | 600 |
| tcagttaagt gaaccgcaag tgtatatgac atttccactg gcggtgtact ttatagaacc | 660 |
| gccagtgtat atacatcctt tacactgacg gttcagttaa gtgaaccacc agtgtatatg | 720 |
| atatttccac tggcggtgta cttaatacag ctgccagtgt atatacatcc tttatactga | 780 |
| cggttcagtt aagtgaaccg acagtgtata tgatatttcc actgccggtg tacttaatac | 840 |
| agctgccagt gtatatacat cctttatact gacggttcag ttaagtgaac cgccagtata | 900 |
| tattatattt ccactggcgg tttacttaat aaaaccgcaa gtgtaaatac atcatttaca | 960 |
| ctgacagttt tgttaagtga accaccagcg tatatatatt tacactgccg gttcgttaag | 1020 |
| acgggcccgt ctgttttttt cactggcgtg ctgtaactga aaccgccatt ataaatttct | 1080 |
| acgtgccgcc accttagagc tcttttctac tagtgttaac ttcttttctt gtagaccatt | 1140 |
| tggaaaacag gaaacaacgc ggtactgtat tcaacaacag atggttgtcc acacctatga | 1200 |
| caatcatggc gtcaatgcag tagtaagttt gtcgtttttg tgtgtgtgtg tttattagcc | 1260 |
| gtttctttgt ttttttcttt ctgttgagct ccaactttat gaaacgtcgt aagctggtaa | 1320 |
| ttatgaaatg taaggatttg gagagagaaa aaaaacggga gggaaaacca tgcatgctgc | 1380 |

```
tgacgcgacg gccggacgca gacgcaacaa tgccccggt gcggcgttgt cgagcagcca    1440
ctgcaccacc ccacgcatca cctgcagtaa tctagcgacg ggttttcctt atttatttat    1500
ttatttattt attttctcc tctccctccc tccctcagat ttgttttcgt tttcattaat    1560
cgttattacc agcaattaat taactttatc tattgattta ccaaaccgca ataaagaata    1620
tatatattct tttattaagg tccagtaata agcagcacag aagcgcaggt gcagcagcag    1680
cagcgtcagc gcccgaggcg cgcacgagag aaacagaggc tgacgaggtg gggcccgtgc    1740
gggccttgac caatcggagt tcgacaacag cctggccacc cacaaacaca cactccttcg    1800
cctcgcgccg gccgtcgtcg cctccctcca ccgaacgatc cctcctcctc ctcctcctcc    1860
tcctcctcgc atcccacccc accccacctt ctccttaaag ctacctgcct acccggcggt    1920
tgccgccgcc gcaatcgatc gaccggaaga gaaagagcag ctagctagct agcagatcgg    1980
agcacggcaa caaggcgatg                                                2000

<210> SEQ ID NO 6
<211> LENGTH: 1608
<212> TYPE: DNA
<213> ORGANISM: Oryza sativa

<400> SEQUENCE: 6
atggggatgg aggtggcggc ggcgcggctg ggggctctgt acacgacctc cgactacgcg      60
tcggtggtgt ccatcaacct gttcgtcgcg ctgctctgcg cctgcatcgt cctcggccac     120
ctcctcgagg agaatcgctg ggtcaatgag tccatcaccg cgctcatcat cgggctctgc     180
accggcgtgg tgatcttgct gatgaccaaa gggaagagct cgcacttatt cgtcttcagt     240
gaggatctct tcttcatcta cctcctccct ccgatcatct tcaatgcagg ttttcaggta     300
aagaaaaagc aattcttccg gaatttcatg acgatcacat tatttggagc cgtcgggaca     360
atgatatcct ttttcacaat atctattgct gccattgcaa tattcagcag aatgaacatt     420
ggaacgctgg atgtaggaga ttttcttgca attggagcca tctttctgc gacagattct     480 gtctgcacat tgcaggtcct caatcaggat gagacaccct ttttgtacag tctggtattc     540
ggtgaaggtg ttgtgaacga tgctacatca attgtgcttt tcaacgcact acagaacttt     600
gatcttgtcc acatagatgc ggctgtcgtt ctgaaattct tggggaactt cttttattta     660
tttttgtcga gcaccttcct tggagtattt gctggattgc tcagtgcata cataatcaag     720
aagctataca ttggaaggca ttctactgac cgtgaggttg cccttatgat gctcatggct     780
tacctttcat atatgctggc tgagttgcta gatttgagcg gcattctcac cgtattcttc     840
tgtggtattg taatgtcaca ttacacttgg cataacgtca cagagagttc aagagttaca     900
acaaagcacg catttgcaac tctgtccttc attgctgaga ctttctcttt cctgtatgtt     960
gggatggatg cattggatat tgaaaaatgg gagtttgcca gtgacagacc tggcaaatcc    1020
attgggataa gctcaatttt gctaggattg gttctgattg gaagagctgc ttttgtattc    1080
ccgctgtcgt tcttgtcgaa cctaacaaag aaggcaccga atgaaaaaat aacctggaga    1140
cagcaagttg taatatggtg ggctgggctg atgagaggag ctgtgtcgat tgctcttgct    1200
tacaataagt ttacaagatc tggccatact cagctgcacg gcaatgcaat aatgatcacc    1260
agcaccatca ctgtcgttct ttttagcact atggtatttg ggatgatgac aaagccattg    1320
atcaggctgc tgctaccggc ctcaggccat cctgtcacct ctgagccttc atcaccaaag    1380
tccctgcatt ctcctctcct gacaagcatg caaggttctg acctcgagag tacaaccaac    1440
```

| | |
|---|---|
| attgtgaggc cttccagcct ccggatgctc ctcaccaagc cgacccacac tgtccactac | 1500 |
| tactggcgca agttcgacga cgcgctgatg cgaccgatgt ttggcgggcg cgggttcgtg | 1560 |
| cccttctccc ctggatcacc aaccgagcag agccatggag gaagatga | 1608 |

<210> SEQ ID NO 7
<211> LENGTH: 1503
<212> TYPE: DNA
<213> ORGANISM: Oryza sativa

<400> SEQUENCE: 7

| | |
|---|---|
| atgggtaaga aaggaaattg gttcagtgct gtcaagaaag tcttcagctc atccgatcca | 60 |
| gatgggaggg aagctaagat cgagaaggcg gacaagtcga gatccaggag gaaatggcca | 120 |
| tttggaaagt ctaagaagtc tgatccttgg acctcaacag tggcagtgcc tacctctaca | 180 |
| gcaccgcctc cacagccgcc accgccaccg ccaacacacc ctatccagcc acagcctgag | 240 |
| gagatcaaag atgtcaaggc tgttgaaact gacagtgaac agaacaagca tgcgtactct | 300 |
| gttgcacttg cctctgctgt tgctgcagaa gctgctgccg tcgctgccca ggccgctgct | 360 |
| gaggtggtcc gcctcacaac agccaccacg gctgtgccga atcgcctgt tagttcaaag | 420 |
| gatgagcttg ccgctatcaa gattcagact gccttcaggg gttatctggc aagaagagcg | 480 |
| ctgcgagcac ttagagggct agttagattg aagtcgctgg ttgatggaaa cgccgtcaaa | 540 |
| cgacaaactg cgcacacctt gcattgcaca caaaccatga ccagagttca aactcaaata | 600 |
| tactctagaa gggtgaagat ggaggaggaa aaacaggctc ttcaaaggca gctacaatta | 660 |
| aagcatcaga gggaacttga gaaaatgaag attgatgaag attgggatca tagccatcag | 720 |
| tccaaggagc aggttgagac cagcctaatg atgaaacaag aagctgcgct aaggcgggaa | 780 |
| agagctcttg cctatgcatt ttctcaccag tggaagaatt ctggccgaac tataacacct | 840 |
| accttcacgg atcaagggaa tcctaactgg ggatggagct ggatggaacg ctggatgaca | 900 |
| tcaaggccctt gggagagccg agtgatatca gataaggatc ctaaggacca ttattcaaca | 960 |
| aagaatccca gcactagcgc ttctcgtact tatgtacccc gcgcaatctc aatccagaga | 1020 |
| cctgcaacac caaacaagtc aagccgtcca ccaagtcggc aatcgccatc aactcccccg | 1080 |
| tcaagggtcc cctcagttac cggaaagatc agaccagcaa gtccacggga tagctggcta | 1140 |
| tataaggagg atgacttgag gagcatcaca agcatacgct ctgaacgccc aaggaggcag | 1200 |
| agcacaggtg gtgcctctgt tcgggatgat gcgagcctaa caagcacacc agctctcccc | 1260 |
| agctacatgc agtccacaga gtctgcaagg caaagtctc ggtaccgcag tctattgact | 1320 |
| gacaggtttg aggttcctga gagagtaccc ctggtccatt cttcaataaa gaagcgctta | 1380 |
| tccttcccag tcgcagacaa accaaatggt gagcatgcag ataagctgat ggaaagaggg | 1440 |
| aggcgtcatt cagaccctcc taaggtggat cctgcctcac tgaaggatgt tccggtttca | 1500 |
| taa | 1503 |

<210> SEQ ID NO 8
<211> LENGTH: 3447
<212> TYPE: DNA
<213> ORGANISM: Oryza sativa

<400> SEQUENCE: 8

| | |
|---|---|
| atggacaatc ccgaggcgga gcctgatgac gcggtgctct tcgtcggggt ctccctcgtc | 60 |
| ctcggcatcg cctcccgcca cctcctccgg ggcaccgcg tccctacac cgtcgccctc | 120 |
| ctcgtcctcg gcgtcgccct cggatcgctc gaatttggca caaaacatgg cctgggcaaa | 180 |

```
ctcggagccg gcattcgtat ctgggctaac attaatcctg atcttcttct ggctgttttt      240
ctacccgctc ttcttttttga aagttccttt tccatggaaa tacaccaaat caagaaatgt     300
atggcacaaa tggtgttact tgctggacct ggtgtgctaa tatcaacctt tttcctaggc      360
tctgctctaa agctcacttt tccatacaac tggaactgga aaacatcatt gttgcttggt      420
ggattgctta gtgcaactga ccccgttgct gttgttgcac tgctaaaaga acttggcgca      480
agtaaaaagc ttagtaccat aattgaggga gaatccttaa tgaatgatgg gactgctatt      540
gttgtgtatc agttattcta taggatggtg cttggaagaa ctttcgatgc aggatcaata      600
ataaaattct tgtcagaagt ttcacttgga gctgttgctc tgggccttgc ttttggaatt      660
gcatcagtac tgtggctggg ctttattttt aatgatacaa tcatagagat cgcacttact      720
cttgctgtca gctacattgc tttcttcact gcacaagatg cactggaggt ctctggtgtt      780
ttgaccgtca tgacactggg aatgttctat gccgcttttg caaaaactgc ttttaagggt      840
gacagtcagc aaagcttgca tcatttctgg gaaatggttg cttatatagc aaacacactt      900
atatttatac tgagtggggt tgttattgca gatggagtac tagaaaataa tgtccatttc      960
gagaggcacg tgcttcatg gggcttcctt cttctgctct atgtatttgt gcaaatttct      1020
cggatattag ttgttgttat tttgtatcca ttgttgcgcc actttgggta tggtttggac      1080
ttgaaagaag ccacaattct tgtttgggcg ggactgcgag gggctgttgc tctgtctcta      1140
tcattatctg ttaagcgtgc tagtgatgca gttcagaccc atctgaaacc agttgacgga      1200
acaatgtttg tgttcttcac tggtggcatc gtgtttttga cattgatttt taatggttct      1260
actacacaat ttttgttgca tctacttgga atggacagat tagcagcaac aaagcttcgc      1320
atattgaatt atacaaaata tgaaatgcta aacaaggcat tggaggcttt tggtgatctt      1380
agggatgatg aggaacttgg tcctcctgct gattgggtta ctgtaaagaa atatatcaca      1440
tgcttgaatg acttggacga tgagcctgtg catcctcatg ctgtttctga cagaaatgat      1500
cgcatgcata ccatgaactt aagggacatc cgtgtgcggc ttctaaatgg tgtccaagct      1560
gcttactggg gaatgcttga agaaggacga ataactcaag ccactgcaaa tattttaatg      1620
agatcggttg atgaagctat ggatcttgtt cctacccaag aattatgtga ctggaagggt      1680
ttgcggtcca atgtccattt tccaaattac tataggttcc ttcaaatgag caggttgcca      1740
cgaaggctta tcacttactt cacagtagaa agactggagt caggatgtta catctgtgct      1800
gcatttctcc gtgctcatag aatcgcaaga cggcagctac atgactttct tggtgatagt      1860
gaggttgcaa gaattgttat tgatgaaagt aatgctgagg gagaggaggc tagaaaattc      1920
ttggaagatg ttcgtgttac attccctcag gtgcttcgtg tgctgaagac tcgacaagta      1980
acatattcgg tattgacccca cttgagtgag tatattcaaa atctccagaa gactgggttg      2040
ctggaagaaa aggaaatggc ccatctagat gatgctttgc agacagactt gaagaagttc      2100
aagaggaatc caccattggt aaaaatgcca agagtcagtg atcttttgaa cactcatccg      2160
ttagttggtg cactgcctgc tgcgatgcgt gatcctttat taaatagcac aaaggaaaca      2220
gtaaaaggac atggcacaat cctttataga gagggctcaa ggccaactgg tatatggctt      2280
gtttcgattg gagtagtaaa gtggacaagt cagagattaa gcagcaggca ttcattggat      2340
ccaattttat cacatggcag cactttgggc ctgtatgagg tgctgattgg aaaaccttat      2400
atctgtgaca tgattacaga ttctgtggtg cactgcttct tcattgaagc tgaaaagata      2460
gagcaattgc gtcaatcaga tccttctatt gagatttttc tgtggcagga aagtgctcta      2520
```

| | |
|---|---:|
| gtcgttgcca ggcttttgct ccctatgatg tttgagaaaa tggcaacaca tgagctcagg | 2580 |
| gttctcatca ctgaaagatc tactatgaac atctacatta agggcgaaga aattgaactt | 2640 |
| gagcagaatt tcattggcat cttactggaa ggattttga agaccaagaa ccaaactttg | 2700 |
| atcacacctc cagggttact gctaccacca aatgccgact tgaacttatt tggtctcgag | 2760 |
| tcatcagcta taaaccgcat tgactactgt tatacagcac ccagctatca ggtggaggct | 2820 |
| agagcaagga ttttgttcgt tgagataggg aggcccgaaa tagaggcgga tctgcaaagg | 2880 |
| agtgcgtcat tgatatctca aacccttgaa ctgcctcgga cacaaagcaa ggagcacagc | 2940 |
| ggtttgctca gctggccgga aagcttcaga aaatccaggg gagctcagaa tggtgccagc | 3000 |
| ttaactgaaa tcagagacca tccagcaagc ttctctgcaa gagcattgca gctgagcatg | 3060 |
| tacgggagca tgatcaatga catgaagtcc ggtcagggtc aggtcagag gaggcagagg | 3120 |
| catcgtcaca cgaaagcaag ctctaataaa gcgcacagct cgtcgtaccc aagagtgcct | 3180 |
| tcgaggtcgt ccaacacgca gaggcccctg ctgtctgtgc agtccgaggg tgccaacatg | 3240 |
| acgacggcaa ggcaggctgc tgctgctggt gcttctctgc cgccggagcc ggaggaggca | 3300 |
| ggacggcggc ggcggcgaca acgcaaggca atagaagagg acgaggacaa ctcgagcgat | 3360 |
| gagtcggccg gggaagaggt gattgtcaga gtcgattctc ccagcatgct caccttccgt | 3420 |
| cagccctcca gcgctgctga tcgatga | 3447 |

<210> SEQ ID NO 9
<211> LENGTH: 1596
<212> TYPE: DNA
<213> ORGANISM: Oryza sativa

<400> SEQUENCE: 9

| | |
|---|---:|
| atgaatcatt gtcttgtagt atcccacaaa aaactccaaa ctttccgcac atttgcagct | 60 |
| agcaagttct cttcttttac caaatctgca cagaagtcta taaaatactc cttccagttc | 120 |
| atctaccaaa acaatccact cttttgtccat gtagcttact ttgccctgat ctcctttgct | 180 |
| ggatatggat ctctaaaggt cctcaagcca cgagacaagt caaatactct gaaagacttg | 240 |
| gacgtgctat ttacttccgt atctgcatca actgtttcaa gcatggctac tgttgaaatg | 300 |
| gaggatttct caagcgctca actctgggtt ttgactattt taatgctgat tggtggtgag | 360 |
| gtattcactt caatgcttgg cattcacttt atgagagccg aatttggtac aaaagagtca | 420 |
| gtcagcacaa gggatcactc accttgcatt gatattgagt ctattacttc cacaaaattt | 480 |
| ggtcccagca cccagggcac aaaagttaca gtttcatttt ctgaactccg catggaaaat | 540 |
| ggaggacatg tagagcccaa gacgattaaa tttttaggtt ttgtagtgat gggatatctt | 600 |
| ctaataacaa acttaggcgg ctccctactt atttacctct accttaacct ggtaccaagt | 660 |
| gcacataaaa ttctaaagag aaaaggcatt gggatcatcg tattctcagt atttacagcc | 720 |
| atctcctcag ttggaaattg tggcttcact ccagtaaatg agaatatgat tatctttcag | 780 |
| aagaactcca ttcttctatt gctaattctt cctcagatac tagcaggaaa tacattattt | 840 |
| gcaccatgct tgagattaat ggtgtggtca cttgagaaga ttaccggaaa aaaggattgt | 900 |
| cgttacattc ttgaatatcc aaaggccatt ggatataaac atcttatgag taccagggaa | 960 |
| agtgtttatt tgactttaac agttgtgagc ttgatcattc tgcaaaccgt attgttcctc | 1020 |
| tctttggagt ggagctcggt agctttggat ggaatgagca actatcaaaa gatagtatcc | 1080 |
| gctctatttc agtcggtcaa tgctaggcat gcaggtgaat ctgttacaga tctgtcaaac | 1140 |
| ctctcttcag caatcctagt cctatacacc atcatgatgt atctccctgg ttacacttcg | 1200 |

| | | |
|---|---|---|
| tttttacccca | gacatgatgg tgaggattct aagaccgaga agataaacaa aagaaaaggg | 1260 |
| ctattggaga | actggatctt ctcacatatg tcttatttgg ctatctttgt aatgctaatt | 1320 |
| tgcatcacag | aacgggactc gatggctaca gatccactta atttcaatgt tttcagcata | 1380 |
| ttgtttgaag | tcgtcagtgc atatggaaat gtggggttct cggttggcta cagctgcaag | 1440 |
| aggctactga | accatgatgc acgctgcaag gatgcctcgt acgggtttgc ggggaaatgg | 1500 |
| agcgacaatg | ggaaagcgat cctgatcatc gtcatgcttt tcgggaggct taaaacgttt | 1560 |
| aacatgaagg | gtggaagagc ctggaagctt agataa | 1596 |

<210> SEQ ID NO 10
<211> LENGTH: 1665
<212> TYPE: DNA
<213> ORGANISM: Oryza sativa

<400> SEQUENCE: 10

| | | |
|---|---|---|
| atgagttctc | tggatgccac tactcctaga tatgacgagt ttaaaaggat ctaccacctt | 60 |
| ttcctttcc | atgcacaccc attctggctc caactgctgt acttcctctt catctccctc | 120 |
| ttgggtttct | tgatgctgaa agctctgccg atgaagacca gcatggtgcc gaggcccatg | 180 |
| gacttggacc | tgatcttcac gtcggtgtcg gcgacgacgg tgtcgagcat ggtcgccgtc | 240 |
| gagatggagt | cctt ctccaa ctcccagctc ctcctcatca ccctcctcat gctgcttggt | 300 |
| ggtgaggtct | tcaccagcat ccttggcctc tacttcacca acgccaagta ctcctccaag | 360 |
| atgatagcaa | ccttacctga tgatgacgac catggtggca gtggcaaacc accaccacca | 420 |
| acgacgtcac | cttcgtctac cctagtggag ctcgagctcg ctcctcccat ggacgtcgtc | 480 |
| gtcgtcaacc | ctaccaccac tgcgacgacg cacgacgagg tagagctagg gttaggacgt | 540 |
| cggaacaagc | gcggctgcac ctgcactact actcacacgt cgtcgtcatc atcggcatcg | 600 |
| aagacgacga | cgacgaggct actgatgttc gtggtgatgg ggtaccacgc ggtggtgcac | 660 |
| gtcgccgggt | acacggccat cgtcgtgtac ctcagcgccg tcggcggcgc gggggcggtg | 720 |
| gtcgccggga | aggggatcag cgcgcacacg ttcgccatct tcaccgtcgt ctcgacgttc | 780 |
| gccaactgcg | ggttcgtgcc gacgaacgaa gggatggtgt cgttcaggtc gttcccgggg | 840 |
| ctcctcctcc | tcgtcatgcc gcacgtcctc ctcgggaaca cgctcttccc ggtcttcctc | 900 |
| aggctggcca | tcgccgcgct cgagagggtc accgggtggc cggagctcgg cgagctcctg | 960 |
| atccggcggc | ggaggggcgg cggcgagggc taccaccacc tgttgccgag ctcgcgcacg | 1020 |
| cggttcctgg | ccctcaccgt ggccgtgctc gtggtggcgc agctggcgct cttctgcgcc | 1080 |
| atggagtggg | gctccgacgg gctgcggggg ctcaccgcgg gccagaagct cgtcggcgcg | 1140 |
| ctcttcatgg | cggtcaactc gaggcactcc ggtgagatgg tgctcgacct ctccaccgtg | 1200 |
| tcgtcggccg | tcgtcgtgct ctacgtggtg atgatgtacc tgccaccctta caccactttc | 1260 |
| gtacctgtcc | aagacaaaca ccagcaaacg ggagcacagt ccgggcagga gggcagcagc | 1320 |
| agcagcagca | tatggcagaa gctgctcatg tcgccgctct cgtgcctagc catcttcatc | 1380 |
| gtcgtcatct | gcatcacgga gcggcggcaa atcgccgacg accccatcaa ctacagcgtc | 1440 |
| ctcaacatcg | tcgtcgaggt tatcagtgcg tatggcaatg tggggttcag cacggggtac | 1500 |
| agctgcgcga | ggcaggtgag gcccgacggc agctgcagag acctgtgggt tggcttctca | 1560 |
| gggaagtgga | gcaaacaagg gaagctcact ctcatggccg tcatgttcta cggcaggctc | 1620 |
| aagaagttca | gcctgcacgg tggtcaggca tggaagatag aataa | 1665 |

```
<210> SEQ ID NO 11
<211> LENGTH: 24
<212> TYPE: DNA
<213> ORGANISM: Artificial sequence
<220> FEATURE:
<223> OTHER INFORMATION: Target sequence

<400> SEQUENCE: 11
gctctgcgcc tgcatcgtcc tcgg                                          24

<210> SEQ ID NO 12
<211> LENGTH: 24
<212> TYPE: DNA
<213> ORGANISM: Artificial sequence
<220> FEATURE:
<223> OTHER INFORMATION: Target sequence

<400> SEQUENCE: 12
gtccatcacc gcgctcatca tcgg                                          24

<210> SEQ ID NO 13
<211> LENGTH: 23
<212> TYPE: DNA
<213> ORGANISM: Artificial sequence
<220> FEATURE:
<223> OTHER INFORMATION: Target sequence

<400> SEQUENCE: 13
ggctgtcgtt ctgaaattct tgg                                           23

<210> SEQ ID NO 14
<211> LENGTH: 23
<212> TYPE: DNA
<213> ORGANISM: Artificial sequence
<220> FEATURE:
<223> OTHER INFORMATION: Target sequence

<400> SEQUENCE: 14
gagtttgcca gtgacagacc tgg                                           23

<210> SEQ ID NO 15
<211> LENGTH: 22
<212> TYPE: DNA
<213> ORGANISM: Artificial sequence
<220> FEATURE:
<223> OTHER INFORMATION: Target sequence

<400> SEQUENCE: 15
gtcgttcttt ttagcactat gg                                            22

<210> SEQ ID NO 16
<211> LENGTH: 23
<212> TYPE: DNA
<213> ORGANISM: Artificial sequence
<220> FEATURE:
<223> OTHER INFORMATION: Target sequence

<400> SEQUENCE: 16
gctaaaaaga acgacagtga tgg                                           23

<210> SEQ ID NO 17
<211> LENGTH: 24
<212> TYPE: DNA
<213> ORGANISM: Artificial sequence
<220> FEATURE:
<223> OTHER INFORMATION: Target sequence
```

```
<400> SEQUENCE: 17
gcaaaattga gcttatccca atgg                                              24

<210> SEQ ID NO 18
<211> LENGTH: 23
<212> TYPE: DNA
<213> ORGANISM: Artificial sequence
<220> FEATURE:
<223> OTHER INFORMATION: Target sequence

<400> SEQUENCE: 18
gcaatccagc aaatactcca agg                                               23

<210> SEQ ID NO 19
<211> LENGTH: 22
<212> TYPE: DNA
<213> ORGANISM: Artificial sequence
<220> FEATURE:
<223> OTHER INFORMATION: Target sequence

<400> SEQUENCE: 19
gcaatagata ttgtgaaaaa gg                                                22

<210> SEQ ID NO 20
<211> LENGTH: 23
<212> TYPE: DNA
<213> ORGANISM: Artificial sequence
<220> FEATURE:
<223> OTHER INFORMATION: Target sequence

<400> SEQUENCE: 20
ggacaccacc gacgcgtagt cgg                                               23

<210> SEQ ID NO 21
<211> LENGTH: 22
<212> TYPE: DNA
<213> ORGANISM: Artificial sequence
<220> FEATURE:
<223> OTHER INFORMATION: Target sequence

<400> SEQUENCE: 21
gaaacaagaa gctgcgctaa gg                                                22

<210> SEQ ID NO 22
<211> LENGTH: 24
<212> TYPE: DNA
<213> ORGANISM: Artificial sequence
<220> FEATURE:
<223> OTHER INFORMATION: Target sequence

<400> SEQUENCE: 22 gttttttgaca ttgattttta atgg                                             24

<210> SEQ ID NO 23
<211> LENGTH: 22
<212> TYPE: DNA
<213> ORGANISM: Artificial sequence
<220> FEATURE:
<223> OTHER INFORMATION: Target sequence

<400> SEQUENCE: 23
gcaccatgct tgagattaat gg                                                22

<210> SEQ ID NO 24
```

```
<211> LENGTH: 23
<212> TYPE: DNA
<213> ORGANISM: Artificial sequence
<220> FEATURE:
<223> OTHER INFORMATION: Target sequence

<400> SEQUENCE: 24
ggtgcacgtc gccgggtaca cgg                                              23

<210> SEQ ID NO 25
<211> LENGTH: 3068
<212> TYPE: DNA
<213> ORGANISM: Zea mays

<400> SEQUENCE: 25
cgcagctccc cacttctcat cgccccgttt ttttaatttg tggccatctt tggggtggtg      60
ggcggaggat ttctaactgg atggtgaagt ttgtctggcg aaaaggacgg ctgcgacgaa     120
cccgtccatc gatccaacgc tgtgcgcgcg ttggggagg gacctgccag gccccacctg     180
cagcgacaga ctattgatag atgccttcct ctctgatcac ctgatggctg atgccttcgc     240
ggccgtcttc gcctgccgct gctactacta gttgccttcc tcgcttcccc gtctcgcccc     300
agccgcttcc cccctcccct acctttcct tccccactcg cacttcccaa ccctggatcc      360
aaatcccaag ctatcccaga accgaaaccg aggcgcgcaa gccattatta gctggctagc     420
taggcctgta gctccgaaat catgaagcgc gagtaccaag acgccggcgg gagtggcggc     480
gacatgggct cctccaagga caagatgatg gcggcggcgg cgggagcagg ggaacaggag     540
gaggaggacg tggatgagct gctggccgcg ctcgggtaca aggtgcgttc gtcggatatg     600
gcggacgtcg cgcagaagct ggagcagctc gagatggcca tggggatggg cggcgtgggc     660
ggcgccggcg ctaccgctga tgacgggttc gtgtcgcacc tcgccacgga caccgtgcac     720
tacaatccct ccgacctgtc gtcctgggtc gagagcatgc tgtccgagct caacgcgccc     780
ccagcgccgc tcccgcccgc gacgccgccc ccaaggctcg cgtccacatc gtccaccgtc     840
acaagtggcg ccgccgccgg tgctggctac ttcgatctcc cgcccgccgt ggactcgtcc     900
agcagtacct acgctctgaa gccgatcccc tcgccggtgg cggcgccgtc ggccgacccg     960
tccacggact cggcgcggga gcccaagcgg atgaggactg gcggcggcag cacgtcgtcc    1020
tcctcttcct cgtcgtcatc catggatggc ggtcgcacta ggagctccgt ggtcgaagct    1080
gcgccgccgg cgacgcaagc atccgcggcg gccaacgggc ccgcggtgcc ggtggtggtg    1140
gtggacacgc aggaggccgg gatccggctc gtgcacgcgc tgctggcgtg cgcggaggcc    1200
gtgcagcagg agaacttctc tgcggcggag gcgctggtca gcagatccc catgctggcc    1260 tcgtcgcagg gcggtgccat gcgcaaggtc gccgcctact tcggcgaggc gcttgccggc    1320
cgcgtgtatc gcttccgccc gccaccggac agctccctcc tcgacgccgc cttcgccgac    1380
ctcttgcacg cgcacttcta cgagtcctgc ccctacctga agttcgccca cttcaccgcg    1440
aaccaggcca tcctcgaggc cttcgccggc tgccgccgcg tccacgtcgt cgacttcggc    1500
atcaagcagg ggatgcagtg gccggctctt tccaggcccc tcgccctccg ccctggcggc    1560 ccccgtcgt tccggctcac cggcgtcggg ccgccgcagc ccgacgagac cgacgccttg    1620
cagcaggtgg gctggaaact tgcccagttc gcgcacacca tccgcgtgga cttccagtac    1680
cgtggcctcg tcggccac gctcgccgac ctggagccgt tcatgctgca accggagggc    1740
gatgacacgt atgacgagcc cgaggtgatc gccgtgaact ccgtgttcga gctgcaccgg    1800
cttcttgcgc agcccggtgc cctcgagaag gtcctgggca cggtgcgcgc ggtgcggccg    1860
```

-continued

```
aggatcgtga ccgtggtcga gcaggaggcc aaccacaact ccggcacgtt cctcgaccgc    1920
ttcaccgagt cgctgcacta ctactccacc atgttcgatt ctctcgaggg cgccggcgcc    1980
ggctccggcc agtccaccga cgcctccccg gccgcggccg cggcacggac ccaggtcatg    2040
tcggaggtgt acctcggccg gcagatctgc aacgtggtgg cgtgcgaggg cgcggagcgc    2100
acggagcgcc acgagacgct gggccagtgg cgcagccgcc tcggcggctc cgggttcgcg    2160
cccgtgcacc tgggctccaa tgcctacaag caggcgagca cgctgctggc gctcttcgcc    2220
ggcggcgacg ggtacagggt ggaggagaag gacgggtgcc tgaccctggg gtggcatacg    2280
cgcccgctca tcgccacctc ggcgtggcgc gtcgccgccg ccgccgctcc gtgatcaggg    2340
aggggtggtt ggggcttctg gacgccgatc aaggcacacg tacgtcccct ggcatggcgc    2400
accctccctc gagctcgccg gcacgggtga agctagacgt cattgagcgc tgaatcgcag    2460
ttagcgaccg ggccaaggtt ctcgccggcg tgatgagatg gaacactttg actcccgcgg    2520
ccggatcggc ctgtgttcgt tcttgtttcc gatctcccct ctctttcccg ttgcttcgat    2580
cccgtcaagt atggtagacc gtagcctatt gttatgttta aatgtcaatt attatgtgta    2640
attcctccaa gcgccgatat ccaataagga cgaaccggat tttcgttagc tcgacctcga    2700
atgagaattt tgtatacaat gcatcctcgt tagctatgtt catctgttcg aatgcttgtg    2760
ccctcatgtt ttcattccgt tcgtcctcta cacgaatggt gatcactatg tattgtgaac    2820
gagctcagtc atgtaggagc tgccagattg gaattcgcgg cttgctttgc ctttgaggag    2880
tatgaaaata ttatatgttt atctcacaag aactggtaag gtctgtttat ttcttttcct    2940
tgccgtgccc atcctgtaag aaatcctcca tggccgatgc ggaaacatct cgttgctttg    3000
ccttgcatgt atcccttcgc ctgtgtggcc gtcctctgcc ggggctgttc acgatctaaa    3060
aataaaaa                                                             3068
```

<210> SEQ ID NO 26
<211> LENGTH: 6746
<212> TYPE: DNA
<213> ORGANISM: Zea mays

<400> SEQUENCE: 26

```
atgaagctcc tctcgccggc ggccgcaccg tcgtcctcgc cgttgttccc tcctcgcatc      60
gtcgaaggta cgtgtacacc gtcgtcagca gctgctacct ccgcggcgcc ggccagccga     120
ggttccatga tgcctatcta tctatgtata gtacgtatat ggcgccgcgc caggcccttg     180
cccttgtcgt ctgcctgcat gcctactact acaagctact ccaaatttc gcattgtcct      240 cggcgctaca cggccggtgg gcaatcagac aaagaaacaa acgtgtaagc aagatgaaaa     300 attgtattt tgggttcgga caagcaagtc gtcgtcgtcg tcttagggta gccacacaca      360
caggcagatg ggcaatcaga caaagaaaca acataagca agatggagag aggcaggcag      420
gcagtcaggc gctgctgctg ctagtgctag ctccttgcttt gttgtgtgtc ctgatggtcg    480
agttcctcac cgctgctttt gcttttctgc tttcacttgc ctgcagctgc agctcgtcaa      540
tcaggtccat gccgtatccg catccgtatc cgtggcaaag cagcagcagc aggaggagga      600
ggaggcgcgg gcgcgacggg gccccgcggc agcctcaggc tcgccgggtg gtggagagcg      660
cagcagcagg ccccggccac ggcgacgaca acgcagcagc ctgacaacgt ctccagtgct      720
aaaggtgcta gcttgctcgt tatatttgat ttgactagtc tcatcatcca ccccccagtc      780
acgtacacag atgctctctc tctctctctc tcttgaattg atgagcgaac gaaacactca      840
```

```
gacagatgct gtgccgtgct gcagtgcgcc cgtagcagca cagacactct gccgcacgca      900
cctgcgcttg tcgcttcccc tcttgctata tctcctgctg cttttgctaa agccggaaac      960
caaaaagaaa gttgagcttt tcgtcacaat tttgctttac ttattaagtg ctagtccgtt     1020
ttgtttatac gaccttacta ttagcttcta gcccggattc aaagtgctac agtgcgtttt     1080
cactaacaac atttaggatt atagcacatc aaatttgact agtgttacaa aaatatatat     1140
tagcatcata catatttagt taaagttaaa aatatttaat ttgtatgaaa acaagagtg      1200 acactctcta tgggataggc cgagtacgca ccatgcatga ttactactat taggctatct     1260
ccagcagcgt tacctattct accttctatt tcaaacttta cttcgtaaac agtataattt     1320
gtaatgcaaa acaatgtttt atacggtcat atacacggtt cgctagccac agcctaaggc     1380
caactccaat agactgttct gtactgcaga cgacaatgtt tacatagtaa agtttgaaat     1440
actgattgaa gtacgtagtt tgctggagat agcataagcc tccttgataa ggctctttca     1500
aaggctcctc caacaactcc ttaaaaaatc tatgaaacgg gggctattcc gctagcttct     1560
cgttgaaaat agcaaggagc tgcttccaag aaacgagcaa agtcggggc tcgaaaagag      1620 gcttctaagg ctccctccca tcctccattc ctcccctctc tcatgggttc catgttggct     1680
gaaggtgctg catttcgtac taaatagggt gctcatcccg aaacttttg tgaaaacaag      1740 aacatagcta ttttcacaca agagccaaaa ccagagttgg agttgttgac acaaaagtct     1800
aactaaaggc gggcaaacat gcatacctgg tattccgcgg tgtgttggtc ttgcatatat     1860
tcaattttcc tattaagttc acaatgttta catttattta tttactaggt aggtgctcgt     1920
gtatggttac cgtttctata tatcatatag gtagaccttg attaaatgtg atagttattt     1980
agacacagct gatccattta atattgttac gacctgatac gacactattt gaaataggcc     2040
catgttggac tagcccgcaa gtgccgatcc agcctgatac gattatatta agatatatat     2100
atttacaatg tatatccttg gtatataaga aatgtctttc ctataacaca aaagcagatg     2160
agttgtattg gccagcacct tccctctata aggcgcatgg tcgaggcgct gcagaggagg     2220
cacataggga gggaggatgc acaacgattt tgacacttag ggctagtttg acaactcaat     2280
ttttctaaca ccccgtttgg atcattggaa ttgaattcca ttctaataac agtaatttag     2340
gtatatatca attaagctaa ttcggtttta tgtaaaatat atttgtatac tattattatt     2400
aagatgtcgg agatatttat gtgctatatt tttagtatag aggagtgaga cgaatagggt     2460
catgtaattt acagagtaca aacaaattct actaatacat aaaatcattt tcaatcctcc     2520
accccatgaa ttcgaggtaa ccttatatct ggactttaga aaatggtgga atatcaaatt     2580
tcgagctaaa tatgttactt tattgaatga atttcaattc ctttaaaatg aagggattca     2640
aacggcccgc aagggaaaat aaactggttt cattggaaaa tggaaatttc ttcaaagaat     2700
gggattgcca aactagcctt taaagtagta ggagatctat ttatttattt tgacaaaata     2760
tatgaaaaaa aggttttagc tccttcacga tcatcgatcg atgccttatc ggtgacggaa     2820
ggtggatcgc tatcaaccgt actgctgcaa acagtagttg actgcgaaat taagattctt     2880
gatgtgtgat tgattatgag gtaactgtcc acattgtcct cttttgtttct tgaccccaaa     2940 tccttggcga actttactca tcaatcacaa aggtatctct gtatgtgtgt ggtcagaggg     3000
atcctgtcct ccttgtaccc cactgttctt tttagctaat gcaaattgcc attggatcaa     3060
cttggtgatt tgatggata cagagatcaa atatccgatc aggaatatag tagatatggc      3120
actccaaggt agatagatga ttagactgga ccgcagaggt atcttcagtt ttttttttgcc    3180 atgtaactcg cgcgcacagc agggaatctg attgtgtgtg taagggagat tttaaagaac     3240
```

```
tggccatcta tcttctgttg ggagaaatga agtcaaaatg ggtaatgcag tgctgaatct   3300
gacgctctag ttgacgttac gctgctctgc tcaggccagc aggttcatgg tcctttgttg   3360
catgctgaac acttgctaga gatgcaattg ggtgccgaaa aataaaccaa cagtagctca   3420
atctgaccag tcacataatt ttcttcagtt ttcctccttt gagaaatgtt ttgttggagc   3480
tgggttttcc tgcagtgttc cagaccagcc gtgtggaaac cgagtccgaa attgcgaaat   3540
ggccagggaa accacaagac cttgaggatg agcaccaggt ggtccgtctt aggttgtttt   3600
cagttcacag atgcttgttg ctgaaattaa taaatcttcg tctgtaggct gaggaggcag   3660
agctgcagcc acttatcgac caggtgaggg cgatgctacg gtcgatgaac gacgggata   3720 ccagcgcctc ggcgtacgac acggcgtggg tggcgatggt gccgaaggtg ggcggcgacg   3780
gcggcgccca gccccagttc ccggccaccg tgcgctggat cgtggaccac cagctgcccg   3840
acggctcctg gggcgactcg gccctgttct ccgcctacga ccgcatgatc aacaccctcg   3900
cctgcgtcgt cgcgctgacc aagtggtcgc tggagcccgc gaggtgcgag gcggggctct   3960
cgttcctgca cgagaacatg tggaggctag cggaggagga ggcggagtcg atgcccatcg   4020
gcttcgagat cgccttccct tctctcatcc agacggctag ggacctgggc gtcgtcgact   4080
tcccgtacgg acacccggcg ctgcagagca tatacgccaa cagggaagtc aagctgaagc   4140
ggatcccaag ggacatgatg cacagggtcc cgacgtccat cctgcacagc cttgaaggga   4200
tgcctgacct ggactggccg aggcttctga acctccagtc ctgcgacggc tccttcttgt   4260
tctctccttc ggctaccgct tacgcgctga tgcaaaccgg tgacaagaag tgcttcgaat   4320
acatcgacag gattgtcaaa aaattcaacg ggggaggtaa gccgatcgtc catgcatgga   4380
ggattaatta agacgatcga tgatgtttaa tccgtgtctc gtctcatcag actgtttgcc   4440
atcaccgttt cagtccccaa tgtttatccg gtcgatcttt tcgagcacat ctgggttgtg   4500
gatcggttgg agcgactcgg gatctcccgc tacttccaac gagagattga gcagtgcatg   4560
gactatgtga acaggttttt gcttctgcga tcgatcactc tttatgtgaa caggtttttt   4620
tatgacagat tgagtagatg aatttctttg acttgtcttg tcatttcgcg taggcactgg   4680
actgaagatg ggatttgctg ggctaggaaa tccaatgtga aggatgtgga tgacacagct   4740
atggctttcc gactactaag gctacatgga tacaatgtct ctccaagtat atataaacac   4800
cattcccttt ttagcttaaa catctcatta acttgttatt atatcttaat gacataagcc   4860
agccgtgttc tgtaggtgtg tttaagaact ttgagaaaga tggagagttc ttttgttttg   4920
tgggccaatc gactcaagcc gtcactggga tgtataacct caacagagcc tctcagataa   4980
gttttcaagg agaggatgta ttgcatcgtg ctagggtttt ctcgtatgag tttctgagac   5040
agagagaaga acaaggcatg atccgtgata aatggatcgt tgccaaggat ctacctggcg   5100
aggtaatcca aaccattcta ccatttgatg atcttagatc cattgaaaca tgcatgaata   5160
gaggcgaaaa ttgacggtg ttatttttt ggctttcatt tgttgatcg ataggtgcaa   5220 tatacactag acttcccttg gtatgcaagc ttgcctcgtg tagaggcaag aacctatcta   5280
gatcaatatg gtggtaaaga tgacgtttgg attggaaaga cactctacag gtgcacactt   5340
gtactccaaa aaaaacgtt gatatacttc gttgcatact tattattagt gttttggca   5400 agaacctatc tagatcaata tgtaagagaa atgttctact tacatgtgcg gcgttttgg   5460 caggatgcct cttgtgaata acgacacata tctagagttg gcaataaggg atttcaacca   5520
ttgccaagct ctgcatcagc ttgagtgtaa tgggctgcaa acgtgagcac catcatttca   5580
```

-continued

| | |
|---|---|
| ttctccactt catgaatttt atgctggaag gttaactttg atttaattta caatattttc | 5640 |
| taaactatat tttaggtggt acaaggataa ttgccttgac gcttttggag tagaaccaca | 5700 |
| agatgtttta agatcttact ttttagctgc tgcttgcatt tttgaaccta gccgtgctgc | 5760 |
| tgagcggctt gcatgggcta aacgtcaat gattgccaat gccatttcta cacatcttcg | 5820 |
| tgacatttcg gaagacaaga agagattgga atgtttcgtg cactgtctct atgaagaaaa | 5880 |
| cgatgtatca tggtgagtac tgtaccttaa ttatatcagt taaccattat atatccattt | 5940 |
| aagaatcatc ttgaagcact tgtcatttac caagtagtag taacattggc atttgatttc | 6000 |
| ttaaacaaac aaataaataa attgggtaat agaacgaatg aatttcataa ttatatatag | 6060 |
| gaagatcaat aatgatattt taacaataag gatttatgta gttacgtaat ctttgttata | 6120 |
| tatactcatc gcagtgtaca tataaaagta aattgtacca aattgatctt tgatattcag | 6180 |
| aatatgcatt agcatttatt gcatgagtca atattgtgca ttagttacat atattacaaa | 6240 |
| agaggtaaag atgacgtcat attctttttt agcttccttt ttgtcaactc gtgtggactg | 6300 |
| attgtgcttt attctggtgg ccattatgtc atgccactta attttttga tgtattatta | 6360 |
| tcgcctctta agttatgacc tcaatgaaaa cttgcataag ttcattgata tatactttag | 6420 |
| atattttata tcgatgttgt aattttttaac tcgcattta caccgacctc ttttatttta | 6480 |
| gctgttttat ttaacatgtg tattctattt tcatcgtgtc atatattatg taatatatga | 6540 |
| aattgagaga atattttttt cctgacataa atgataaatt caggcttaaa cgaaatccta | 6600 |
| atgatgttat tcttgagagg gcacttcgaa gattaattaa cttattagca caagaagcat | 6660 |
| tgccaattca tgaaggacaa agattcatac acagtctatt gagtcttgca gtaagttatc | 6720 |
| cccacttgta cttaattaga ttataa | 6746 |

<210> SEQ ID NO 27
<211> LENGTH: 1131
<212> TYPE: DNA
<213> ORGANISM: Zea mays

<400> SEQUENCE: 27

| | |
|---|---|
| atgtttccctt tctgtgattc ctcaagcccc atggacttac cgctttacca acaactgcag | 60 |
| ctaagcccgt cttccccaaa gacggaccaa tccagcagct tctactgcta cccatgctcc | 120 |
| cctcccttcg ccgccgccga cgccagcttt ccctcagct accagatcgg tagtgccgcg | 180 |
| gccgccgacg ccacccctcc acaagccgtg atcaactcgc cggacctgcc ggtgcaggcg | 240 |
| ctgatggacc acgcgccggc gccggctaca gagctgggcg cctgcgccag tggtgcagaa | 300 |
| ggatccggcg ccagcctcga cagggcggct gccgcggcga ggaaagaccg gcacagcaag | 360 |
| atatgcaccg ccggcgggat gagggaccgc cggatgcggc tctcccttga cgtcgcgcgc | 420 |
| aaattcttcg cgctgcagga catgcttggc ttcgacaagg caagcaagac ggtacagtgg | 480 |
| ctcctcaaca cgtccaagtc cgccatccag gagatcatgg ccgacgacgc gtcttcggag | 540 |
| tgcgtggagg acggctccag cagcctctcc gtcgacggca gcacaacccc ggcagagcag | 600 |
| ctgggaggag gaggagatca gaagcccaag ggtaattgcc gcggcgaggg gaagaagccg | 660 |
| gccaaggcaa gtaaagcggc ggccacccccg aagccgccaa gaaaatcggc caataacgca | 720 |
| caccaggtcc ccgacaagga gacgagggcg aaagcgaggg agagggcgag ggagcggacc | 780 |
| aaggagaagc accggatgcg ctgggtaaag cttgcttcag caattgacgt ggaggcggcg | 840 |
| gctgcctcgg ggccgagcga caggccgagc tcgaacaatt tgagccacca ctcatcgttg | 900 |
| tccatgaaca tgccgtgtgc tgccgctgaa ttggaggaga gggagaggtg ttcatcagct | 960 |

```
ctcagcaata gatcagcagg taggatgcaa gaaatcacag gggcgagcga cgtggtcctg   1020
ggctttggca acggaggagg aggatacggc gacggcggcg gcaactacta ctgccaagag   1080
caatgggaac tcggtggagt cgtctttcag cagaactcac gcttctactg a            1131

<210> SEQ ID NO 28
<211> LENGTH: 6626
<212> TYPE: DNA
<213> ORGANISM: Zea mays
<220> FEATURE:
<221> NAME/KEY: misc_feature
<222> LOCATION: (2678)..(2777)
<223> OTHER INFORMATION: n is a, c, g, or t

<400> SEQUENCE: 28
atggtgaggc atctttaggt ttatttcacg cgcgcgcagc gcaccattat tagtcgtttt     60
cagctcgggc tcggatttaa tttgcgtgta tatatggtag gaggcgtacc acgagatgct    120
ggtgaagttc agggaggagc tgacgaggcc gctgcaggag gcgatggagt tcatgcgaag    180
ggtggagtcg cagctgaact cgctttccat ctccggaagg tcgctgcgca acatcctttc    240
atctggtact gaagttgctg cggcccatgc ccctcttatt ttatattaga tgatttcttg    300
gatcggttgt cgcctcatgc agcgatgcat gccctccctc ttgttaaaat cttcctgtcc    360
tctccttcgt cttgctgtcc tctttcttgg ttgagcatat gttgatgggt ttttttttt    420 gcatttcaaa agggttaaat ttttccttga tgtggtttct cagcaattaa ttttggcatc    480
tgtgtagttc ccttttttaag agcatcttgc tatgcatgca tattttgagt atagatagct    540
gcggaacgca gatgaatgtc ttgtctgcgc ttcatgtttt taatgcgcg gcagcattcc    600 taatcagggg tttcgaaaga gaatcttctc cctgcttgct tttcctggcc atgcatctgt    660
gagattcttc tctctggctt ccgtcgatct ttgcttctgc tggaaaggaa atagtcctca    720
gtcacacatg tgcaggagcg cagcttcaat ctagcatggc tgaaagctct ctggttcttt    780
ccatacactc catcctgcac attccttgca tatattctgc tgttaaactg cttagcgacg    840
aggatgaatg aaaacacctg tcttttttac tagtgggagt actaatttgg ctgctgttgc    900
catggatgcg ttgttcatcg tcctccatta tattgatcga ttccatttgg aatgaacat    960 gtgcatgtgt tctgcgagta gttcctggct cagcgcagcc atcttttccc atgatgggaa   1020 ccccaggag ttcccttgtt ctagggtttg gaaagggcc acagtgtact gggtgctgtg   1080
gcattgtgca agcacagtct atagccgagg agtctcactg gcgtatgtca gtgaaacata   1140
gtagtataca cgttgtagta gtgggagatc agagagagag agagatgggg agtcatcccc   1200
catctgtcac gcaagcttgt ggccagaaca ttcttgtcat ctttctcccc ctcaagagat   1260
gtagctacct gttgtcctag aatctatagt gttgtggtgt ggtcttccag gttgcgcacac   1320 agatctggcc actgctggcc ttagtatttg ctaattttaa aatgaacaca tcaggtagat   1380
cgagacgatc catggcaagc gtcttttctaa tgacctatca caaggctata gtaacaactc   1440
gtaccaccac agttacgcac agcccagagt ttttcacttc tcggttctgt tcttcttaga   1500
gcactggcta tggctagtat atatgcatgg cagcaacaca cacacacaca cacaatcact   1560
tcattactgg agcaagttag cgaagaagct gccatctgat gtcgtagaat gctgcaaaaa   1620
tgaaaggttc agaggcaggc atacggggttg aaatggagca ccgtatgcgg cggcccagtt   1680
ttttgtgttc tgaccggcgc agtggacaaa atggcctgtg tgcctcgaga accatagaga   1740
cagttgccta gcgcatgagc gctgagcggc cctattatt tgatgtgaga tctctctatc   1800
```

```
aatggatgtg tgatctgcta ggtttatatt atatatgcgt ctactatatc cctaccagtc    1860
cctgtatttt ctgacagata gacttctccc ccgcgcgttc tctcataaat aaatgacggt    1920
caaggaacat tggatgcttt ccgaggcgag ctagtacaag tttcatctgc gtttgcgttt    1980
gtattttcca gctgtcaact cagatttctc ctcagctcca actgttcttt gaccttcttg    2040
gtactgtttt cttggaagaa actatttgtt gaccatttt ggttataata aggccacaga    2100
caaactgttg aatttaatca caaaacaaca ctactgcgtt ttttcttttc ttttctgact    2160
gatgttgcac atgtactcca agattcttgg ttgcatgcac tctttcaagg tcatgcaaaa    2220
gcaaggacac cgggtgtcac gagtttccgt ttgtctcgag gtaagaccaa aaaagatacc    2280
ggaagcaaac aacataaaac aaagggtagg atggaaaaga gctgatggat tttacaatgt    2340
atcgccagag tggaaaagac aacgcgacta gaggaaagga acgatctggc acttccaact    2400
gtgtgaattc ttccatttga tgtgcgtctc gtgcatgttt attttcttgg ttactggaaa    2460
tcgggtgcat ccattttat tcaggattca attattggtt actggagcca ggtccgttcg    2520
tttttatttt cctttgaga ttgactggat cgattctctg gttctagtca cttatgctgt    2580
tggttttatc gttttcatgg atttcgattc tatctctccc aatattcagt aaacataaaa    2640
gcctgtgact atatttcttt tttttctaat tcttgtannn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnntcg ttttcaatgg atttctattc tatcttttcc catattcagt    2820
atcacataaa atcctgtgac tagatttctt tatcacatac aatcttgttt tttattttc    2880 tttaatttaa cactggattt gtttgataat atgttctgaa aaacgttaat aaatttaagc    2940
acaacagcct tttaaaaata tgtataatta tttaccttga aacccagcat cggccgggaa    3000
caaggaaaag aactcaaggt tttaaatgca ttgaaatgaa acattaatgg agtgtttggt    3060
ttgaataatg atgtagtcca tcatcttctc actcctcact tttttgtttg gtttatggaa    3120
tggagtgagt taatccatca acacctcatt cctcatagtt agttgtttag tactaatatg    3180
tggaatgaag tcatcccacc aaatttgaag aatggactca tgatgcacca cttcatttta    3240
gatagagtga ttcatcaaac caaacacctc ataagggcat gtttggatcc taggagctaa    3300
aagaaaagtg actaaagttt agtcacttta ggagctaaag atctactaaa taggaaacta    3360
aaagtgacta gaatagtaaa aggtatcttt ttagtcattt ttagctccta agaaggagct    3420
aaattttagt tagtttggtt tagctcttgg atccaaacag gccctaagaa aatgtttcga    3480
caacatttgg gacaataaaa cagttcctaa ggatttcttt ggcaagatta ggccttcttt    3540
ggaacaaaga aaatgaagg aatcttgaag gattgaaatc ctataggaag ctttcatatg    3600
caaagaattg tgttcctagg atgatttcta acaagaggct catccccttg aaaattgttc    3660
tttgtgtcta tctctctcct ctaattcatg tgttcttatg ttgcattgaa acactattag    3720
aaaattttca tgtgttttaa tttatgtatg attgtaagtg tcaagcagca ctattcctac    3780 atttttcta ttcctgtgtt ttatcgatac tgcatcccaa tgaaggccta agcgtatcat    3840
gcaatctttt ccagaagttt tttagattgc tgtataatga caaggtgcaa tgctcttcgt    3900
tttctttttt ggttttcctc attttcagca aggccaccaa atttttccat gatgttcttg    3960
tcttattcct gtagtatccc tcgaaaaaat ttcatagctt tctacatcca tgttatctaa    4020
tgatgttctt catttcaaag acagacacat ttggcataag ttctgattgg tcactaaaac    4080
tttgtggtac ggtcatttac ttttactata cacatgtact gtattcatgc gtacattgta    4140
ctttgtccat tggggccttt cctctttta atacaacggg catcgtttca aaaaaaatgt    4200
```

```
gtcagtcgta actgcacact tctttagttt tccccagtta acagcatgac ggaatagagt      4260
tacagagtct catgtcaagt cacatatatc ctcaagtcgt ttctaaaatt aaagtaatat      4320
tttcattgtt gcttccgtaa gaatgcacca caaacacaaa atatcatttc ctttatgcaa      4380
atatatatat atgaatgttt gtttctggca gtggtgagaa gcttctcact gagccaaagg      4440
ttttagggat gccatgtgct cttttctttt ttaagtgta gattaagcaa acctttataa       4500
tttttaaact ccaaccagat acctttcta aattcataaa tgctctggac tatcttcacg        4560
aaaaaggctt tggtaatatg ttcacaagcc tcctttatct gttatcctgg gctagacata      4620
ggatgtgttg aagcaataca agcggagttg tttcgttaaa gcaaaaaaaa aactgtaact      4680
ttatattgga gaatatacat cgttctccca tatttgttac agtgctcata aatagacaaa      4740
gttttttttt tgaaatctta agccctgtgt tctttggtt atcttatctc tatattgctt       4800
ccaaatatgt tgtcatcaag atggatatag ataattgtca aaacgaaaag tgtgcatggt      4860
tcatttatgc caattctgaa aagcataagt taaatattaa gataccaata aagaaaaaca      4920
tatgcagtgt tgactgttgg gaaaagaaca aggtctgcac atacacttgc aatataaatc      4980
tttttaccca gcaataaaaa aacgatcaaa tatcacgcaa acaaagtaat acgtccagaa      5040
acacccatac ttttgaaatt cgtctttgaa atgcagtagg ttcacaaaat aaaatggtgc      5100
aactgcacat gtcctttata tctgtactca atgggttttc tggagatgtt agattgattg      5160
gtgggacaat atcctaatgc aactcgcaaa ttcccaaggc cgaactcaag tgggagtttg      5220
gatgattttt tttgtaaaga agcagatggc tgcgctagtt tacatagacc atcacacttc      5280
acaattcaca ttcatgaagt cataactttg ttcacttctt gtttaactat ggcatataaa      5340
aacatactgt gtgttgtttt gcttgtatgg aacatgtatt ttagtttttt agtaaataag      5400
ttcagtaaat gtctttgccg gacaaatttc accaatctgg ctacgaatga tgcttgatca      5460
cttcttttgt tttatctaaa agttccatgt cttatgcttg aaggctcttc tgaggaggat      5520
caagaaggta gcggaggaga gaccgagctc cctgaagttg atgcacatgg tgtggaccaa      5580
gagctgaagc accatctcct gaagaaatac agtggctatc taagctcgct caagcaagaa      5640
ctgtcaaaga agaagaagaa agggaagctc cccaaggagg ctcgccagca gctccttagc      5700
tggtgggatc agcactacaa atggccttac ccctcagtac gtcttctttt tattcttcca      5760
ttttaactat tgttggtgac acatgattta gacgatgcca attcttcatg aacttttcat      5820
agccagctac ccaatgttag tactgactgc acattgtaat tcaagggtaa gtatatatat      5880
acataaatca catttggcaa atctaagcta catatgggtc tttgatcttc catgacggtc      5940
tgttgatctc tgatttgcat atcggcatat aaaagtgag ccaaaatatg tcagagtcta      6000
ataatattga tcagggagtg gcaggtgatt attggtatta atttaacctt atttaaggta      6060
ttttgaaact tctgtagcgt tcttactaaa taccattgat tttaatttaa gcaactatat      6120 attatctgg tgaaaatga agccttttct gatatacaaa ttgaagagtc tacaatggtt       6180
tcacttacat ggctgaaaca gaaaatcata gtgccctgaa ttgtgtgttg atactcataa      6240
gcgcagattc aaatttgtaa ttttcaagtt tagggttcta agtgaaaaaa aaacattgag      6300
tccaggagca tacactgaac ttttttttta tcatatcttc attttgttgg atgttttgta      6360
tacggcatat agcctgtgct tccctactgg atatgaatta accaactctt cccatcggtg      6420
agcaggagac tcagaaggtg gcactggctg agtctaccgg gcttgacctg aagcagatca      6480
acaactggtt catcaaccag cggaagcggc actggaagcc atccgaggag atgcaccacc      6540
```

```
tgatgatgga cgggtaccac accaccaatg ccttctacat ggacggccac ttcatcaacg    6600
acggcgggct gtaccggctc ggctag                                        6626

<210> SEQ ID NO 29
<211> LENGTH: 1703
<212> TYPE: DNA
<213> ORGANISM: Zea mays

<400> SEQUENCE: 29
atggtgctgg atctcaatgt agcgtcgccg gcggactcgg gcacgtcgag ctcgtccgtc      60
ctcaactccg cggacggcgg cttccggttc ggcctgctcg ggagcccccgt cgacgacgac    120 gactgctccg gtgagatggc gcctggcgcg tccacggggt tcatgacgcg gcagctcttc    180
ccgtccccga ccccgccggc cgagccgagc cggagccgg tggcggcgcc ggtgccggtg     240
tggcagccgc agcgcgccga ggatctcggc atggcccaga ggccggtggc gccagcgaag    300
aagaccaggc gcgggcctag gtcgcggagc tcgcagtaca ggggcgtcac cttctacagg    360
aggacgggcc gctgggaatc gcacatctgg tactcagcct ctgacctcgt ctgcacccctt   420 cgtaattacc atctactact gtgctaatct atggctcttg acgacttcca tttcctcctc    480 ctccttttcgc tgctgctcct gcttgatttg agcagggatt gcgggaagca agtctaccta    540
ggtgagtgcc tgagctcccc gcgttcgagc tccagcatct actatgaact gtcggttagt     600
tttactgcgc ttgatttggt tgccatctgc tgatgccctt actacccagg tggttttgac    660
actgcgcacg cagccgcgag gttagggagc gtttgcttgt ttgaattcgc gtccatttgc    720
atttctgtga tcgataggcg cgttgacacg gtcaagtttg gatcaagcag gcatacgat    780 cgagctgcga tcaagttccg cggcctcgac gctgacatca acttcagtct gagcgactac    840
gaggatgatt tgaagcaggt aatagttgca cgaaaacatc aaatggcatc tccggttgct    900
ccatgagatc catagtttcg ttgtggactg gtgatgatgg gtgtgctttc cagatgagga    960
attggaccaa ggaggagttc gtgcacatac tccggcgcca gagcacgggg ttcgcgaggg   1020
gaagctccaa gtaccgtggc gtgacgctgc acaagtgcgg ccgctgggaa gctaggatgg   1080
ggcaacttct tggcaagaag taagctggca caggcagtag aaaaactgac ctgcatacat   1140
agtagcacct tttatactct gttagcttca gttcaattat ttctatgcat gggtatgagc   1200
aaaaggcgct gggacgaagt tggcttgatt tcacattttg acacgagggt ggtcaatgat   1260
taattcgaca taatttaagc tcatgttagg caagcctgag ggtgatttta aggaatacgt   1320
acaacaagct ggtgctcgct ggggtcagtg tgcttgttgt ctagtatgct aatagtggtt   1380
agcacgtctc tgttatattg gtggaagctg cacttccttc caccactcaa tgttttgcca   1440
tggcacctaa cgatgtcata cagatctatt tgcagcaacc actagatttc agatatgagc   1500
atttgcagac aatgcacccc ccctgcactc cgtagtctag gaccagtttt gtcaaaacct   1560
accagcgtag gcatccttct ggtgagacag agagtatctc acaactcgaa ttcacatgca   1620
ggtacatcta tcttgggctc tttgacagcg aagttgaggc ggcaaggtgc cactgtagct   1680
gccttccacg tctcattttc taa                                           1703

<210> SEQ ID NO 30
<211> LENGTH: 3921
<212> TYPE: DNA
<213> ORGANISM: Zea mays

<400> SEQUENCE: 30
caaacaggtt gtgattgaca tatggacccc caacatgtga gcatgtgtat ctcttttgtc      60
```

```
tctctttttcc gcatgtacgg tgagagagaa ccaagaaaga gagataaaat agatacatag    120
gctaaaatgt ggggttcata tgtcaaccac gacgcgtttc gacctaacta agaccggaac    180
aacaattaag gaccagactg acacacttta aaagtttatg gaccgagtta acatataacg    240
tcatataagt tgaagtaatg aaaatgtatt ttactcttag gatatatcat cacaggagcg    300
gtacaccgtc gggttttttt tttggaggat gggggacaac tatcacgagg gatacaatac    360
aacttagtaa ggccgcgagg taacaaacta acaagtggcc catcgaaaca gtaaattgtt    420
tcccggcccg ctcggccgaa caagtgacgt ccccattcta aatctaagcc cacttctgac    480
taaccacaac gcaacgaaca aagcgacaac atgagaggca gacgaaggcc gccttccact    540
tttcgatggc gccatggaac agcctgaact gcgatgtgag acgtacggcg ccgcgccggt    600
gcaggcacac atcgacgacg cagctagaac atcggggcg gggggaggcc ggcggcggcg    660
tgggcgtggc tcccccgtgc ctggtggcag agctggcgca acctggtggg cacgtaccag    720
atggtgaggc gcgggtgcgc ggagaagacg gcgtcgatgt cgaagccgtg gcgcgcggcg    780
atctcgacga gcggcgcgta gcaggcctgc ctccaggcac cgacgttctc gccacgggcc    840
ttgtacgccc ggcgcagcgc gttggaggcc tcctcgtcca ggcagtgcag cgcgtagcag    900
tgcacgtagt gccgcatctt gggcttgttg atgtagctcg cgccgcactt cttggcgtac    960
cggaacacct ggttggtcac ctgcagtgca agcaaaaaaa aaaaaggttc atcagccacg    1020
gtcgattggt tccggtgtcg tgaaactggc cggtgtggtc gggtgcgcct ggcgcggacg    1080
caggagcagc gcatcgatgc agccgtccag gtcaggaaag ctatcatcat atccaatcag    1140
ccctggaatc cggacaggcc aggccgtgca ttcatttcac tgcgggcgag cacgcgagtc    1200
gcgactactc gtacgccggc caaactgcca aaagcgagct cacatggctc gtactggtac    1260
gcgcgaaacc ggtggcaaca gcacacaggc cacggactcc gagaggagag ggcgtccatg    1320
catgcctatc tgtatctgag gcctggggcc ggccggacaa gacaacacaa gctgcacagg    1380 cttttggcagc ctaccgatga ctgacacgtc gcgccttttt ccaggtcatc tacgtgcgtg    1440
tgcggctgta gcaaaatata cttgagtaca cgtacgtaga agtacttgac tacagactac    1500 tacgcgtac tatatagacc atcttttgca catgtgctac tgtagacgta cttacggtac    1560
acaaaatata atagaattcc actgcaaagg atttccttct tccttctagg tgatgtgaag    1620
ggccttttgc atgccactag atctttttta ctatgactat gatgttatta caatgaatag    1680
tatctgtatt tctaggattt gtgaaagttg aactagacta actttgatca aatttactat    1740
agcaaatagt attggtaatt ataccaac tagatatact tcattattat tctaacaatg    1800
tgcttattta acatcataaa tgttagtatt tttatatata actttagtca acccttaaac    1860
cgtttcacta ctaacaaagt tgagaattac gtcttcgtat taaattatta atagagttct    1920 gaccccttaac ttgtgtgact ccaactgtgt ctgagaatat ataacacatg ttttagagca    1980
aattataaac agtacctagc ttgtcaacga cctaaaaagt ttgtttcatt acattacgtt    2040
ttttaacact acagtttttg tttgtttatc gtacattcaa tctagctatc cgtatgcacc    2100
accaaatgga tttatacata tgtaatataa aaacgttgcc ctgctaaatt aataataagt    2160
gtgcgtacct tggtaggga cttgtggccg cccagcttag caagggactg cacctgcagc    2220
aggaagacgc ggcactgctc gtacagatgg aagaggtagt caagcccgtt cttcttggcc    2280
ctggccacct cgccgggctc tgtgaccacg aagggggtgct cccgctgcct ctccccgccg    2340
ccggagccgc cagcggaaga ctccgtcgag tctgacccgc cgccgccgcc gtcctcgtct    2400
```

```
ccgtcgttct cgtcgtccag cacgtccaac ggcctcagct ccttcttcct cctcgccttc    2460
ttgcccttcc tcgcgccaac ccctttcttg cccttcttct tgccggccgt caccatcctc    2520
ctgccggcct cgccttccgc caagccgccg ctggccgcgg cgtcgcgctc gtcggacagc    2580
actgccagtt gcgatatgat tgaacaagaa caaataacat cacaggccgg caagcagaac    2640
tcaactcaac atgactgaat catgggcact gtccgcatgc atgcacgagt gcacgaccac    2700
agaggcaaac aatttgacca tgctgtgtat accttcttgt gacgcggcgt ccaatgtgct    2760
cccggtgtgg aagcggccgc cgagggacat gacacgcccg cgctcggccc gcagcgcggg    2820
gcggaggccg aagcgctcgc cgaggagcac gtcccagcgg aacagccccg cgagcgcggc    2880
catcatgtcg tcgagctcgc gctccgtcat gccgaggagc gtgctggccg tgaacccgag    2940
ctccgagatc cgcgccaccg tggacgggcg cacgccgtag ccggccacca ggtcctccag    3000
ctccctcggc gcgctcagca gcggcgcgtg gggcagcagc tgcggcgcgg gcggcggtgg    3060
gggcggaggc gcgggcgcgg cgggcgccgg cgggcccagg tcccaccgga acgggtgcgc    3120
cgccgagaag gcgtcgttgg gatccatgct ctcgactctc gagggttgcc aacctaactc    3180
gtgctccttg actccgtgtt gctgttgcct gccgccttgc cgtgcgctgg atcctgttat    3240
atagcggcaa ctgttttttt tttttttttt tgcaatgcaa tgcgaggccc gtggacttgc    3300
gagacgcact gcactgtagt cctagtctac tagcgcttgg tgtttgtcgg ctgctccaag    3360
cgagcgtgct ctgctacgac gtgaaaacga ctagtcctgt agaaagctgc accgcaccgt    3420
cgtcgtcgct cgcccctcgc gatttgatag tctagattct acgcgcccta cattacgtgc    3480
tggaacataa aaagaagaca cggcgaggct gataaatact cccacaccac ctgcattgcc    3540
cagtcccgtc gcggcgttcg tgtcgtggat gtgtcccgtt gcacgtctcg gtggctaggc    3600 tttcttttc ttccagctcc gtctgaaatc tatggggagt actgtacgtg aggcgacgtg    3660
gatttcagag ctcaccgtgg ataaggatac ttagggttca tggttcaaga ggtgcggtgg    3720
ccgttgcttg aacggcggtg ccgactgcag gcgaagcgaa gagtggattt tggagtacaa    3780
accggacgtc tctgctgttg cacgggacgt ttggcaatgg cacggattcg agaccagact    3840
tcacaagctg cttctcagct ttcaatcagc cacagccaga cagcgtgccc acgagcacga    3900
ccagcttcac gggccagatc c                                             3921

<210> SEQ ID NO 31
<211> LENGTH: 3793
<212> TYPE: DNA
<213> ORGANISM: Zea mays

<400> SEQUENCE: 31
acaggaacag gactagtcgt tttcacgtcg taacagagca cgctcccgcg tcgatagatc      60
gctacgagca gtcgacagac acggcagcat aaatgcgcgc gcaaaagcta gtagtaggac     120
taggcctaca gtgcagtgcg tccccgagat tcattcgtca agttcaggtc gaccggccgg     180
ccttgccctt gcattggaaa acagttaccg ctatataaca aacagccgcg cgcacggcg      240 agccaagccc gtcaaggcac gaggactgca ggagcagaaa gttggcaacc ctttgagttc     300
ctcactcaca cgcgcgcgag ccgagagagc atggatccca cgacgccttt ctcggcggcg     360
cacccgttcc ggtgggacct cggcccgccg gcgcacgccg cgcccgcgcc cgcgcctccg     420
cctccgccgc tagcaccgct gctgctgccg cctcacgcgc cgcgggagct ggaggacctg     480
gtgggccggc tacggcgtgc gcccgtccac ggtggcgcg atctcggagc tcgggttcac       540
ggcgagcacg ctcctcggca tgacggagcg cgagctggac gacatgatgg ccgcgctcgc     600
```

```
ggggctgttc cgctgggacg tgctcctcgg cgagcgcttc ggcctccgcg ccgcgctgcg      660
cgccgagcgc ggccgcgtca tgtccctcgg cgcccgctgc ttccacgccg ggagcacctt      720
ggatgccgcg tcacaagaag gtacggcgta taggagtatg tactcgtgtc acacacatac      780
agacatactt gtatatatgc tcagtttttct tctgtagttc tgtactagtt ctgtgtgttt      840
tgcctctgcg agcaatgtga tgtgatgatg tggtcgctgg tcgatggtcg tgtgcatcgt      900
gcctgcgtta atgcatgcat gcatgcggac agtgtccatg catcagtctt tgttgggact      960
agagtcacgc gctctgctct gctcgcctgt gatgttactt gctcttgttc gatcataccg     1020
caaactcgca gcgctgtccg acgagcgcga cgccgcggcc agcggcggcg gcatggcaga     1080
aggcgaggcc ggcaggagga tggtgacgac gaccgccggc aagaagggca agaaaggggt     1140
cgttggcacg aggaagggca agaaggcgag gaggaagaag gagctgaggc cgctgaacgt     1200
gctggacgac gagaacgacg gggacgagta cggcggcggg tcggagtcga ccgagtcgtc     1260
cgcgggaggc tccggggaga ggcagcggga gcacccgttc gtggtcaccg agcccggcga     1320
ggtggcgagg gccaagaaga acgggctcga ctacctcttc cacctgtacg agcagtgccg     1380
cgtcttcctg ctccaggtgc agtccatcgc taagctgggc ggccacaaat cccctaccaa     1440
ggtacgcgcg cgcacacact taggggggtgt ttggttacac cccgctaaaa tttagctcat     1500
gtcccatcga atgtttaaac ctccgttccg gatattaaat gtagtcggat tataaaacta     1560
atttgtcagc cgaagattaa aagacgagac gaatctagtc cagttgattg ggtctatatt     1620
tcatactcct atttaaaagt caaacgcttg atgtgacccg agctaaactt tagcaggagc     1680
aaccaaacac ccccttattc atttagcaga gtaacatttt tacatataat atacaaacgg     1740
cagacgtttt ctgtatacga acaactgtcg tgaatgtacc aatctttta ggtcgttgac      1800 aagctataac aatataatgg taaagaaaat atagtggcac gcaaagcgcc aaagcccgct     1860
ctcattacct aggactagga ggaaggaagc agcaaaccct ttgtagtgga attctatatt     1920
tcctgcgccg ttaagtctat gctagtacat gtactacatc accatagtat atgcgggtcc     1980
tcaattcaag tactcgtaat gatcgtgtag cacttgtaca tacgtactgc tttaaagtat     2040
attttgcttg agacgcaccc gcactcgtgg ataaagcgag tgacgtgtca tcagtcgtcg     2100
gtgccaaagc ctggggtggc tttgtgtcgt cttgtccggc cctagggtca gacgggcatg     2160
catggcatcg acactctctc ggagtccgtg gctgtgtgct gttgccaccg gtttcgcgcg     2220
taccagtacg actgtacgag ccacgtgggc tcgatttgtg gcagtttggt ggccggcgta     2280
cgagtagtct cgtgctcgcc cccagtcttc agacggtgtg cgtcgaagtg aaatgaatgc     2340
acggtctggc ctggacggat tccagggtga ttggatatga tgatagcttg gtgacctact     2400
gacctgaccg ggacggccgc atcgatgcgc tcctgcgtct gcgtctgcgc caggctagcc     2460
cacccagatc cagaccgaga ccggccaggc gcgcgcagct tgttcgatcc gtgagcagct     2520
gctgctgctg ctgctgcgtg cgcacttgtg cgcgacgcga cacgacacga gcagcgagct     2580
gctctgcact gcactgcacg ggaaccaacc aaccatggct gatgagcgac atgttcgcgt     2640
ggcgcgcgcg atcgtgctcg tgctttgctt gcaggtgacc aaccaggtgt tccggtacgc     2700
gaacaagtgc ggggcgagct acatcaacaa gcccaagatg cggcactacg tgcactgcta     2760
cgcgctgcac tgcctggacg aggaggcctc caacgcgctg cgccgggcgt acaagtcccg     2820
cggcgagaac gtgggcgcct ggaggcaggc ctgctacgcg ccgctcgtcg agatcgccgc     2880
gcgccacggc ttcgacattg acgccgtctt cgccgcgcac ccgcgcctcg ccgtctggta     2940
```

| | |
|---|---|
| cgtgcccacc aggctgcgcc agctctgcca ccaggcgcgg gggagccacg cccacgctgc | 3000 |
| cgccggactc ccgccgcccc cgatgttcta gcgtgcgtcg tcgatgtgtg cctgcaccgt | 3060 |
| cgccgtacgt ctcacagttc ctttttcttt tagagtgtga accaccatgg aaaattggat | 3120 |
| tccctctcat atgatgttgc cacttctcag ttctcacttg tatgttgcgt tgcccggtta | 3180 |
| tagtcaggag tgggcttaga tttaggcact gtttagtttt aggactaaaa gctaaaaacc | 3240 |
| aaaccaaacc aaatgtttcc ggaagtaact ttttttaaa aaacgactttt ctcgcagtcc | 3300 |
| aaactgaaaa catggacctg cttttagcgg ctttcggatg gaaatgtgaa aacatatatc | 3360 |
| aaaaaaattt aacatatatt agtggttttcc accaaacggt ttttagttct ttaacggctc | 3420 |
| acaatccata atagttttttt catagtcaca accaaccaaa cagaacctaa attgcgcttg | 3480 |
| atacgccatg tttggactgt taggatttat gggcttggcc caattaagaa tttctaataa | 3540 |
| ttcgaggaaa atctcaaaag cccatataag tggatggcaa agggataggt ggaaccaata | 3600 |
| gtaccatatt gctagctctt gtggagtaga gctagcttaa atatggaagc cacactcact | 3660 |
| caccaagtca tggatgagag gagagagtgt ggagagccac acgcgcgcgc gctcggctcg | 3720 |
| cctcgcctgg cctggcctgg cctggcctgg ccggggcgaa gggcgcgggc gcacgacatg | 3780 |
| cgcgtgaatg gtc | 3793 |

<210> SEQ ID NO 32
<211> LENGTH: 7653
<212> TYPE: DNA
<213> ORGANISM: Zea mays
<220> FEATURE:
<221> NAME/KEY: misc_feature
<222> LOCATION: (75)..(174)
<223> OTHER INFORMATION: n is a, c, g, or t

<400> SEQUENCE: 32

| | |
|---|---|
| ttttcaactc tacaacaaaa gttattaagg gttcatgtag agaaaatgga cgaatctcta | 60 |
| gaaagtttaa tttcnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnggtgtt | 180 |
| tggtttgtag agtcaaaact cagttttaaa taccatggtt tacccaaaac tgcggtattt | 240 |
| ttggagtttt tgaaactcca ctcaggacct cagttttctt ctcttctctc tacatatgct | 300 |
| ttgtttttac aatagaacca aacagatctc ggttttgagc aatactgtag ttttattgtg | 360 |
| ataaagcaat accgtagtat ttatgtcatg tacaattgta aactatagta tctcaaaact | 420 |
| acagtatttt aaaactgcat tcccaaacag gccctcaatg ttcagacagt attttaagtt | 480 |
| ttggcgatct tattatatca cgtcatttgt ctgttcgaaa gaatcttgac tgcaaaatgt | 540 |
| cgccggtaag aatgccgtag tatttgaaga aaacacaggt tgagcaatac aaagcatagc | 600 |
| aaacatttct gtataacgac attgctttat ccagagaact ctataatgat tatattccat | 660 |
| tgattttgt atataacaaa ttatttacac ccattcagtt cctcacagtc ttgcccctag | 720 |
| tcaaaaatca aattttacct gttcggacca ccaaatcaat ggcaatttgg caatgggggg | 780 |
| agaaataatg caaaattcat ttgcttctgc ttagatttct ccccacccga ctataatgag | 840 |
| tggaaaaaaa ttctccttc agatcatctc tgtcatgcgc ccatggctgt ctgtcggtac | 900 |
| tgagaggcta aatggtaacg ctgttgggga cgccgcggca ggtgatgccc ggccccgacg | 960 |
| tgggcgccat gagctcgtac ggcagcacgc cagcgccgca ccggttgcgg cggccagtgt | 1020 |
| cagcgttgcg ccgttcgatc tcctcctcgg cgcggcgcac ctcgtccgcg aactcgcgcg | 1080 |
| cggccgccaa cgccgccggg tcggccgtcc acgcctcatc aggccgctcc ccgaggtact | 1140 |

```
gctcgtcggc ggagtgcgtg gacagcgtgt cgatgacggt catgaacgtg gtggtctgcg   1200
tcaggctggg cagcgccgac aggaagaagc ggtgcgggtc ggccaccagg tgcgcgtact   1260
ccgggtcgcc ctcggcgggc accagccgcc gcatcagcgg cggccggttc gggatgtagc   1320
cgcccagcgg gtactgcccg aagttgagcg ccgcgtgctg cgccgaggtg agccacagca   1380
gcgtcgtcag cagcgacgcc aggtccgcgg gcgtcgacag gcgcggccac cacggcgcgt   1440
cgcgcttgtc cgcgtgcccc gtgtgcacgg cctccctgta ccacgactgc agctcggtgt   1500
cgccctgcac ggactcgtcg gacgggtagt acatggccac gtaggcgtcg caccaccgcc   1560
tgatggccga ccagagcagc aacccgtcgg tggcgtacgg gtagtcctcg atgagcagcc   1620
ggagaccgtg cggctgcgtc gggtcctcca cggccattcc tctgtgacaa gggaacacca   1680
tgtcagcctg aatgcggctc gtatttccag ttttccatgc actgcattgc acgaagcact   1740
acaacttcat agatgttcca gttgatttgt gtaccttctg atgagatcgg cagggaggcc   1800
ctcctggtct agccgccaga gctcccggta cgcgaacgag ctcatctcca tgcagtagcg   1860
gccaggggtg aacccggact cgatgacgcc gtcgccgttg atgaggatct gccgcgccag   1920
cgcgttgatc ttgagcgtgt accgcatgtg aggcttgagc agcttgaaga tggggtgcat   1980
cgtgctcagg tgccggtgcg ccgcgatgat gaacggctcc atggccgcgt gcgtcctcag   2040
cctgcacacg cagcgcaatg attagtcgag gccaacactc cggttgctct gctctgcatc   2100
aacagacgat gatggaaatt gggaatgacc gaccgactgt gtcgccgcgt tcagaggtgc   2160
acataccagt ggttgatgag ctggtggacg ccggcgtcat ggagcagac gtgtgccttg   2220 gcgagctgcc acagccagtt gctggtggca tcggcgggcg gcgtgaacac ccgcttggcg   2280
cgcgcgcacc cgtcggtcat cggcggcagg cacagctcga tcgcgatggg cttcagcgtg   2340
cccgcggccg tcaggaagaa gagcgtgcgc gtgccgtagg ccttccgccc gtccagcgcg   2400
ttgatccggt ccaggaacgg catgaagatg tcgtggtagt ccagcatgta cagcctgtcg   2460
tcctgcagcg cctgctgcac cgacatgccg tcgagctgtc cgatgatgtg ctcctccgtg   2520
atggccgact ccggcgggcc gtacacggcc gggtccagct tgctcatcgg cgggaacgcc   2580
tgggagagac acgagaggaa cggacggcag tgagcgagcg gtaagcacgg cggcgtcttg   2640
acagcaacgg ctggggtcgt tgagcagcgg actcagtgtc cgcggcgtgt tgggcttgtg   2700
attgatatgt atacctgaag acgttcgatg ttgacgggg tgatgccagc cagcgcctgc   2760
ctcgcgaact cgtcgtcccg cagccaagca aacttgtcct ctgccacacg gaagggcgga   2820
aaaagaaaac agacgacagc atgagtacaa cattgtcgtg ccccgtatct tatcgtatcg   2880
gacctccatg gatcatggac ggaggaggag gaaggcgcat gggcgctggc ttactcttga   2940
tgatgtcgga agtgtcgtag cggaggaggc cctcgctgtt ctcctggatc ttgcgcacga   3000
agggatcttc tggaacagc tggtcctgca gggcctgctt caggcggagg ccctccttga   3060
agaggttgtc cacgtcgtgg aagcggcga agtcgcggat gtcaggcgac acggagctca   3120
ccagcagcgg catgaagtta tggagcagcg ccttgagcgc gccctccgac agcatctcgt   3180
tcttcccgtc ctcgaactcc tcgtcccggg acacgtagat gggctccggg tactccaccc   3240
ggctctccgc gcggtcgtct gcaagcgcca ccacgaggaa atgttagcct cggtcaacgt   3300
cgcccgcgat cgggtggttc cgatacgaaa gctacgcgcg acggcgacgg cgccctctcc   3360
gccatgcttg gtcgccactg ttgctgtcgc ggaatttata ggacagatgg cggtggtgac   3420
aagaactgaa cagggaaacg ggaaagcgga ggcttgcctg tgatggtctt gggccggccc   3480
```

```
gttcgcatcc gccgcgggta cggcagctgc tgctcgccgc cgaggaccgg gcgcgcgaac    3540
tcggcgccct tgtccgggtt gccgaggtcg ttgtacacgt catactccca cacccggtcg    3600
gtgatcctgc gctcgccggt gtcggcaccc tcgcccctca ggtcgctgag ctgctggcgg    3660
cggagctcct gcaggcccgg cggcgtctcg gccggcaggt acggcttgtt ggtgaagaac    3720
acgcgcgggt tgcggtccac gcgggtgggc tgcacccacg agttgcaggt gaagtgcgcg    3780
gggccggagg gaaagccctc caccacgatg ctctcgatga agaactcgcg ctggtgccgg    3840
ttgagcacgg tgaccgcgcc cggctcgccg aaggacccgt caacggtgaa gtccgccgtg    3900
tacaccaccc gctccgtctt gacgtccttc ttctcgaacc agcccaccag cgccgagcgc    3960
ctgctcttct tggggccccc ctttcctgcc accgattcaa cgatgattcg gtaagatcga    4020
tgcctcgcct ggcgtaattg cgtactaact ccatcttcgt ttcgacgcag acgagatggt    4080
aaagacggcg gctttgggca caaatcaaat attcaaatca agagagacag ctccacgtga    4140
tggtccattt ggaaatgatg actcggagac aaaggcacca gacgtcaagg cgcaccagct    4200
ggaatattct cgccgcgggt tccatgaagg tacgtggtgg tggtggcggt ggagcgaacg    4260
gagaagaaga gcggcgagtg aagaaaaggg aaagaaagaa agaaggaatc aatctatgct    4320
actgccagta caattcaaag atgcaacgca acgccggatg cgtcttggaa ttccatgcca    4380
tcgcgtggcg ggcggcgacg gggatggtgg aatcacggaa ctgtttctta cttgggtcgg    4440
tctccgtgct gatgagctcg aggaggacac tgccggcaac ccggtcggcg tacgcgtcca    4500
gctgctcggc gacccggcgc ttggcgtcct ccttccgcct ccgccgcacg gtgaccacgg    4560
cccgcgcggc cacgctctgg gggtgcggct ccggggggcc cgcccggcc ctctccggtg    4620 gcgccggcgt caccacgacc cgctcggcca gcgcgcccac cggcgcggtc gacctcagcg    4680
acgacctcct cctgtgcgcg ctcccctccc ttccgaccgc ggcgaagcag ggcccgcctc    4740
gccgctcccg tccgggcgcc gcggcagcag ggctcgccaa ggaagatctc cccagcagct    4800
tcatcgccga cgccatgggc agagctccag aaacttcctc ccccttgatc gaccgatcgt    4860
agcagttaag gttggctgac gcactgaaga acaaaacaac aaatcgccgg tggactagtt    4920
cgcggatcgt ttccgagtgt ttttttttct ctctttctct ctctccctct ctctcgttat    4980
ggtgctttgg actagtctct gtttgtgcag tggcgcgagc taccaccttg ctcgcggtgg    5040
gagcagcacc atatataggg gcgccggtct gggagtaagt gaggactcgc tggggcctgc    5100
agtcctgcac ggagcagcaa ccgacgcgac gagctcggct cggctggacg gacgcgcagg    5160
cgcggcgatg ggtattcctg cgccggccac acgtgttgca tgcgtcctat gcgaccggga    5220
aaaatagggg cggagctgcg gcctgcggga ccgatgcttc gacgcaggtg acgcggacaa    5280
cgatggcccg gccccggccc cggcgtgtgt ggttgctgat gcggacaacg atgccccgtg    5340
atgccgcgca ctactactgt atcagagatg ttgaagaatg aactcagggg ctgtttggtt    5400
tgtggctaaa cgtgtcacac tttgcctaag gttagtcgtt cgaattgaag aactaacctt    5460
aggcagaaaa gtgtggcaaa atgtggcaag ttagtcatca aaccaaacag gccctcaatg    5520
tgccgggtgc ccctaaagac gaggtactaa acaacgtact aggttgacag tggattggta    5580
tcgaaagtag cgcgcgtatc ttggatgcta acaatttgaa caacggttta tatgatagtc    5640
atataaatat taaaaatata tatcgtggac aataggaaag aatgacggtg caaacagggg    5700
ccgtaagtat aagttcaggg caggcaatag ggccatgcag cggaggcgat cgccgggggc    5760
ctcgccgggg gcccaagaaa gaaatgggct caatatctaa tataatagta gagttggtat    5820
taaattattg tcttactaag gccccgtttg attagaggga ctaatcttta gtccctcgtt    5880
```

```
tttagtctcg tttagtctct attttaccaa acgaaaggac taaaatagggg actaattggc    5940
tttagtctct agtccctcac atgagtgcta aatggactaa agggcaacat ttactccaat    6000
taccettgct agaaaattgg tgtcaaacaa aaaaagggc attttggtct ttatgtgttg     6060
catttaatgt atttagaatc tatttagtcc ctaaagccaa acaggttagg aactaaaatt    6120
tagtccctag actaaacttt agttatagga ctaatggaac caaacggggc ctaaattaca    6180
tatatgcgga acaaacgacg catatgtcta gctaaagcgt ccgttgaagg cctcctacac    6240
tgctacacag aaccagtctc gttctcactg tcgtcaccga tcgcatgtca cacgctcgta    6300
gcttaattag ttttatcgaa attataataa ttatcagaat ggaattcaat tccaactaaa    6360
caaacggagc ttagggaaa ttagtttatt ttcaaatgaa aaataggaat tccttagaga     6420
aatagggctg tcaaactaac actaaatata ttgtgatcga ctttatttct cgataattat    6480
cagacatatt aaattgaata tatatcaatg tatttgttta tgtctttgca agtaaaattc    6540
atacatatta tttaaatata aaattataa tagaaggtct atcacaatga gctcgtatgg     6600
ggccctcaaa atcataggac cagggttgta caagttatgc aagtgaccat tctggtcctt    6660
tagatcatga tctaaatata gattttacca taggcgtaac aatagtctgt taaggttta    6720
gggtttaggg gatagtgagt atggataata tgatttttt ttctttggtg ggtataatgt     6780
gcgtgcaccg gatatgtaac ccgctgccat ccctggcctt ggatggtgat ggtgacacat    6840
actatgcagt acggagtata tatgcgtgtg ggcacttggc cacgtagcga gcgtggtgac    6900
cgagatctcg tgtcgagacg ttgctgtcca cggcgatctc cgatccgcg gccggtggtg     6960
cgcagtaaac acacacacac acatccat ccctcttcct ctaaactaaa gcaaacattg       7020
atggccggtc cttttgtttc tcatcatcat ctccgaacac gacgttcttc ccatagttct    7080
cgctaagaaa aaaaagaag agagagagct ggccacgctc ggctgctcgc ggcgggaggg     7140
acgcgtataa gggcgatgca tgcgcgtgcg tgcaccgtgc agtgcatgtg ttgtttccgc    7200
ttcttctgca cgcggtgagc gatcgagata caatgcagta agtgggcctc gacgctgacg    7260
ggcggcgccc gctgcccgct agcgcgttga ccacccgtcg tccaccaacc tcctgccctg    7320
cccagcccag ctcccgatcg cttcttcttt cggcgcgtgg ggaggccggg ttagcttagc    7380
cccggtcgcg cgcacggccg tcaaagccgt gtaccggacc gatcgggcgg gcctgtcaac    7440
ctgtctgatt acacttgatc aggattcaga gttgagataa aaggaggccg cgcgcgcgct    7500
aaaagaaacg aaagagagag cggccgagaa agggaagcta aagaagaaa agcccgagca      7560
tctcctccat gcatgcacga gtatacatac aatggcagga tctacacagg atcatcggat    7620
caccggaatg gacagccctt ttgccaaaag ctt                                 7653
```

<210> SEQ ID NO 33
<211> LENGTH: 6081
<212> TYPE: DNA
<213> ORGANISM: Zea mays

<400> SEQUENCE: 33

```
aagaaaatac aaaaaactag agttaatgaa agatacaata aactcaggag tctcaactta      60
acttgaggag agagaaaata gattcattca tgactgagga cacatgatgc aagaagaggc    120
accatgatta agggtaagat ttcaaaataa ttacatattt aaatatatag agatgccatg    180
catggaaaaa atatatatat ggataaatat atattgtttt taaataaacg acaataagtt    240
ttgataaata gatataaact atatagtacc tattatatct attatgttag gaaataaata    300
```

```
aaaatataaa atatatattt gatacaaata tctttttatt agtgagacag ttttccattt      360
caaatcacaa gataatttga attttctaga tatatgcttg tactgtctaa atattacgca      420
acgcttacat ctttgttttt tagcacgagt gagcacagat cgatgggcta ctaaatgtaa      480
attgaacaaa tagaatgtaa attgagaaaa atagaaggat gagaagacta gagtctacaa      540
aggagaggac agtgtgagtc tgcaaagata gcgcggtgga gccgtgcagc gatagagaaa      600
gatctgttgg ttcgcatcaa tcgaagagat ccgacgaaat ctagcaactc gtgatgatat      660
gagatcagag tctctctccg aatatgcaga agtattgtaa agctgtacta ataacaatct      720
tattttaatg taagaacga gcgcatgacg aaccacgaat tgatagtccc ctgcatgccc       780
tttcccctcc cagcagtcct agctaagcct aagctagcta tagctccaag tttcaaagaa      840
acaagtagta ggaaacttca aaccaaaatc caaaagaaca cgactccaca cctgctgtgc      900
gcagcgtcta cgaaccaacg aacatcagct cacttttgct tctccaaagt caagtcccag      960
tccacttcac ttgcttcgcc tgcgcgtgca ggagcgagcg ctacggatct gtgaaaagct     1020
tggccgaagt cactactgcc tccgcgcttc tcgaagcgac gccacgccat gccgatcgtt     1080
gctgagctag gcgtcgcccg cctagctgca gctaggatcg gagccagcta gtcgtcgtag     1140
ccaagccgcc gcagctcgcc tgcgagcctg atgtctccct cctcctcctc ctcgtcgtgt     1200
tcggacggcg cgtgggtgga cgtagtggtc gacgacgcgc cgtccgcgga tgacgacggc     1260
gccggcatca gctcctgccc aagccggtcc acgctagccg cccggctctt gggaggcgac     1320
gacgcggacg acgccgcggg cgagcggccc acgatgggca ctggatccgt aagctccttg     1380
ccgtcgcgcg ccggcgagaa cgccacgggc aggtactcgt cgctgtcgca cgggaacttg     1440
gagttcttga agtgctcctt cagcgcttcc aggccctgcg ccgccgcaca attgtaacat     1500
tgacatgtga gcaataagta cgtacgtagc attaaaatgt cttcgacgga tgtagatgta     1560
ggagaagggc agctgcagga gtggagtacg tacttgtacg cgcgcgtatg tcacttggca     1620
gatcttgcgc gagttgtaca cctcccatgg ctgcttgtgg aacgccttgt acagccgcac     1680
ggcagcctcc ggcgatgtca ggttgacgaa gccgtagccc acattacact tgttgctgca     1740 ttttttttgtt ttttttcatt tttgcataag gaagaaaaat tctcatttca tgcaagggca    1800
agaaattcag aatggtaatg gcatggagga acaataacta aaaagacttg caatcaaaaa     1860
aaaactttgg cattatgctg cagctgcttt acacatgagt atgtttgaag ctgcatgcct     1920
tttgacagcc actaatgtcc tctcgtcatt gggcattgat aggtcttttc tcaaacttgc     1980
ttcgtgcaag agaaaagctg ccggcggtat atataaaagc aagtgcttta ataagcaaa     2040 cttgaaagca tacattttgt ttgcatatag aaaactactt tgatctgaag ttcaaatttt     2100
ctctttagaa cgaaagtgct gacttttttcc ccctttcat actcatgcaa ctctttttt     2160 ttcacagctc catctccata gctaagcgtc tatctctact gtctagtctc aacactacaa     2220
ccccatcggt gccgcacctt ttgtatgtgt tggcctcgtt atggaagtgc acggctgtgc     2280
aaagcaagaa aggcaggcag ggaggcgatc ccaggggcgg cagcagccgc gagaaaggaa     2340
ggcaggccgg ctccctcgcc atcggcagcg gcagcagcag ccagcagatg cgcgcatgca     2400
accaaagaat ccatgggggg gcatcaaaac gagaaggatc tggcatggtc ttgcttgccg     2460
ctgccaaatt tatttccatt tgggctagta acgccatagc ccatctatgc ctgctgcact     2520
gtactctacc cacccaaaga taagatacct cgatcctgaa gctcacgctt ccacagccag     2580
ctcctcgcct cccacccccc cgcccacatt tcccactcca accattattc aaggcaacaa     2640
attcccagga aaacaaccga attcaggctg ggaagcttgt gtgtgttctt gcattgggca     2700
```

```
ccataaaata taagtcaatg cgaacagcta aatgcaatta tgtgagaagg aagccgagcg    2760
cgcaactcac ttgaaatcta tggggaggta gacgaaatcg taggcggaga agggctgctc    2820
ctcgccgctc gccacgatcc actcgttgga ttggatgcag tggttgtcca gcatgttgag    2880
cagcagcttc tggctgcgac ccaaacgcct cgggcatcag ctagcagaat cgcaattctg    2940
tgcgtcgccc atgaaatata gcattgttgc aacaaacgtg gagattggca gggatacctg    3000
tacttgttcg gtatgttcct gatcatgacg gtggtcctcg tatccatctc cgaagccggc    3060
gttgcttgcg tgtcggcgcc gccgccggcc tcggctcct tgaacaggaa gcgcgcctcc    3120
cacccgctct ttcgtccttt ccagctcccg ccgccgctgc tcccgacgcc tttctgggtt    3180
tgcttcccgg acgctgtcgg ggtcgacgag gatgccgccg ccgccgccac cacgatcttg    3240
ccgcccttgg tcttgcgctc atggctcgtt ccggcattgc ctcccttgga cgactggtcg    3300
ctgcccgcgc tagacttaca ggagctcctc ctcagaagca ccactccttc cctcgccctt    3360
acggaaccgg acgacgacga ggatgccggc ggctgagacg acgtcggttg gacggtcgc    3420 cacgtcgctt gaagcctcgg cggagtcggc gcggtgggcc ggtgctggtg gggtgcgtac    3480
ccgcgcctag gaccgacagg cacacggcaa aaattcagcc gcccacaggg tgatgggaag    3540
gctagctgac tgaaattgcg ttgttgttta cctgcggggc ccggggccgg aagggcgcgt    3600
gaactcgacg acgaggcggc ggccgaaaag ctcctggccg ttgagctcgg cgagcgcgcg    3660
cgcggcgtcg cgcgtgtcga agaagtccac gaacttgtgg ctgggccgct gcgccgactc    3720
cctcacatcc ttcaagtccc ctgcgaacac gaggacgggc caatacaatt gctgcgggaa    3780
acacaagaaa cgagcgtggg aaaacgaaat gcctggttgg tcggctcggt cggtggcgcg    3840
taccgaaggc ctggaagact tggcggaggt cagcgaccga gacgccgggc aggggctca     3900 ggaccaccag ggagccgcgg ttgtcgccgt cgtcggcgcc ggtggcgaag tgggcccaca    3960
cggcgtgccc gaggacgagg ccgcggccgt cgtcgttggg gtggggccag tcccaggcct    4020
ggggcgtcgg tgcaggagcc cacgccgggg ctacggcggc cgccgcgtag agctgcccga    4080
ggcggctctg ctggcgcatg tgctgctcgc ggacacaggt caaggcgagc tcggcggcgc    4140
ggatgtcgaa gaaatggacg gtggccacgc cctcggacgc caccgcgcac gcgtcgaccg    4200 agccggatcgc gccgaatggc gccatcgcct gcgccacgtc ggcctcctgc gcgtgcggcg    4260
ggacaaggcc cagcaccacg acgcggctcg acgggccatt gaccaccggc gtcgtcgttg    4320
gcaaggtgta ccccggctgc ggcgccatgg ccatcgccat cggaggcact ggctgtaaca    4380
tggctatttg cggcggcgga ggcaccggca tggctggata tgggtggggg cagtatagct    4440
gttgcggaag cggctgtaga ggataggggg cacagaccgt agggtggaac tcctgagctg    4500
cggcatcgag aaggttaccc gtggcttccg ggaacccacc cattccactc cctcccccac    4560
cctccatggc tagagctcag aacaaaagaa accgaggagt ccaaggaaga ctgccgtcta    4620
aagatctaga actttctggt gattcttgat catgccttcg atcaagaacc aggcgagaat    4680
tgtacttggg accccgtctc agtctcactc tcccgttctc tctcctgctt agccgtatac    4740
tcggtgtgtg tgtgtggagt gagagcggtg gtagtaccgc accactgctg ccagaaacga    4800
gagagagggg ccggagagag gagagagatt gggagctctt tttatggtaa ttgccgcggg    4860
aaaagaaaac cggtgggtt ttatttggag ctctacaggg acaaggggg agagagacgc      4920 gaggagggag gggcggtgg agaagagtcg aggaggtgaa gggcgggcgg tacgagggaa    4980
agaggaggaa gaggagagac gagagtggcc gtgtgctgga ttgttttagc tcggatcctc    5040
```

```
tgcaacgaca gcacttgttg ctcttgcacg agtcatgccc cgtgcgtaca tgacaggccc    5100
cacgtctgct tctttgctgg ggagattttt ccggtagatt ttgcgtgttt gttttcggag    5160
ttagatctag cttttcgaga tgccgccggc tacaaataaa gaccatattc ttcaaattac    5220
tgggcgttcg gttaccggac taaaatattc gaatatcaat tataaagatt aatgttctgt    5280
ttaggagtgc tttattttaa gaattacaac tttagatttc tatcttcacc ataaatcaat    5340
ttcaatacat tggtaagaca gggttctggt gagcatcaaa taagggtcg acggtttgc     5400 gcgcgcagaa ccagttagaa ttctgagttt cttgctatag ttgttggcta gattcacaga    5460
attagctcga aaatatgtt tgtaacgggt ccagccccc tcctctataa atacagagga     5520
atacgaccga ttaaacacca tcaatcgaat caataccagt ttatctcgta tttatttctt    5580
gtatatttag gagtagttct agtttagcct tccaatcccc aaattctccg cttctcttcg    5640
actctatatc gataggagtc taggtcggcc tgccaagcct agacaacacc taggatctct    5700
cctccccgac ggggtccctc ccgggagcga gatccaggcg ccaccgacga ccttcgctgc    5760
ccctgcacac gtgcggaccg tccggcctat aggcgcggat cgtccgaccg tcaagcagga    5820
aaccctaagc cctgcgccag gtcgcagacc gtccggcccc tggccgcgga ccgtccgcgc    5880
ctgtgcagtg agcaccgccg ccggttctca cgcagtgatt ggcactcaga aaaagcgcca    5940
acacactttt tggtgacccc gctggggacg acacatatag acccatcaaa tcggccctca    6000
atggccgatt caagggatag ttctgaagtc tcccccagca atatcataga gtcgacttgg    6060
gaaaccttgc cggctgacga a                                              6081

<210> SEQ ID NO 34
<211> LENGTH: 3369
<212> TYPE: DNA
<213> ORGANISM: Zea mays
<220> FEATURE:
<221> NAME/KEY: misc_feature
<222> LOCATION: (2428)..(2527)
<223> OTHER INFORMATION: n is a, c, g, or t

<400> SEQUENCE: 34
aaaagttatg caactttata gttggtcaca ttttcaaatg aactcattta gtgccttaaa      60
taatcaaatt actctcgatt tgttatagta catggggaat ggaaacgtaa tataaacata     120
attggtgtag tagtgtagtg gtataggagg gtatgcgcga gagagaggtt gcgagttcga     180
atctcaccat ttacaaaaac atataagttt gattcaaaat gatagggcaa cgggtaaggt     240
aatagggtag ggttggagag ttgttcctag aatttaaaaa atgttttgct gttttttttt     300 tatttttcg attcttaatt tgccgagtgt ttttctttgc cgaatgcttt ttgacactcg      360
gcaaagtctt tgccgagtgc ccgaaaaaaa cactcggcaa agaaccctt gccgatgaaa     420 tctttgtcga gtgttctttg ccgagtgtta cactcggcaa agcctttgcc gagtgtaaaa     480 tagccttgc cgagtgtttt agacactcgg caaagaacgc gattccggta gtgttgggca     540
aacaaaaacc aatgtcgtca tgtacacgct ggtaccttgt gaagagatgg gatatatata     600
accacttgca tcggttgtgt tacttctgta cactaacaca cagtgacaca cacacacggg     660
gggttcccgc ggggtcaaaa cgagtcagac gacagcactg ttacatcgga gcacgacggg     720
tcttgtggcc gtgtccgtcc actgacggtg tatatccctg gcgatgttga gggcgtcggc     780
cgaggcgccc agcagccccc gctgcgagaa gccgacggcg tagagccgt tcttcccttt     840 ccagccgttg gggaagggga tcctgggcat cccttcgctc gtgaacacgt cgcctccgtc    900
ctgcaaaagc agcagcgtgc gtaagactgg gctaggggac tccggcccgg cgccaaggca    960
```

```
gccgacgact gctgctccct gtgggcgagg gacacttcgc ggcgaaagga gctatagctg    1020
cccctgcgag ccccggcccc ggcatacacg agaatggcaa cggggcaggg tgacgacatg    1080
gcgcgctgca gcgcgggcag aggaaggaag tgggttgggt ttttaccttg agccaggacg    1140
gcacgttgct cctgtacccc gtggcctgta tgattgcgtc gaactgctcc tccttgccgt    1200
ccgcgaacct gaccccgcgc tgggtcacct ccttcactgc tcccactacc tggcgatcac    1260
gtttcgcgtc agcccacag ccatttcctt cccccattat tgtgtaaata aaataaaacg     1320
cagaagcgag cgagccttaa ctcctgccat gccatggcat gccagacggc tcattcatgt    1380
gtgatttcta caactgcacg cgccgctcct ttggtgaaag caggctgggg gcaatggcac    1440
taaccttaat tttgccggtt ttgatgtggg ctagcgtccc gacgtccagc acggggtcc     1500 tgccggtgag gttcttcagc tcgatgggcc cgtcttggg ccgcctcagg ccgagcttgc     1560
ccgtgtcgcc caacgccagc cgcgccgccg ccaggaggat ccggtccacc acccggacgg    1620
ggagcagctt cagcagcgcc atggcgatgc cgaacgtcga gagacccagc atctccctcg    1680
gcagcacatg gacctgcgtg tgtactcggt cagatctcgt gtgtgtgtgt gtgtgtgtgg    1740
ttcaagcgag cgaaagacga tcatcgttgt tgtatactac atgtttggcc gaacagggca    1800
tatctagtat tatgggatgg gtgccgacga cgacatggga caacaagatc gccgcaaaac    1860
caagtgcaaa agtgctcgat cgagcacgac ggccacaaaa cacgcggcac ttgtactttg    1920
gatgtccaaa gcaagacaaa aaaaggagag agtagtagt agtagaaaag gacgggccca     1980
aagcaagcca agcagtaaca acatgtccgc cgccgctctg ggaggagggg atcattcatt    2040
agttagttac cgtgttgcgc accaccatcg acggcgcggc gccgtggcgg cacaaatcca    2100
ggctgacctc catgccggag ttgccgcacc cgaccaccag caccttcctc cccgcgaact    2160
cctccccgga cctgtagtcg cacgtgtgca ggacgcggcc ggcgaagcgc gcggcgccgg    2220
gcaggtcggg caggcgcggc acggcgttct cgcccgtggc cacgacgagc cagcgcgcca    2280
ggagcaggtc gccggcgccg ccgccgccag cgcccgccag gcggagcgcc caggcgccgg    2340
cgcccgcgtc gaacgcggcc tcctccacgc gggcgccgaa ccgcggcgcc acgcccgccg    2400
ccgcggcgta cgcctccagg tacgccannn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnatt atttaaattt taagttagaa accatatggt ttaccaaata tacctatcaa    2580
tttcttttat tagaaaaagt atgagtgtct agtttaaatc attttacat tattataaat     2640 tctactattt cggttttctc ctttcttttc tagatagaaa ttatacgtat aactaaaaat    2700
tgtttattta attcatctaa cattaatata ctaagaatta attgtaaatt actaaatggg    2760
acttttaata accaattcat ggttattatg acataaataa acattttact attctaagta    2820
cttaagtgct atacttatga atatatttat tatgaatagt aaaatctata ttttcattcg    2880
accgaaaata cgtggcttaa gatttctatt tctttatgca aataagtgta cacttaaaat    2940
actactaaca attatcatta cacatatatt aaagctaaat taattataaa catttctagt    3000
atgaaaacca cgtgaacaat cgtaaatact aactttgaag tatttagaac agacgtatga    3060
aactaataaa acaattgcta gtagatttaa aaataaaaat catcacaaga gattacgtga    3120
atttgtgcct agactttaga gagtagcaca aattttcacc ttcttgatct cacgttcgtt    3180
gtagaattcg ttgtagaata aggagctgtg cttcggaca cggtgttgac gagttcagca     3240
acaaggtgat gtcacggcgc ggaataggaa gcgacgacgc agaggcaagc atgttctgcg    3300
```

```
aagcggagaa cgatgacggc aagcatcacg cgtagtgcag aagaaacaaa gaactcggcg    3360
tcgtggtga                                                             3369

<210> SEQ ID NO 35
<211> LENGTH: 11305
<212> TYPE: DNA
<213> ORGANISM: Zea mays

<400> SEQUENCE: 35
attgcatgga acaagatcat gacaaaagat aatatatctg acttcgtcgt tagatttatt      60
tagcctaaat cttgaacaaa ctaactagat ctaaaaacta cgaatgaaag atatatattg     120
gatctccttt cttcttacac acatgcgatg cacctgacga aggaagaagg aaagaggcca     180
ggacgacagg agcaagtgcg ctgatggcgg caggcaatac gcggccgcgc cctgctagct     240
acttcgtttt tagtcacact gcaagctagc tcgatgtgac tgcagacagt aatggctacc     300
agcttgattg gcaccggtaa taagtttata acaccagag gctgaatccc aaatcctact      360
acgcagctaa tcacgctcac aattaattgt tctagctcta tagcgcactg tagctagcaa     420
cactagtcgt actacactac tactagctat gactactatc caaacgagag atgcagaaag     480
cgatgaagga gccattaacg gcccagactt tctttcatca tatcagcagg tctgtcaaca     540
atcgacagcg cgaatgctct ctctctcagt ctctcgttgt cggggttcc  gaaagggaaa     600 gcgaccaact gaagctgaag cgcgcgtcgt tgtctccggc cggcgctgct gtcgccgccc     660
atcaccagcg acatcaaggc cggcacgcca cagagaattg aaggccgggc gggcttcatg     720
aaatcatcgc cagccgcaac agtcgccacc actcacaagc gcccaagctt acgtgaactc     780
tacgtgaaca catctgatcg acgatgccta accaattaat tgccccaccc atcccaaata     840
catgttgatt tcttacaaaa aaaaattgag tatactactc ttataaacac gtaccatcaa     900
tgaaataccg atgatgaggc tatgatcgat gttgaagttg acagaaccac ataaagctaa     960
aactaaaacc atgactcgat cgagcgcagt ggtcccgcgc gcgtgtgcat gcatgcgcca    1020
aggcaaaatc tctgtgtcgt gtctcgtatt catccgatca tcatatatat catctccgtc    1080
tctctcgctt tcactctctc ggcgcaaatt aaagcaagca atccatcgaa cagtcagtca    1140
gatcgggcca tcgtcgttga tggcgacgcg acagcccggg tcacgttcac gacacctcac    1200
tgtagtactg tgcactgtta ctgtcgtcga tctcggccgc tagcgctagc tcgatcggta    1260
cgtttcggcg cccataagga accgagagat tattggggc  gcgccgggcc gtcagagcag    1320
agcagagcag atcttcgtgt ttaattttat cgcctgtaca tgcatgtatc cagaacaagg    1380
acaagctcat gtgtcgctgt cagcgctaac tagctacagt agcttgatat ataatggtga    1440
tcgagattat tgatcggttt ccttctgctg aggttttctt ttcttttaca tgcacctacc    1500
tctctgctag ctttgcattg ggacgtacgc agaaaaattt caaaggaata tatatatata    1560
tatatgtagg gttttcatat aaatcagttt atttaacttt gccaccacag caacaactag    1620
atccttaggg taggtacaat gagtgtctta agttgtgtct tagagtgtgt ctagtgggtg    1680
aatataaaaa attcaagaca tgtatcttga cgaagacaca acgtcttagc tttatgttcg    1740
agacaggaga ctagctgatt ggtcatttta atttattgaa tgctatggtt ggtacaatga    1800
atatggtaag acacatgttt tagacattac cactgtattt gtgttgtgtt ttagttgtgt    1860
cttatacttg gagtaccgtc cagcagtgtc taggttgtac attctcttac tgttatagtc    1920
tgttacctgt ggcctatact gacgagctat agcctgccaa atcattaata atagaaccca    1980
gtcagatgtg catgtaatta acgacgagct taaattgcgt gcagagaaaa aaagggcaat    2040
```

```
tgcacagagg accactaaaa agggcagaat agtcctgtgt agatgatgcc gctggatcga   2100
tggattcaca tataatgcct gcaggccgca gctcagtcgt cagggccggg ccggcgtcga   2160
cgtacgtacg agtagtacta tactatatac tatatactcc gtggtccgtg tggaggccgg   2220
attcgcattc cgatcttgca tggaatcttg gtacatacta cgtcgtagcg cttctccttc   2280
ttcgtcgtcc cagaggcgta ggtacgtacg tacgtacgtt cttgcattgc attgcattgc   2340
attgcgttgc atggcaaaag gtggtcgatc tcgatcgtca ttatgttatg ggtgtgttcc   2400
ccggactgtc ctcgtcgtcg tccttgccaa cagaacggca ctgtgcttgt ctctgcattg   2460
cattgattgc gtcggccggc cggccgggac gatgagttta agttcgatgt tcatggttgg   2520
ttgttcgacg ccctgcagcg gtaggagtat acatctcgtt tgttgtctcg aagacacaca   2580
caggcactcg caaatcccaa gcttgagcac tccttcttcc tgcctcgatc gtccctctcg   2640
tgtagattgg cgcgcgtaac acgttgactc ttcgccagtg acgtcacgca cggccgcatg   2700
cactcgggtc gtacggcctt tctgcccgct tggacgtacg tacgtgcatg cgtgatacgg   2760
ccggccggag accccatcga tgatcgatcc caggcccact ggcctgtacg tcctcctcgt   2820
cagtcgtagc cccgcccgga ccggcccac tggccactac tggacccat gcctgtgacc   2880 gtcaggccgt aaagaagtcg tcacgccggc cggcggccca cctgatgatg acacacatat   2940
acatggtgga gtggtcatga tgatgagctg catgcatggc gcgcgtcgta cgtacacacc   3000
aacacaacga cgacgcaacg caacgcaacg caacgcaaag ccgcatagca tgcagcgcgc   3060
ggctccacat cgccacgcgc ctatacaagg ttggccaatt cccatgacgc tacggctacg   3120
caccagagtg cagtaccacc gccgcactac cacaccgcaa actttctcga tcagtactgg   3180
gactgggacg cgatcgagcg agcgagctag aaagagcaag gcgacaagcg ccacgtcact   3240
caagggtcat tttcctattt cctgttcccc agctgagcta tagctcccac agggacagtc   3300
ccacccaaaa cgtaccaatc gtgtgccatc gcgtcttttt ctcttccatt tttttttcctt   3360 acaaaaatcg cttatattat attattggca cgaaaactac tcagatgaac tcctcagcag   3420
ctgtagcctc tctctctctc tctctctctc tctcacttttt ttctttaaaa ttatctgtac   3480
gtacgtagat ataaatatag ctatgttacc actactagtg acacactaga cgtgttggtc   3540
tgtgctgtac ggagaacgaa ggtataaaca aatgcgttgc aaaagcgcag ttcgacgacg   3600
atagatgtat atgtatactc cacaaaagcc cgagctgtct tttgtttttg gagaaaaaaa   3660
taaataacgt gtggttcagg aacaaaagct agcggggttg ctactaattg ctactgttgt   3720
tgataaacac gtcctgatca gacgccactt gcttggatct gttttaataa taataataat   3780
aataataata ataatattat tattattatt attattatta tttcctttgc tttctttttt   3840
tgaactgatt cttttgtatg ttgcaataat aatgttaaaa gacaaaagta acggcaggga   3900
gttgcagata gacctaatat caaaggctgt cagggccctt ttggaacgca gggattttca   3960
cttcacaggt gcttttttt atgaaaatga accggttctt atgatttctt tttttctatg   4020
tttcatcata cgagtggaac tcgaacatcc atcccaaata ttagaagaca aaagtaacag   4080
taggagagct gagaagcctg agatagaccc aatatcaatt aattaaagac ttttatagca   4140
aatccaaaag gatgcaaaaa caccccgtc aaaaaaataa ttattaggga caggttacat   4200 tttttggag gcaaatatgg tgcatacttc aacagtttta ttcaaaacaa aggctaaaag   4260
accgtaaacc gagcctatat ttttttaaa aaaactagat ccatctgccc cattccgcaa   4320
acgattgggg agacactacg tcgctcaaat atgtgggggt gggggggggg gataggttga   4380
```

-continued

| | | | | |
|---|---|---|---|---|
| aagcgggtta | ccgtatttt | ccaacaatga | tggatccgtc | gggctgattt ggtgacaagg | 4440 |
| ggatcccgga | aggattgaag | agaattgagg | ggaaaatgaa | ctaatttccc tctccattat | 4500 |
| ctcgggatcc | agggtcacca | aatcaactct | aaatctgttt | ttcggttgt tttaagtgct | 4560 |
| tttggagtta | ctcttatacg | aatttgagtc | attttttttt | aaaaaaaga taaatcaaaa | 4620 |
| tatacattag | tctgtacata | gagtgactgc | tctgaaaaaa | ataaaaaac tgtagagaca | 4680 |
| ccttagcccc | aataattgta | gcacaggcaa | caggtgcaca | gcaacata gcccattgc | 4740 |
| atgcatggct | gcagtgtgac | acatggcggt | ggggccctgc | ccactgttcc tccttcaggg | 4800 |
| acggaaaggt | tggttgcggc | cccaccatgg | cgccaagtaa | tatcgccgct gctctctctc | 4860 |
| tctcttttca | tgcacacgct | cctctctccc | tccctcccac | cattgctaca gtcgcagctg | 4920 |
| tctgtgtctg | caaagtactg | actgctccca | ctccactcca | cccccagttc cgggccactc | 4980 |
| gggcatcgtt | tctgttgctg | caaatctttg | ttggctgctg | ctgccttgct atctatctat | 5040 |
| acaccgcccg | caccttccat | tcctcctcct | ccgaagcagc | aggcagcagc tgcatcgcac | 5100 |
| ctcacacctc | tcgtgtccat | cgatccagcc | gccgccgcag | ctgcagctct cacttcactg | 5160 |
| ttgctgtgcc | acctcctcgt | cgcctgtagt | gtctgtcgat | agataaacgc ccgcggaatg | 5220 |
| agagggaagg | agcggaagct | gcagcgggcg | cgcgcgtgca | agggctagga ctagcggttg | 5280 |
| caacgtcggc | gcgcgcggcg | tacgtcgggc | atggattggg | atctcaacgc ggcgggcgcg | 5340 |
| tgggacctcg | cggagctgga | gcgggaccac | gcggccgcgg | cgccgtcgtc ggggggccac | 5400 |
| gccgccaatg | ctgccgcggc | gggcacgggg | acggagagcc | gcccgccggc gcccggggca | 5460 |
| gcaggggcac | ccgccgagtg | ctccgtggac | ctgaagctgg | gcgggatggg cgagtgcgag | 5520 |
| cccggcgcgg | cccgcaggga | gagggaggcc | gcggcggggg | cggcgaagcg gccgcgcccc | 5580 |
| gccgggcccg | gcgggcagca | gcagcagcag | cagtgcccgt | cgtgcgcggt ggacgggtgc | 5640 |
| agggcggacc | tgggcaagtg | ccgcgactac | caccggcggc | acaaggtgtg cgaggcgcac | 5700 |
| tccaagaccc | ccgtcgtcgt | cgtcgccggc | cgcgagatgc | gcttctgcca gcagtgcagc | 5760 |
| aggtagtatc | cccgccttct | ttcccatgg | ggggctggtg | tagtgtagtg tagctcgtcc | 5820 |
| ctgtctcgtt | tcaaggatgc | acaactttac | cttttccggc | ttgccttttt ttttttcgtt | 5880 |
| atctttttc | tctctctctt | tttcctgaaa | accaaagaga | tgaaaacct tcatctcgtt | 5940 |
| cgttcgtttc | ctcctgtagc | tacggtacct | gaattattgg | cacgccttt tccttttctcc | 6000 |
| cggcctcctc | ctgcgctcgc | tgctgctgct | gcacactgct | ctcaggcagg cctagcgttc | 6060 |
| gtttccttca | ctttctctga | cgccctgatg | cgaattaaca | tctgctgctc cccaatcgtc | 6120 |
| tgctcaagat | tcagcccgct | gccacggaca | cgtgagctcc | tgcgcttgct tttccgagcg | 6180 |
| gtttcttgct | ttcacgccct | tggcggcga | cgggacggga | tgccccccc cccccccc | 6240 |
| cggtactctg | ccattggctc | ctcctctagt | cggcgctgct | tgcttcccgg cgacagttcg | 6300 |
| ccaccgccgc | agatgaagcg | ccgccacggtt | tggcgtgcc | gcgttgagcg agacaggggt | 6360 |
| gtactcccag | ctttggctac | catcaatcat | ttgatgttta | ggtgccgcgt tgtgagctgt | 6420 |
| actgctacag | tatctctgca | gaatgtattc | tgtagtagta | tgaaaaggta aggcggcgt | 6480 |
| actgctatag | tatctctgca | gaatgttcgg | aggagtacac | caactgaaag aggtttagga | 6540 |
| aaattgcatc | gtggatctag | aattctagat | gcagtagtgt | agcctacagt agccctgtac | 6600 |
| acacataaag | gcattttct | tataaaattg | tctcgcaaaa | tgggattttt ttgtgctaat | 6660 |
| tatagggtgc | tttagcgcca | cctgggccgt | ataggatgct | ttagcgcaac atttctgaac | 6720 |
| aaccctatgc | agcttccata | gaccaccaca | ggcattcccg | catgcagttt gctctaaatg | 6780 |

```
cctcctttc   attttttacta  tccctgaacg  acgacccatc  catttctttt  tccgtctcag   6840
ggaagtagcc  attaaatgct  agcagtcttt  ttttaaagta  tcgcttggtt  tgagatgtta   6900
ttaggcccgg  tttggttgga  aaaaccgctc  cattttaatc  tcctttagtt  tgtaaattac   6960
agtactaaac  tgttttagtc  tttagtatct  cgaggagtga  ctaaaagaga  ctaaaccata   7020
taaatttcac  cttttatctc  ccatttattt  cagttacact  aatgacggga  gaatgctaaa   7080 gtgtattta   gtcatcttat  aattgattta  gtgtgtttta  aatacttcct  tagtctataa   7140
aattaaacag  gatataggct  aaactttagt  tggactaaac  catataaatt  tcgtctggtg   7200
aagtttacgg  cagtacagcg  ctgtgttggc  gcccagtttt  gtcttgctca  tatggacagc   7260
agagacaggt  cccgctctcc  tgtggtggac  ctaaacctaa  acagcgtagg  ttcagatcgt   7320
tcctggagcg  atcgacgctg  tggcaagcga  tcctaatgcg  atgctctggt  gacatgtcct   7380
gtttctgttt  acgccggaac  atcttgctcg  gtggggacaa  ttctcaatca  ttgatcactt   7440
tgtcttctgc  tttaaattgc  agactttgta  ggttaatagt  aagttgtcag  ccagtgagcc   7500
aacagattct  cagctttctg  tttaccgtct  gtgtggtcca  ggcttgacag  gtcttatagt   7560
attttcctgt  ctctaataag  catggacaag  gaacattggt  ccctggtgtg  atgtgtatta   7620
actataacaa  gcatgtatgt  gcgccacagt  acattaacta  ttctgacaat  aattacgttg   7680
ctgtttcttc  agtgaggacc  atcttagcat  accgttggat  catgtgccca  ccctactacc   7740
taggaccatc  tattcttcta  aaaaaaactg  agtatcttat  acttgtttag  aattatccta   7800
attcaaagaa  tcctgtggtc  ctaatcgatt  atgccatcat  tcattggtca  gcatattaca   7860
ctgcaacttt  ctcgtttgcc  cgtactcgaa  ttcagttgtc  tgatcaagag  ttttttttt    7920 gtttttgtt   tatgtaggtt  ccatctactt  gcggagttcg  acgccgacaa  gcgcagctgc   7980
agaaagcgtc  tggacgggca  caatcgccgc  cgcaggaagc  cacagccaga  caccatggct   8040
tctgctagct  ttatcgcaag  ccagcaaggt  cattttcgta  ctcaccaatt  ttgctttggt   8100 ttttttctc   cccaagtctg  tacttggttc  gaatacatct  acattgtttc  catcttgctg   8160
gtgctggaca  aagaaaaggt  aaaacgtcag  aacagatctg  tgcacacata  aaccatgaga   8220
agtaaaagac  tgctctgtta  aacttgtaga  gcttgcgtag  catttcagca  tgtttcagaa   8280
ctagaattcg  gttcataaga  taagatgcta  ctctagcatc  cctgcataca  ttagttgcga   8340
caagacgaag  attacattgt  tgacgcatca  agttattatg  aacctcttct  gtttctgtca   8400
attgtgtcct  catatttagt  gcaaggtctt  gctaatgcct  ttaagttaaa  aaagattagt   8460
atactgtatg  tttctttgcc  tttcagatgt  gttctagtac  aaaactacttg  tatgcttcac  8520 cacttgtaga  ttggcatgta  tatgagtctc  aaacttccaa  cacaattgcc  agcagattgg   8580
catatagaac  tgcaataaaa  attctgattc  acattgtatg  aaacggcgca  cagaatcaat   8640
ttatcagtta  tgtcacctga  tcgacatttc  ttcccaattg  atcaggcacg  cgattctcac   8700
catttgcgca  tccaagactg  gaggcgagct  ggccgccggg  ggtgatgaaa  accgaggaga   8760
gtccatatca  catcactcac  caaatccctc  tgggctccag  cagcagcagc  aggcagcagc   8820
atttcgtggc  tctgggagcc  gccacgcctg  cctacgccaa  ggaaggccgg  cgcttcccct   8880
tcctgcagga  gggcgagata  agcttcgcca  ccggcgtggt  gctggagccg  ccggcggcg   8940 ctccagcgtg  ccagccgctc  tcaggacgg   gagcaccatc  cgagagcagc  ggcgccggcg   9000
gcagtaagat  gttctccgat  cagggctgg   ctcgcgtgct  cgactcggac  tgtgctctct   9060
ctcttctgtc  agcgccggcc  aactcctccg  gcatcgacgt  cagcaggatg  gtccgcccga   9120
```

```
ctgaacacgt ccccatggcc cagcagcccg tggtcccggg cctgcagttc ggcagcgcgt      9180
cgtggttccc gcgcccccag gcttccacgg gcggctcctt cgtcccctcc tgccccgccg      9240
cggtggaggg cgagcagcag ctgaacgccg tgctgggccc aacgacagc gaggtgagca       9300 tgaactacgg cgggatgttc cacgtcggcg gcggcagcgg cggcggcgag ggctcctcgg      9360
acggcggcac ctcgtcgtcg atgcccttct cgtggcagta gtcgtcgtca cttgtcagca      9420
gccgctgcgt tctctcatct ttcgcgcttc agacgatctg gtagggagat actggcttta     9480
gtgatcactg atcagcattg atttctgttc tttttcctgc attcgctttg ttgaatcggc     9540
tctgctcgcc agcattcgtg tggacatttt ttgaacataa ttctgtgttc gtttccctca     9600
cattatcttt gctacggtga cacctgccgg ctgctgaccg tagcatgttc cttctcttgt     9660
gacttgttct cgagacgtcc atttgatgca gggcgcatcc agaattttc agttgcagtg      9720 cagacgcaat ccgatgcgtt tgaagatgac gggcatgttt ggttcacggc taactgtgtc     9780
atacttcgac taaagttagt cgtccaaatt gaagaactaa ctcaggcaga aaagttagat     9840
aaaatgtggt aagttaggta gtaaaccaaa cagacccgac aactgaggac ttgttcggtt     9900
tgaaggggtt taggggatt agaggggatt caatccctt ctatacaaat ttatatagaa       9960
ggggattgaa tcccctccaa tccctcaat ccatccctaa ccgaacaggg cctgaacggg     10020
ctcgccacat gtaggcatga agaatagctt gctaaatctg ctaaaaagt aattgattgg    10080 taattcgtcc tcattaccct agtaaaaaag gggacaaaat acgtaggtgc cgcggcatca    10140
ggattgctgg aggtagcaga gcacagaacg tgatgagttc ctgcaaggag tcgtgaatag    10200
cccctatctc gatctccgat tctccacggt aaattcctcc attagataat atcgatgaga    10260 aagttttct ccccacccac gagaatgtaa ataagaaaa aaattctcca ccgacaatta     10320
aatgaggacg agaataagga agcatttcta accctgtttc ttgcggggac ccgttaaact    10380
tacatataat gatgttttta tataatagtt aataataaaa ataaataatt atcttgtcaa    10440
gagatcattc attataaatg tgctcatttt gatgtaaaca taatgattat cttacatctg    10500
acaatatgaa gtgacaatgc tttgcatcaa taacaaaaa gtatgtccta attataattt     10560
aagcgggggc ggaaaatagg gatgaggaag aaataccccag taagctttcg tgaccatcct   10620
cgtgggaaac tttattttgt cgcagggata agaatagaga gctaaacccg atagagaatt    10680
tcccgttgcc atccctagtc atgcgggggt tgcgttgccc atcctatagc tccatgctgg    10740
agataattca tactgccgcc ggcattgaaa cacaatcgtt ttggacatga atccgtgtat    10800
accaggagtg attaattaaa agtcatattt ccaattaatt atacccatat tatatatata    10860
tatatatgct tggttgtcat tgttattgaa ttgtctctat gattgcagct ggtcaacaac    10920
attgctctct atcatgccca cccaagtttg attcttgtgg cttcctattt tttacatgga   10980
ctctgtatat ttttttcatc ttttcaagtt cgattcttgt ggcctcctat tttttacatg   11040
gacgctgcat attttttttc atcttttcat tcttgtgtgg cctcctattt ttaggcatgt   11100
tttgcctcac tcgtcgtagt ttgccatgcc tagagttagg tttccatctt ttcattcttg   11160
tgggatatgg cctcctttt cgggcaagtt tggttcgctg cctcatttac catagttttc    11220
cacggttaaa gttgggcagg tttgactgaa ttagacgtgt gtttggtttg tagccatagt   11280
tgtggcaaga ttttctcct tctat                                          11305
```

<210> SEQ ID NO 36
<211> LENGTH: 4113
<212> TYPE: DNA
<213> ORGANISM: Zea mays

```
<400> SEQUENCE: 36
ttgtggtgtt gaaaacagga cgaataaaag aaagagaata cttgctcttt tagaggtttt      60
ttaagagacc ttttagagt attattggga atgttaggag ttaatgagta taatgttttg     120
agcatatttt gacacctaca agtaattttt tctatatcct tctttatgat atactatact    180
tgaaagaaga ttgaattaaa actaaaatct ctctctcaag ttgaattgtt gtgccacatc    240
tttcactaat ttataattaa agggtctcat atttttgta cttttttata attatattta     300
attgtaaatc tcataaaata ttgttagctc gtgtcatcaa atcactaaaa tccataaata    360
ggattgatgc acttagctct ttaaaatgaa aaaggtacaa aaatataaaa aaaatcgtga    420
acccccaat caatttctaa ttgcattgtg aaaacttcga caacaaaaat ataagatacc     480
accaaaataa aatagtatca aacaatatca tcctctattt caaacttctt tatgcaagca    540
gcgtcattca caatttcgcg tcctctattt tacacactgt actgcagaca accttaacat    600
ctatgttggt tgtatcacat attttttgttg tagaaaattt ccaaagcaca tttaaacttg    660
attaaaatat tttggggtt taacgatatt tttttattat tctagaacta aatatatttt    720
taaagcttat agatatattt tcgcgggctc taaatacttt tttctccggt cccaatctat    780
ttctaatatt tttgaacttt ttatatactt tcaatgtttt aaataaactt tttccgattt    840
tcttagtaaa aagttgaaac catcctaaaa taaaaactat ttctaaccat ggtagagagc    900
taatttaagc ggctttaaga tttgaagaag aaattgcctt attttagagt tcattcaaga    960
aggaaaaaat ggagtcctag ttgagggaaa acaccacaga ttccacagcc ttcgcctgtt   1020
cgccaccttt cctccaaaat tgacccaca cgcggcgacg cccgaggccc cgagcgacca   1080
catcctccgc ggccgcggcg acgcccgagg cctgcaaaac cctaaccact caggttctgc   1140
cggccaccgc caccaccacc accagtccac caccatgctg acagccactc ccctaccca    1200
tcagctcctg gccaccttcc tcctcgtcct ggcgtcggcg acccaacctg cagtccctgc   1260
ctccaccgac cgcgcagcgc ttctcgcctt ccgcgcgtcc ctgtcgccgc cctcccgcgc   1320
cgcgctatcc tcgtggagcg gcccgctctc gccatcctgg ctcggcgtgt cgctccaccc   1380
cgccacggcg ccagcccctt cggtcaccac tccctccgtt gccgaactct cgctccgggg   1440
cctcaacctc acgggcgtga tccccgcggc gccgctcgcg ctcctccgac gtctccggac   1500
gctcgacctc tccgccaacg cgctttcggg agagcttccc tgctccctcc cgcgctcgct   1560
cctcgcgctc gacctctccc gcaacgcgct ctcgggggct gtccccacct gcctgccgtc   1620
ctcgctcccc gcgctccgca ccctcaacct ctccgccaac ttcctccgcc tcccgctctc   1680
cccgcgtctc tccttccccg cgcgcctcgc tgcccttgat ctctcccgca cgccatctc    1740
cggcgccgtc ccgccgcgga tcgtcgccga ccccgacaac tccgctctcc tcctcctcga   1800
cctctcccac aaccgcttct ccggcgagat ccccgccggt atcgcagccg tacggagcct   1860
gcagggctt tttctcgcgg acaaccagct ttccggggac attcctccgg ggataggaa     1920
cctgacctat ttgcaggtgc tggatttgtc gaataaccga ttgtccggtt cagtgcctgc   1980
cggacttgca ggctgcttcc agcttctgta cctgcagctt gggggtaacc agctctctgg   2040
ggcactccgt ccggagctcg acgcactagc tagtctcaag gttctagatt tgtcgaataa   2100
caagatatct ggggagattc ccctgccgct ggctgggtgc aggtctttgg aggtggtgga   2160
cttgtcagga aatgagatct ccggtgagct cagcagtgct gtagcgaaat ggctgagctt   2220
gaagttctta tcactggctg gtaaccagct ctccggccac ctacctgact ggatgttctc   2280
```

| | |
|---|---|
| gttcccctg ctccagtggc ttgatttgtc tagtaataag tttgtgggtt tcatcccaga | 2340 |
| tgggggttc aatgtcagtg aagtgcttaa cggtggaggt ggtcagggga ctccatcaga | 2400 |
| gagtgtgctt ccaccccaat tgtttgtgtc agcttctgtg gacacggtgt catggcagtt | 2460 |
| ggatttgggg tatgatgttc aggcaactac tggtatagac ctgtctggga atgagctctg | 2520 |
| tggggagata ccagaagggt tggttgacat gaaggggttg gagtatttga acctctcctg | 2580 |
| taattacttg gctgggcaga tccctgcggg gcttggggc atggggaggt tgcatacgct | 2640 |
| tgacttctca cataatgggc tgtcagggga ggtgcctcct ggaattgcag ccatgacagt | 2700 |
| gcttgaggtg cttaacctct cctacaatag cctgtctggg cctttgccaa caacgaagtt | 2760 |
| cccaggagca ttagctggaa acccaggaat ttgcagtggg aaagggtgct ctgagaatgc | 2820 |
| aaggactcca gaagggaaaa tggaaggtag caatcaccgc ggttggcttg gtggctggca | 2880 |
| tggagagaat ggatgggtat ctcttggtgc attttgtatc agcacaatga ctagcttcta | 2940 |
| tgtatcatta gcaaccttac tatgctcctc taatgcaaga aacttcgtgt tcggcctgt | 3000 |
| gagggttgaa tattaacaag aggggagatt gcaaaatcag gttgttttga agttcgagcg | 3060 |
| actctggtct gcagctgatt aacaagaaat atgagcatat gagatggata tcttcagcca | 3120 |
| agaggaagtg ctgtctcttt taatgatcaa tcaagctctc ttgattgttt cctaatattc | 3180 |
| ttgatcttgg gatgtgtaga tctagttcta atattcctac tgttatagaa tgcaatcacc | 3240 |
| tgctggtgct tggttgtagc cctggcgtgt ttggaggatt ggacaccaag gatgcacata | 3300 |
| atttgaagcg ctggtactgt gaaccacttc agatgtaaat attttctttg gttttagtt | 3360 |
| ctgatctagt ttaaaactgg acatgtattt agtgttgttg agctaccttt cgatgttata | 3420 |
| ttatgtcaat ttgctggaag atcatttgat aacaattgtc taatccagtg gattagtcgt | 3480 |
| gtagattgtg aagttcgtta tgtttcttct tagtgctatg tatatcatct ttctgtctga | 3540 |
| acttagtttg ggggtaaaag gctttgttat tatgtgactg aaactgcaaa tgtgcttgac | 3600 |
| tatttcttgg tgctgctcct gtaacaccta tagttttata ggtcaatggt aatagctgcc | 3660 |
| tgaagcagca tccagcaggc cggcaactgt ttttggtact gtaatacttt ggaacagagg | 3720 |
| cgcaaagttt gtgattgcag aatgatcaac aaatgtattt attgcaaagt gtgagacaag | 3780 |
| gcaacataca tatctctgtt ttgtgcatta ccaaactaac ccaggctgta attgcagatt | 3840 |
| gataattcct atagccgtag cttcttcagc tggataaggt ggagaataag catcagtggc | 3900 |
| ttttcaaagg gttcggcact tgtgcagaat cagactcatg caggaatccg ttctaacttt | 3960 |
| ttccactaaa acctttttcc tttctgaact tgctgcagta cctaccacta cttgtaatgt | 4020 |
| tggatcagtt tcacagttaa ccacagaatt tcattgcttt taatcaaacg tgaaatggtc | 4080 |
| acacagaaaa accaacatcc ttcagaaccg ctc | 4113 |

<210> SEQ ID NO 37
<211> LENGTH: 4341
<212> TYPE: DNA
<213> ORGANISM: Zea mays

<400> SEQUENCE: 37

| | |
|---|---|
| gtggagattt cctctgatca tcagatcatg atccttcgtt cctttgtga gggaaaaaag | 60 |
| aacggcggaa atgcgctgcc aattccggga aactacacat ccttcttctt tcttcttgca | 120 |
| cgaccacaca acacaaatgg tggccggtgc ccttaacctg ttacagcttt cggacgatct | 180 |
| tcgaatgcac ttcaactgtg ggaagaaatc agaccatcat tttcaccgat gagacatata | 240 |
| ctcacacact tctacttgaa tggttgttta tcttttgagc aaaaagtcac cgccagaaat | 300 |

```
ggcgccgatg ggtgtgcctg tgctgccgag ggttaacgat ggaagctact agcgtagccc    360
ctagtgctgg agcaaattga tggcgctcgt cccgtcccgt cccgtccctc cctctgctgc    420
gcgcgcctac gccccgcccc tctttctctc tctctgacac cgcacgccgt gcacccagcc    480
gtccactgat ccaccaccac caccccctccc gtctcccgcc atgccacctg cctttgacct    540
gcctatcatc tcgcccgcgc cgtccccgtc cccgtccccg ccgccgccga ttccattcca    600
tatgcccatt ccctcctcca ccaccaccac cgctaagccc ctcactccgc tcgcttccct    660
tttattccat ccgccacccc cacgccccc  tcgccaccac accacaacgc cacaatcaca    720
atgcctcctc ccaccttcct cctcggcctc ctcctcctcc tcctcctcgc cgccgccgcc    780
cccgcccccg cctccgccac gccggagcgg gacgcgtacg cgctgtcgag gctcaaggcg    840
tcgctcgtcc cgtccgccac aaactccacc tcggcaccgg tgtccgactg ggacccggcc    900
gcgaccccgc cggcgcactg cgcgttcacg ggcgtgacct gcgacgccgc cacgtcgcgc    960
gtcgtcgcga tcaacctcac ggccgtgccg ctccacgggg gcgcgctccc gcccgaggtc   1020
gcgctgctgg acgcgctcgc cagcctcacc gtcgccaact gctatctccg cggccgcctc   1080
ccgcccgcgc tcgcgtccat gcccgcgctc cgccacctca acctctccaa caacaacctc   1140 agcgggcccct tcccgccgcc gccccccgcc gcctacttcc cggcgctcga gatcgtcgac   1200
gtctacaaca caaacctgtc cggcccgctc ccgccgctgg gcgcgccgca cgcgcgctcc   1260
ctccgctacc tccacctcgg cgggaactac ttcaacggct ccatcccgga caccttcggc   1320
gacctcgccg cgctcgagta cctgggcctc aacggcaacg cgctgtcggg ccgggtcccg   1380
ccctcgctct ccgcctctc  ccgcctccgg gagatgtacg tcggatacta caaccagtac   1440
agcggcgggg tccgcgcgcga gttcggcgcg ctccagtcgc tcgtccgcct cgacatgagc   1500
agctgcacgc tcacggggcc catcccgccg gagctcgcgc ggctgtcccg cctcgacacg   1560
ctcttcctcg ccttgaacca gctcacgggg gagataccgc cggagctcgg cgctctcacc   1620
agccttcggt cgctcgacct ctccatcaat gacctcgccg gcgagatacc cgccagcttc   1680
gccgctctca ccaacctcaa gctgctcaac ctcttccgga accacctccg cggcgagata   1740
ccggccttcc tcggcgactt ccctttcctc gaggtgctgc aggtgtggga caacaacctc   1800
acaggccccc tccgcccgc  gctcggcagg aacggccgcc tcaagacgct ggacgtcacc   1860
agtaaccacc tcaccggcac cataccgccg gacctctgcg ccggacggaa cctgcagctg   1920
ctcgtgctca tggacaacgg cttcttcggc agcatccccg agtcgctcgg cgactgcaag   1980
acgctcacgc gcgtccgcct cggcaagaac ttcctgaccg gccccgtccc ggccgggctc   2040
ttcgaccttc cccaggcgaa catgctcgag ctcaccgaca acatgctcac cggcgagctc   2100
ccggacgtga tcgctggaga caagatcggc atgctcatgc tggggaacaa tcgcatcgga   2160
gggcgcatcc ccgccgctat cggcaacctc cccgcgctgc agacgctgtc cctggagtcg   2220
aacaacttct ctggcccgct gcctccggag atcggcaggc tcaggaacct caccaggctc   2280
aacgccagcg gcaacgcgct cacgggaggc atcccgaggg agctcatggg ctgcgcctcc   2340
ctgggcgccg tcgacctcag ccggaacggc ctcaccggcg agataccgga caccgtgacg   2400
tcgctcaaga tcctgtgcac gctcaacgtg tcgaggaaca ggctgtcggg cgagctgccg   2460
gcggcgatgg ccaacatgac gagcctgacg acgctggacg tgtcctacaa ccagctgtcg   2520
ggccccgtgc cgatgcaggg ccagttcctg tgtgttcaacg agagctcgtt cgtgggcaac   2580
ccggggctgt gcagcgcgtg cccccccatcg tccggcggcg cgcggtcgcc cttctcgctg   2640
```

| | |
|---|---|
| cgccggtggg actcgaagaa gctgctggtg tggctggtcg ttctcctcac cctgctggtc | 2700 |
| ctggcggtcc tgggcgcgcg gaaggcgcac gaggcgtggc gcgaggcggc gcggcggcgg | 2760 |
| tcgggggcct ggaagatgac ggcgttccag aagctggact tctcggcgga cgacgtggtg | 2820 |
| gagtgtctca aggaggacaa catcatcggc aagggcggcg ccgggatcgt gtaccacggc | 2880 |
| gtgacccgcg gcggcgcgga gctggcgatc aagcggctgg tggggagagg gtgcggcgac | 2940 |
| cacgaccgcg ggttcaccgc agaggtcacc acgctgggcc gcatccggca ccgcaacatc | 3000 |
| gtgcgcctgc tcggcttcgt ctccaaccgg gaggccaacc tgctgctgta cgagtacatg | 3060 |
| cccaacgggt cgctaggcga gatgctgcac ggcggcaagg ggggccacct cgggtgggag | 3120 |
| gcccgggcgc gcgttgcggc ggaggcggcg cgcgggctct gctacctgca ccacgactgc | 3180 |
| gcgcccggga tcatccaccg cgacgtcaag tccaacaaca tcctcctcga ctccgccttc | 3240 |
| gaggcgcacg tcgcggactt tggcctcgcc aagttcctcg gcggcggcgg cgccacgtcc | 3300 |
| gagtgcatgt ctgccatcgc cggctcctac ggctacatcg ccccaggtaa caaaactctc | 3360 |
| gccgcatagc agcataacca cgtgtttgta ctccttttaa taatattttt ttcactggct | 3420 |
| cgcatgcaga gtacgcgtac acccttcgcg tggacgagaa gagtgacgtg tacagcttcg | 3480 |
| gcgtggtgct gctggagctc atcacggggc ggcgccccgt gggcagcttc ggcgacggcg | 3540 |
| tggacatcgt gcactgggtg cgcaaggtga ccgcggacgc cgccgccgcg gaggagcccg | 3600 |
| tcctgctggt ggcggaccgt cggctggcgc cggagccggt gccgctgctg gcggacctct | 3660 |
| acagggtggc catggcgtgc gtggaggagg ccagcacggc ccggcccacc atgcgcgagg | 3720 |
| tcgtgcacat gctctccacc tccgccgcgg cccagcccga cgtcccccac gccttgtgca | 3780 |
| aggtcgtcga ttaatttgcc ttatatatga cgattatgta tatgatccgg gcagggttag | 3840 |
| cgcctgtgat ctatttagcg gctgcctttt tggcgtcact cgtctcgtgt gtgatgatgg | 3900 |
| ctggatggat gtgtaaaaca aataaccagc aggtggctac tcgtgaatga agttgccgg | 3960 |
| ttcttattct catgcatata tattagcaac acacaaagtg agatggcata tattcccttt | 4020 |
| ccctggcgtt tgttgctttg ggttattcgt cttggcttct cgcggaaggt cttctgctg | 4080 |
| ttcttgaacg acaggatagt atagaggctt ctatgagaaa gatgcttcat gctgcgaaag | 4140 |
| ttgaaaatgg cagatgcaca ttgcgtatcc ccacagggca ggacactttg cgcatggcct | 4200 |
| agtactaaca caatccatgg agcaaggaac attactgccc ttggcctcca agctgcttcc | 4260 |
| ttaatcatca aggatgaatt aggaaaaaaa aggataaacg gaccgccatg accagagcca | 4320 |
| gtgagggagc cacttcacct g | 4341 |

<210> SEQ ID NO 38
<211> LENGTH: 1753
<212> TYPE: DNA
<213> ORGANISM: Zea mays

<400> SEQUENCE: 38

| | |
|---|---|
| taagtcttgt atattgtatg tcgtgactct ccaccgccat acaatacgtg gctgaacagc | 60 |
| caagggagag aaagaggagg cacctatgac gttctcctcc tttatttttgc ggtcctttat | 120 |
| taatcccaac ttttctattt cttttcttgt tttccccttt cccacctaga ttcatccttg | 180 |
| cagtgtagat ctattttttct tccacacgtc tagcctaaca actagataag ataaaactta | 240 |
| tatcttatac tctctgttcc aaattaaaat ttgttttagt gaattattgg attcaaacaa | 300 |
| ttcttgatat tttgtatatg tgtctagatt tatcatcatt tatttgaata tatagataaa | 360 |
| aaacaatagt taaaacgaat attattttaa gacggagcga gtatatcatc atacgatacg | 420 |

```
tggctgatct cacaatctca acgtggtcaa agttgtgtgt gccgggccat ctgcgcgtcg      480
tgtgacaccg gtgcatgcgc agccttttgt tttgccgccc cgcccgctcc atgcatggca      540
tgggtgcagg ttctgtagct atgcccggaa gcacctagct agctcgcagc ctacatctgc      600
aaactcacaa agtttgggta tcggaggcat cagcaggtcg ggttcaatgg aacgacggat      660
cacgtctgtg tgtcgctttc gcagcagcgg ggagagcgcg gggcccggcc caggacgcat      720
ggaccgatgg acgcatgcag accattttg tttttgtttt tgttttgtt ttttcctgt        780 ctaaaatgta ggtgtgctct atcttgcctc ttcatgcgat aatgtgtgtg tatatatata      840
catgcccttc actcttctta tagctcgcta gcccagcttt agtttatagc actctctcac      900
tcagtagtca gctccctcca tttgtccatt ctccaaaggt agttagctag gttaggcaca      960
cgcgcgccac tcgactagct agcagctatg gaggagaag atgacggcgc ccaaatgaaa      1020
ctgcagcaac aacaacagtc gccttgcagt gacaacttga gcttgtccgc cgcctcctca     1080
tggctgccgc cacaggtaag gtcgtcgtcg tcgtcgtcgt cgtacacctg cgggtattgc     1140
aagaaggagt tcagatcagc acaagggctg ggaggccaca tgaacatcca caggctggac     1200
agggccagac tgatccacca acagtacact tcacaccgta ttgctgctcc ccatccaaac     1260
cctaatccta gttgcacatc agttcttgac cttgagctca gcttgtcgtc gctgctagcg     1320
catggtgctg ccagcagcga cggaggcttg tctgttccag tggcaaagct ggcgggcaac     1380
cgtttctcct ccgcatcgct ccccacgacc aaggacgtcg aggggaagaa cttagagttg     1440
aggataggag cgtgcagtca tggcgatggc gcggaagagc gtctggatct tcagcttaga     1500
ctgggctact actgagccag acagaggaac gaactgctac aatgggtacg tgcagtgcat     1560
gatgatggaa tgactggctt tgtataataa taatgatgat ccgattattg ttatttctgt     1620
atgctaaata tatgtctctt atgttagatt taatatatat gacatatttt atctaactaa     1680
attaaataaa ttatatatag gcgtcaacgt attaaatacg tctagggcat cgtagtcttt     1740
ccgaggtgtc tta                                                        1753

<210> SEQ ID NO 39
<211> LENGTH: 2625
<212> TYPE: DNA
<213> ORGANISM: Zea mays

<400> SEQUENCE: 39
cactatatga cactggaggt gtatgcatac gtatgagcat gaggaaaatt attaagaaaa       60
tatttgtagg gactttaaaa atgattacga gggtatttct gaggagaaaa atattttgag      120
aaatattaat ggaatcttta ggcagtattt ctggaaagaa tttgatggag tcactggaaa      180
aatatttgta ggatattttg aaaagaattt tggagagaat atatagcact atattttatt      240
tgttgtgatg aacttgcaaa caaacatttg taaacacaat tttaaaatcc attttaaatt      300
taggactagt tcaagtaatt ttatggtttt gaattttcg gaggctataa tcaccctaat       360
ccaatgagtc tctacttacg cgcttgcttt ccccttaact ctacaaattt ctcgagtacc      420
taagaaacac taatatcgtc atgcaacgac aatgttcatc taatttttat gaaaaattta      480
tgcctattgg acaaatatta aggttggatg aaatagtgag aagttaggac ataattatgg      540
tcacggttag ttttaatgta tgtcccctcc acgtctataa ctcttctttt actagtagct      600
acaatatcta aaacttactt gctataactg agggtataat attcctatgg aagtgttagt      660
agcttgtgaa ctttcttatg gttaaaactg tctatccata tttaacgtga ttggctgttt      720
```

```
atttatttag tattcattتt agagtcagca gtgatttagc ggagaaaggg agagtctggg      780
caattggcgg tctctggtgt catttgacca gtgccaggtc tcagtctgag tctatagtca      840
acagtgatct ctcggtcatt ggttggcagt ctcaggcaca cacaatgaca caacacaagc      900
agggcacagt cacagtgtga gctgagctga gctgggcttg tgcttgtgct tccgcctcct      960
cctccgcggc tactaaaggg tgccagccag ccagccctgt ggggcgccgg tgcgtgccca     1020
aaacaagcaa gcataagcat agaggtgggc atcatagaca tggaggatga cgaggacata     1080
tgggcaaaca ccgccagcag ccccagcgcg tccccaccgc agcccgtggc ggcgggctcg     1140
gtctccacct gcagcgcctt catctccacg cagctgagcc tcaactcccg cctccacctc     1200
ctctcctccg ccgcggccgg gggcgggtcc tccccggtcc gcggcggcgc ctacggcgcg     1260
gacggtgtcc gccaccacca catggctctc ggcggtggct tccgcaatgc cgcggcgtcc     1320
caggggtcct tctttccgta caacctcgcc ggcgccggcg ccgatgtcgc gcccttcgac     1380
ggcggccgcg gcgtgctcga ggacgacatg tctgtcggcg ccgccgcgtc cggcacctgg     1440
gctggcgggg gcaccgaccg gcggaagaag cgcatgatca agaaccgcga gtccgccgcg     1500
cggtcccgcg cgcgcaagca ggcgtacgtc cgcgagctgg agacgaaggt gcagctgctg     1560
cagcaggaga acgagagcct ccgcgtcaag tacgacgagg taagcgggac atcgagagcc     1620
cccggcccตt catatatatg gtcgctttgc tcaaagctcg cgcgtggatt gggcagctgc     1680
gggagtccgt ggaggtggcg gtgccgatgg tgaggaagac cctgcagagg atgccgtccg     1740
cgccgttctg aggacattga ccggagatga gtcgaagcag gtggttgctc gttttgtttg     1800
tttttgagg aggtgattaa gtaagtgact gattagtgag tggctgctgc ctagtgcttg     1860
gttactagta gtggtagaac tcagaactac atagatccag gaagcaagca agcaaatcct     1920
tcctgccatg gcggcctcaa tgtacataga tcccatgttt ttattaattt cgtctagctg     1980
gggggcgtg cacctgccat ggcggcctcc tttatttagc tttatataag taggatgtag     2040
gatgtctacc atatgtgtgt agcttgggat taggctgcaa gaagataagc ctgcttgtac     2100
aaatatggct tcctggaaca atgacattต gggggcgcaa cgcaagaaag atgaaagaac     2160
aatccaggaa gcagcaggtg ttttcttctt cttcttcttt tgcccccttcc atgatattcg     2220
cgtgtcaaag gctctcctaa agcgagtagt agtcttttgg tttggtgaat atttgctgtt     2280
ttcatgctgg tccctgctga tgtttgcgat gattttacaa tcagaaagag acgttttttg     2340
gttttgcctc cattctcttt ttgttgctca gctttggcga gggggaaagc cagtaatttc     2400
gacgataggg aacaaaaaat ggatcgaatt ttgggacccc tttgcttttc tgaaagatgg     2460
aacagaaggc aaacaaatcc tgactattgg gaggatctaa ttttتccttt tttagacaat     2520
gtagagcagc tgcttcccta caccaggcag gaggcactgg accacagaca cgcaaacaga     2580
gctgcaagtc tgcctccccc caagcaccct gctccctccg atcta                    2625
```

METHODS AND MATERIALS FOR HIGH THROUGHPUT TESTING OF MUTAGENIZED ALLELE COMBINATIONS

CROSS-REFERENCE TO RELATED INVENTIONS

This application is a 371 National Stage application of International Application No. PCT/US2017/016908, filed Feb. 8, 2017, which claims the benefit of U.S. Provisional Application No. 62/294,539, filed Feb. 12, 2016, each of which is herein incorporated by reference in its entirety.

TECHNICAL FIELD

This document relates to methods and materials involved in improving traits in organisms. For example, this document provides plants and materials and methods for making plants and plant products, where crops of the cultivated plants achieve improved agronomic characteristics or plant material quality.

Incorporation of Sequence Listing

The sequence listing that is contained in the file named "CRES032WO_ST25.txt" which is 127 kilobytes as measured in Microsoft Windows operating system and was created on Feb. 7, 2017, is filed electronically herewith and incorporated herein by reference.

BACKGROUND

Modern elite varieties of cultivated plant species are generally highly bred, meaning that they have undergone a large number of cycles of artificial selection for improved agronomic traits. This process has resulted in the accumulation of a large number of favorable alleles in elite genetic backgrounds. Hence, for further improvements to elite performers, much of an existing genetic material needs to be maintained. But, generation of new genetic diversity by means of mutagenesis or wide crosses often begins with massive changes of the genetic material. A laborious isolation and evaluation process generally results in relatively few new loci that are sufficiently favorable to justify incorporation into improved elite varieties. Moreover, specific pairs of allelic variants may exhibit positive epistasis, but they may elude identification if their occurrence emerges only from random mutagenesis or recombination. A need exists for an improved system for generation of saturation or near-saturation mutagenesis of agronomic trait candidate loci and for testing the effect of combined mutations, preferably within an otherwise uniform elite genetic background.

SUMMARY

This document provides methods and materials for improving one or more phenotypic features in an organism. For example, this document provides high throughput methods for identifying combinations of mutations that can be used to improve a phenotypic feature in an organism. As described herein, large populations of organisms (e.g., plants) containing different combinations of mutations can be grown side-by-side. These large populations of organisms are genetically nearly identical, except for the specific combinations of mutations in each plant. The particular combinations that result in desirable phenotypes can be identified based on improved quality or performance in the field or greenhouse or lab testing. Combinations of mutations can generate significant phenotypes as their effects may be additive or synergistic.

In one aspect, this document features a method for identifying combination of genetic mutations that improves a phenotype of a plant. The method includes selecting a plurality of genomic targets (e.g., 4, 5, 6 or more genomic targets); making a plant cell that has both gRNAs designed to mutate the selected genomic targets and a Cas polypeptide, so that a plant descended from the plant cell will have germline mutations; sexually crossing a first parental plant comprising at least a subset of the germline mutations to a second parental plant to produce a progeny population; selecting at least one progeny plant the population as having an improved phenotype to obtain a selected progeny plant; and determining which mutations are present within the selected progeny plant, thereby identifying a combination of mutations that improves a phenotype of a plant. The method can include repeating all the steps by either selecting genomic targets determined to be mutated in the selected progeny, using in the sexual cross a parent related by lineage to the selected progeny, or both. The plants could be corn (*Zea mays*) and the genomic targets can comprise at least one of SEQ ID NOs: 26-39. The plants could also be sorghum (*Sorghum bicolor*), wheat (*Triticum aestivum*), or rice (*Oryza sativa*).

In some embodiments at least some of the different gRNAs are designed to mutate distinct residues of the same genomic target. n some embodiments at least some of the different gRNAs are designed to mutate residues within conserved sequences of paralogous genes. In some embodiments a plant cell is made by inserting gRNA-expressing transgenes. In some embodiments a plant cell is made by adding a Cas9 polypeptide-expressing transgene, which may be accomplished by crossing. In some embodiments a plant cell is made by contacting the cell with pre-assembled gRNA-Cas9 ribonucloeoproteins. In some embodiments the first parental plant is a progeny of selfing a plant with germline mutations. In some embodiments the first parental plant is a progeny of a cross of the plant having germline mutations to a wild type plant or to another plant, so that the germline mutations of the first parental plant are heterozygous. In some embodiments the first parental plant does not have a Cas9 polypeptide-expressing transgene. In some embodiments in the second plant also has germline mutations. In some embodiments the first and second parental plants are isogenic and belong to complementary heterotic groups. In some embodiments the first parental plant or the second parental plant is cytoplasmically male sterile.

Selecting at least one individual with an improved phenotype from the progeny population may be based at least in part on performance of the plant under field testing conditions. The selection may also be based at least in part on other criteria such as the selected plant's water use efficiency, nitrogen use efficiency, seed oil content, or plant density stress performance. In some embodiments, the progeny population from which an individual is selected may be itself be selected by genotyping, for example by seed chipping. A collection of seeds can be made with embryonic cells having a combination of genetic mutations identified according to the methods described.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWING

FIG. 1: Progenitor plants have multiple gRNA-expressing transgenes or a Cas9-expressing transgene. When crossed, the progeny combining the expression of Cas9 and gRNAs produces germline mutations of the gRNA targets. A cross with a wild type plant of a similar genetic background allows for segregation of Cas9 and gRNA transgenes, as well as making the mutations heterozygous. Crossing plants heterozygous for the mutations, here shown on the female side, with plant of a complementary heterotic group, results in formation of hybrids that recombine the mutated alleles. These hybrids can be phenotyped for the traits of interest to select favorable combinations of mutations.

DETAILED DESCRIPTION

This document relates to methods and materials for identifying or optimizing combinations of mutations that improve one or more phenotypic features of an organism. For example, the methods described herein can be used in plants to improve grain yield; tolerance to an abiotic stress such as drought stress, osmotic stress, or nitrogen deficiency; soil aluminum; cold stress; frost stress; density stress; heat stress; oxidative stress; low light tolerance; herbicide stress; as well as improved water use efficiency; nitrogen use efficiency; phosphate use efficiency; seed oil or protein content; lignin content; biotic or pest resistance; biomass; heterosis; chemical composition such as higher percentage of sucrose; plant architecture such as increased tillering or branching, decreased or increased apical dominance, or increased root mass; flowering time; and/or biofuel conversion properties in a plant. "Water use efficiency," "nitrogen use efficiency," or "phosphate use efficiency" refers to increased yield under the same levels of input, i.e., same level of water, nitrogen, or phosphate.

In general, the methods described herein can include obtaining first and second parental organisms, wherein at least one of the parents includes a plurality of mutations introduced by genome editing, sexually crossing the parent organisms to produce a progeny population, and identifying the combinations of mutations that improve a phenotypic feature. In some cases, one of the parental organisms can be a wild type plant. In some cases, each parent can be mutated and can include one or more mutations. As described in more detail below, the first and/or second parental organisms can be heterozygous for the mutations, and the gametes of one or both parental organism can include independently segregating subgroups of the plurality of mutations.

Mutations are generated in selected genomic targets of an organism (e.g. a crop plant) by genome editing using a CRISPR/Cas system. Accordingly, a guide RNA (gRNA) that is directed to a residue of the genomic target and a Cas endonuclease must be simultaneously present in the same cell as the a genomic target to be mutated. The gRNA binds the endonuclease and guides it to the genomic target at the location where it is complementary to the engineered gRNA sequence. After the endonuclease cleaves the genomic target, many types of mutations (e.g. insertions, deletions, substitutions) around the nucleic acid residues of the target of the respective gRNA will be formed, often by the error-prone Non-Homologous End Joining (NHEJ) pathway. Consequently, the same gRNA/Cas can act to make multiple mutations, and different mutations can produce different phenotypes.

In some embodiments, as depicted in FIG. 1, gRNAs and Cas endonucleases are produced by the expression of transgenes. Consequently, Cas expression can be maintained in a separate plant from the one or many gRNA-expressing transgenes, as needed for carrying out the present methods. Then, Cas can be brought together with selected gRNAs by crossing two parents having these transgenes, as long as their co-expression will occur at least in germline cells. In this illustrated progeny, Cas and gRNA-expressing transgenes are hemizygous, and their simultaneous expression of both gRNAs and Cas molecules generates mutations. But individual progeny of this cross will not be uniformly mutated, since the same gRNA can generate different mutations. The progeny population may be useful at this point to identify combinations of mutants with improved phenotypes, especially if co-expression occurs early in development such as in the fertilized egg or the embryo. In some cases, however, it is desirable to segregate at least the Cas transgene so as to both avoid additional mutations and form different combinations of the mutations. This can be accomplished with a different cross, illustrated with a wild type (wt) parent in FIG. 1. The progeny of this second cross will have the mutations in a heterozygous state. Consequently, a cross of this progeny with another plant will result in recombination of all the mutations, and the progeny will be a population having different segregating mutations. This population, noted as F1 in FIG. 1, can be phenotyped for identifying outstanding pairs or combinations of mutations.

The methods described herein provide a number of advantages when compared to alternative solutions, although not all advantages may be present in a specific embodiment.

For most breeding objectives, commercial breeders work within germplasm that is often referred to as the cultivated type. This germplasm is easier to breed with because it generally performs well when evaluated for agronomic performance. The performance advantage the cultivated type provides is sometimes offset by a lack of allelic diversity. This is the tradeoff a breeder accepts when working with cultivated germplasm: better overall performance, but a lack of allelic diversity. Breeders generally accept this tradeoff because progress is faster when working with cultivated material than when breeding with genetically diverse sources.

In contrast, when a breeder makes either intra-specific crosses, or inter-specific crosses, a converse trade off occurs. In these examples, a breeder typically crosses cultivated germplasm with a non-cultivated type. In such crosses, the breeder can gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, *Proc. Am. Soc. Hort. Sci.* 44:413-16). In this cross, a nematode disease resistance was transferred from *L. peruvianum* into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked.

Some phenotypes are determined by the genotype at one locus. These simple traits, like those studied by Gregor Mendel, fall in discontinuous categories such as green or yellow seeds. Most variation observed in nature, however, is continuous, like yield in field corn, or human blood pressure. Unlike simply inherited traits, continuous variation can be the result of polygenic inheritance. Loci that affect continuous variation are referred to as quantitative trait loci (QTLs). Variation in the phenotype of a quantitative trait is the result of the allelic composition at the QTLs and the environmental effect. The heritability of a trait is the proportion of the phenotypic variation attributed to the genetic variance. This ratio varies between 0 and 1.0. Thus, a trait with heritability near 1.0 is not greatly affected by the environment. Those skilled in the art recognize the importance of creating commercial lines with high heritability agronomic traits because these cultivars will allow growers to produce a crop with uniform market specifications.

Consequently, mutations conferring improved agronomic traits are a powerful tool in the development of new and improved cultivars. Mutations are defined genetic alterations that do not require segregation from linked regions in order to avoid genetic drag. And again due to their genetic nature, contributions of mutations to a defined trait have high heritability. As explained in more detail below, however, the precise impact of a mutation or combination of mutations needs to be experimentally measured to understand the extent to which it depends on the relevant QTLs present in the germplasm in which they are tested. Understanding any QTL-dependent mutation impact is helpful, for instance, in cases where a mutation has a phenotypic effect in a heterotic genetic background that is significantly different in magnitude from the corresponding effect in plants with inbred depression.

Exploring the phenotypic effect of many stacked mutations, rather than single mutations, is more likely to result in finding mutations resulting in significant yield or quality improvements. The genome of cultivated plants, for example, comprises a background system of complex molecular interactions. For a mutation to boost a trait its products need to fit into the complex, regulated downstream networks appropriately. If the genetic background changes then the effect of the mutation may change too. For this reason specific mutations sometimes fail to achieve the desired effect in all genetic backgrounds and environments. A change to a single component of a very complex system is unlikely to have a dramatic positive effect; several distinct alterations, on the other hand, as with a stack of mutations, are more likely to result in an enhanced or synergistic positive effect, and/or diminished negative features of a mutation-caused pleiotropic phenotype.

The methods described herein make it possible to produce and test in parallel a high number of mutations in different combinations. Any phenotypic feature could be affected by a large number of candidate mutations, and a much larger number of combinations or stacks mutations. But the phenotype of individual combinations, which may or may not turn out to be additive or even synergistic when compared to the phenotype of single mutations, is generally unpredictable, so testing a large number of combinations is necessary. Hence, the high-throughput methods described herein are useful for quickly sorting through large numbers and identifying the combinations of mutations that improve one or more phenotypic features. In other words, existing methods, such as random mutagenesis, would produce too rarely similar combinations as made possible by the methods presented here, and these combinations would be difficult to sort out as their effect would be entangled with the deleterious effects of other combinations. It is worth noting that while unpredictability of produced mutations with some CRISPR/Cas mutagenesis systems can actually be problematic for their application in other technological areas, it is actually advantageous for the methods presently described.

Generating new mutations, such as by random mutagenesis with mutagens or by wide crosses, while routinely accomplishable, is also a process that by its nature adds challenges to studying comparative performance of plants. This is because multiple unrelated mutations accumulate and generally create a range of mutant phenotypes in independently selected plants. Mutations causing genetic drag need to be segregated first to understand the potential impact of individual mutations or their combinations. Hence, compared to use of random mutagenesis, the procedures described here often require a limited number of backcrosses, if any, which cuts down on the amount of labor necessary to make and characterize the materials, but more importantly provide results such that the relative performance of combined mutations can be reliably scored. Moreover, mutations or combinations are "recyclable", i.e. once made and characterized they are likely to find use in multiple seasons and experimental setups. For example, interesting mutations only need to be made once, and then they can be used repeatedly in combination with many other different mutations, and may need to be introgressed only once into any parental germplasm of interest. This feature is especially convenient for testing in elite germplasm because of the added effort sometimes required to introgress any mutation into a uniform and commercially relevant genetic background. In some aspects, the methods presented here maintain the benefits of random mutagenesis without the drawbacks. They enable testing in elite backgrounds of large number of combinations of only the most likely yield and quality impact candidate mutations. Since the impact of mutations can be dependent on the genetic background, testing in directly elite backgrounds is advantageous, by eliminating from consideration mutations of diminished impact in elite materials. Phenotyping of candidates is also convenient because of the uniform genetic background of the siblings that make up testing populations, which can be planted in proximity so that improved phenotypes can be easily scored.

In many cases, testing populations are made based on isogenic backgrounds so as to eliminate background genetic noise that would otherwise confound data interpretation. But in other cases, especially when the effect of a limited number of combined mutations is to be understood, the genetic background may be intentionally diverse. For example, a promising stack of mutations could be observed for performance in a segregating F2 population and subsequent generations, thus allowing selection and production of parents capable to perform especially well in the presence of a specific combination of mutations.

Using the presented methods, a phenotypic measurement can be the yield of harvestable material under typical field cultivation conditions, i.e. without an intentionally applied selection pressure. This data is certainly relevant from a product performance perspective, for identifying undesirable interactions of stacked mutations, and when stacking mutations affecting different traits that cannot be revealed by a single assay. But in addition, while some mutations or stacks provide a survival or yield advantage under high selection pressure, they are known to otherwise have a negative impact when grown under typical cultivation conditions. Moreover, the populations of plants produced by the present methods are well-suited for comparative studies of related combinations. When testing side-by-side sibling plants that are otherwise genetically uniform but differ only with regard to having distinct combinations of a limited original pool of mutations, stacks of outstanding phenotypic impact can be readily identified. In some embodiments, populations produced according to the methods provided herein can be tested for field performance similarly to screening of segregating populations by plant breeders. This way, the effect of high numbers of combined mutations can be simultaneously observed, often in a commercially relevant, elite genetic background, which may be made up of defined heterotic groups and/or QTLs for specific traits, and so well-performing mutants that surpass commercially relevant thresholds can be more easily identified. By using the methods described herein, useful combinations of mutations become self-revealing, circumventing the general unpredictability of the phenotype of stacked mutations.

Genomic Targets

Genomic targets for mutation are contiguous chromosomal DNA regions generally encoding expressed sequences. Most often they are genes comprising a transcribed sequence which typically comprises a polypeptide-encoding sequence, and regulatory regions. Regulatory region refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

Selection of genomic targets for mutation can be done rationally rather than randomly. For example, based on existing data, the targets can be known or inferred as likely to affect a trait, such as morphological development of a plant part that may increase yield or environmental stress resistance. The types of data useful in identifying genomic targets is dependent on the phenotype to be improved, but it may be from the location of quantitative trait loci (QTL), transgenic phenotypes caused by overexpression of sequences, participation in relevant signaling or metabolic pathways, involvement in relevant physiological process, or phenotypes of characterized mutations.

Genomic targets can be selected based on data from different species if needed, as functional homologs of a locus. Accordingly, one or more genomic targets in a species of interest can often be identified by sequence similarity to sequences in other species for which pertinent data exists. In addition to sequence similarity, conserved domains as defined by Pfam descriptions, synteny, and/or reciprocal BLAST results may be used in identifying suitable genomic targets. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. The term "functional homolog" is sometimes applied to the nucleic acid or gene that contains a functionally homologous polypeptide.

Functional homologs can be identified by analysis of nucleotide and polypeptide sequence alignments. For example, performing a query on a database of nucleotide or polypeptide sequences can identify homologs of interest as a genomic target. Sequence analysis can involve BLAST, Reciprocal BLAST, or PSI-BLAST analysis of nonredundant databases using a reference sequence of defined interest. Amino acid sequence is, in some instances, deduced from the nucleotide sequence. Those polypeptides in the database that have greater than 40% sequence identity are candidates for further evaluation for suitability as genomic targets. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in genomic targets, e.g., conserved functional domains.

Conserved regions can be identified by locating a region within the primary amino acid sequence of a genomic target candidate polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Once a genomic target is selected, it typically contains many distinct residues that may be mutated by genome editing techniques. Creating mutations of a genomic target at many residues is desirable so as to generate essentially all the potential phenotypes from that target. The mutations are introduced generally 3-4 residues upstream of the Protospacer Adjacent Motif (PAM), which is for example 5'NGG3' for the *Streptococcus pyogenes* Cas9. Consequently, any PAM sequence on either strand of the genomic target can be used in guiding an adjacent mutation. The residue to be mutated is often part of a polypeptide-coding region, although it could also be part of an intron or regulatory region. Mutating distinct residues of the same genomic target may be accomplished by introducing double or multiple mutations into the target with different gRNAs directed to mutate different residues, or by introducing single distinct individual mutations in different progenitor cells.

The phenotypes caused by individual mutations can range from indistinguishable from wild type to a most severe knockout effects. More rarely, gain of function mutations are observed. Phenotypes result from changes in function caused by the mutations. Depending on the nature of the target, many changes do not entirely obliterate (i.e. knockout) the function of the underlying wild type target, but may alter its expression level, its encoded polypeptide's affinity for substrate or for a protein complex to which it belongs, the cellular localization of an expression product, and/or its regulation in response to stimuli affecting its regulatory network. Mutations introduced close to the 5' terminus of a coding sequence are more likely to result in knockout phenotypes than mutations close to the 3' terminus. Consequently, when multiple distinct residues of a genomic target are selected, it is often desirable to select residues proximal to the 5' terminus and to the 3' terminus of the coding sequence.

In some cases, mutations can be directed to residues in conserved regions, so as to simultaneously mutate not only the main selected genomic target, but also paralogous genes sharing the conserved region. This approach can be fruitful, for example, if paralogous genes can substitute for each other to some extent. Alternatively, mutations can be directed to residues in unique regions to avoid mutating any paralogous genes.

Many genomic targets can be selected for mutation and testing. In general, it is useful to test all the different combinations of at least four targets simultaneously. But the number of targets in a development program can be much larger, i.e. 10, 15, 20, or 25 or more targets can be mutated at various residues and their combined phenotypic effect investigated. The choice of the multiple targets to be combined can be at least in part random, so as to enable observations of synergies between different phenotypes that might not be predictable. But, the combination of targets can also be at least in part non-random, so as to enhance the likelihood that the combined mutations would interact with each other and thus produce a new phenotype when combined. For example, many different targets can be selected based on their likelihood to produce a salt tolerant phenotype. Many mutations can be produced in each target, and different mutations of the targets can be recombined to identify those pairs or combinations that complement each other so as to perform exceptionally well on salt tolerance assays.

A gRNA can target one or more genes encoding a polypeptide necessary for elaboration of cell wall polysaccharides. Non-limiting examples of polypeptides necessary for elaboration of cell wall polysaccharides include polypeptides that function in the lignin pathway (e.g., phenylalanine ammonia-lyase (PAL), cinnamate 4-hydroxylase (C4H), 4-coumarate:coa ligase (4CL), p-coumarate 3-hydroxylase (C3H), p-hydroxycinnamoylcoa: quinate/shikimate p-hydroxycinnamoyltransferase (HCT), caffeoyl-coa omethyltransferase (CCOAOMT), cinnamoyl-coa reductase (CCR), ferulate 5-hydroxylase (F5H), caffeic acid o-methyltransferase (COMT), and cinnamyl alcohol dehydrogenase (CAD), and polypeptides that function in cellulose synthase. A gRNA can target one or more genes encoding polypeptides involved in hormone biosynthesis (e.g., repressors and/or critical enzymes). For example, reducing or eliminating the function of a repressor of a hormone biosynthesis pathway can be effective to increase hormone levels. In some cases, a repressor of a hormone biosynthesis pathway can be a corepressor. For example, reducing or eliminating the function of a polypeptide that brings about critical steps in hormone biosynthesis can be effective to decrease hormone levels. Non-limiting examples of polypeptides involved in hormone biosynthesis include polypeptides involved the gibberellin (GA) pathway, the brassinosteroids (BR) pathway, the indole-3-acetic acid (IAA) pathway, the jasmonic acid (JA) pathway, the abscisic acid (ABA) pathway, the salicylic acid (SA) pathway, the cytokinin pathway, and the ethylene pathway. Exemplary targets of the GA pathway include, for example, GA20-oxidase, GA3-oxidase, GA2-oxidase, gibberellin insensitive dwarf (GID), and other polypeptides described in, for example, Park et al. (WO2013/086499, published Jun. 13, 2013). For example, reduction or elimination of a repressor of the GA pathway (e.g., GA2-oxidase) can be effective to activate the GA response. For example, reduction or elimination of an activator of the GA pathway (e.g., GA20-oxidase) can be effective to repress the GA response. In some embodiments, a gRNA can be designed to target a combination of one or more repressors and/or co-repressors of a hormone biosynthesis pathway and one or more polypeptides that bring about critical steps in hormone biosynthesis. A gRNA can target one or more genes encoding a polypeptide that represses cell division (e.g., cell cycle regulators). Non-limiting examples of polypeptides that repress cell division include cyclins (e.g., *Arabidopsis* CDC2aAt, CDC2bAt, CYCB1;1, and alfalfa CDC2fM and CYCB2;2, and their homologs in other species) and cyclin-dependent kinase (CDKs).

One or more gRNA-expressing transgenes can be used to reduce or eliminate function of a gene (e.g. an endogenous gene) in a manner that enhances biocontainment (e.g., prevent outflow of the transgene into nature). Non-limiting examples of genes that can be targeted with a gRNA include, genes encoding polypeptides causing sterility (e.g., polypeptide involved in seed development), genes encoding herbicide tolerance polypeptides, genes encoding pesticide tolerance (e.g., insect resistance) polypeptides, transgenes encoding polypeptides providing agronomic traits, and transgenes encoding polypeptides involved in cell wall conversion and digestion. A gRNA can target one or more genes encoding a polypeptide causing sterility. For example, a polypeptide causing sterility can be a polypeptide involved in seed development. Non-limiting examples of polypeptides involved in seed development include FIE, AP2, INO, ANT, the polypeptide encoded by the LEC2 gene, and HAP3-type CCAAT-box binding factor (CBF) subunit.

A gRNA can target one or more genes encoding an herbicide tolerance polypeptide. Herbicide tolerance is also sometimes referred to as herbicide resistance. Non-limiting examples of herbicide tolerance polypeptides include a polypeptide encoded by a polypeptide encoded by a phosphinothricin acetyl transferase (PAT) gene, a bialaphos resistance (BAR) gene, 5-enolpyruvyl-3-phosphoshikimate synthase (EPSPS), acetolactate synthase (ALS), acetyl coenzyme A carboxylase (ACCase), dicamba mono-oxygenase (DMO), aryloxyalkanoate dioxygenase-12 (aad-12), and 4-hydroxyphenylpyruvate dioxygenase (HPPD).

A gRNA can target one or more genes encoding a pesticide tolerance polypeptide. For example, a pesticide tolerance polypeptide can be an insect resistance polypeptide. Nonlimiting examples of pesticide tolerance polypeptides include Cry1Ab, Cry1Ac, Cry1A.105, Cry1F, Cry2Ab, Cry3Bb1, Cry34Ab1, Cry35Ab1, mCry3A, and VIP3.

A gRNA can target one or more genes encoding a polypeptide conferring a desirable trait. For example, a desirable trait can be an agronomic trait. Non-limiting examples of agronomic traits include increased yield, drought tolerance, cold tolerance, tolerance to environmental stresses, enhanced nitrogen use, and male sterility. Other desirable traits can include, for example, pathogen (e.g., virus, fungus, bacterium, and/or nematode) resistance, and product quality traits (e.g., delayed fruit ripening, altered amino acid profile, altered oil profile, modified seed storage proteins, enhanced floral characteristics for ornamentals, 5 increased solids in fruit).

Seq id nos 6-10 and 25-39 provide some examples of genomic targets that may be selected and either mutated in their respective species or first used to identify similar genomic targets in other species of interest.

Grnas

Aspects of some embodiments relate to a transgenic plant (e.g., a parent plant or a progeny plant) that includes to at least one nucleic acid having a promoter operably linked to a gRNA sequence. "Operably linked" refers to the positioning of a regulatory region and a sequence to be transcribed in a nucleic acid so that the regulatory region is effective for regulating transcription of the sequence. Expressed gRNAs can target particular nucleic acid sequences (e.g., an endogenous gene) at which a Cas enzyme can induce a double stranded break. A gRNA can include a gRNA scaffold sequence and a gRNA targeting sequence, and can be designed to target a nucleic acid sequence within the genetic material of a plant (including the nuclear chromosomes, transgenic, choloroplastic, or mitochondrial sequences). A gRNA scaffold sequence can bind a Cas enzyme (e.g., Cas9) thus guiding the Cas enzyme to a target site at which a double stranded break is desired. See, e.g., Ran et al. (2013 Nat Protoc. 8(11):2281-2308). A gRNA targeting sequence can be a nucleic acid sequence that can hybridize to a target sequence within the genetic material of a plant (e.g., a gene within a plant). In some cases, a gRNA targeting sequence can hybridize to a coding or a noncoding strand of a target gene; thus, a gRNA targeting sequence can include a portion of a genomic target sequence or complementary to a portion of a genomic target. Hybridization refers to a reaction in which two single stranded nucleic acid molecules or regions of molecules form a complex that is stabilized via hydrogen bonding between complementary bases of the nucleotide residues. A gRNA targeting sequence that hybridizes to a genomic target can be of any appropriate length that is sufficient to promote hybridization, a double stranded break, and double stranded break repair (e.g., nonhomologous end joining) at the desired site. In some cases, the gRNA targeting sequence can include a portion of a genomic target or the full length of a genomic target. A gRNA targeting sequence can be from about 5 to about 45 nucleotides in length (e.g., from about 5 to about 45, from about 8 to about 40, from about 10 to about 35, from about 13 to about 30, from about 15 to about 27, from about 17 to about 25, from about 18 to about 24, or from about 19 to about 23 nucleotides in length). For example, the gRNA targeting sequence can be at least 5, at least 8, at least 10, at least 13, at least 15, at least 17, at least 18, at least 19, or at least 20 nucleotides in length. For example, the gRNA targeting sequence can be no greater than 45, no greater than 40, no greater than 35, no greater than 30, no greater than 27, or no greater than 25 nucleotides in length. In some cases, the gRNA targeting sequence includes 20 nucleotides. The amount of sequence identity shared by a gRNA targeting sequence and a desired site in a genomic target can vary. For example, the amount of sequence identity can be at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 30 96%, 97%, 98%, 99% or 100% sequence identity. Methods for determining hybridization conditions (including complementarity and percent sequence identity) that can used as described herein include, without limitation, those are described elsewhere (e.g., Sambrook et al. *Molecular Cloning: A Laboratory Manual,* 2nd ed., Cold Spring Harbor Laboratory Press, 1989; and Ausubel et al., *Current Protocols In Molecular Biology,* John Wiley & Sons, New York, 1987).

In some cases, the methods and materials provided herein (e.g., vectors) can include using multiple gRNAs directed to at least one target residue site within a gene (e.g., an endogenous gene) to reduce or eliminate function of the target gene upon mutagenesis. In some cases, a nucleic acid molecule can have at least one promoter operably linked to one gRNA-expressing sequence (e.g., one, two, three, four, five, six, seven, eight, nine, ten, eleven, twelve, or more gRNA-expressing sequences). In some cases, a nucleic acid molecule can have five gRNA-expressing transgenes. Multiple (e.g., two or more) gRNA-expressing transgenes provided herein can be directed to a single genomic target or can be designed to target multiple (e.g., two or more) genomic targets. In embodiments where multiple gRNA-expressing transgenes are directed to a single target gene, the gRNA-expressing transgenes can be directed to the same site within the genomic target, or the gRNA-expressing transgenes can be directed to different sites within the genomic target. In embodiments where multiple gRNA-expressing transgenes are directed to multiple genomic targets, the gRNA-expressing transgenes can each be directed to an independent genomic target.

Multiple (e.g., two or more) gRNAs directed to at least one target site within a gene (e.g. an endogenous gene) can be provided via a single nucleic acid molecule (e.g., in tandem expression cassettes) or can be provided via multiple nucleic acid molecules (e.g. on more than one expression cassette). In some cases, a nucleic acid molecule can have five gRNA-expressing transgenes provided via tandem expression cassettes. One or more gRNA-expressing transgenes provided herein can be used to reduce or eliminate function of a gene (e.g. an endogenous gene) in a manner that improves plant health (e.g., to provide desirable agronomic traits). Non-limiting examples of genomic targets that can be altered with a gRNA include genes necessary for elaboration of cell wall polysaccharides, genes that are repressors or co-repressors of hormone biosynthesis pathways, genes that bring about critical steps in hormone biosynthesis, and genes that repress cell division.

Nucleic Acid Molecules

In some embodiments, a transgenic plant can be a parent plant including a nucleic acid molecule having a first promoter operably linked to at least one transgene. For example, a parent plant can include a nucleic acid molecule having a promoter (e.g., a ubiquitously expressing promoter, which may direct transcription by Pol III, such as the corn U6 (SEQ ID NO: 3) or Sorghum U3 (SEQ ID NO: 4) promoters) operably linked to at least one gRNA-sequence to be expressed, and a parent plant can include a second nucleic acid molecule having a second promoter (e.g. expressing at least in germline cells) operably linked to a Cas-encoding sequence. It is typically desired, but not always necessary, that the at least one transgene does not itself cause any phenotype in the parent plant, for example via insertional effects. Expression of both a gRNA and a Cas allows for the formation of a gRNA/Cas complex capable of introducing a double strand break in a target site within a genome (e.g., within a gene). The double stranded break can lead to introduction of at least one mutation in a genomic target such that the mutation confers a modified function of that genomic target. As mutations occur in germlines, progeny plants inherit the modified function of the target gene.

A promoter refers to a nucleic acid capable of driving expression of another nucleic acid (e.g., a coding nucleic acid). A promoter is operably linked to another nucleic acid when it is capable of driving expression of that nucleic acid fragment. The choice of promoter to be included in a nucleic acid molecule described herein depends upon several factors, including, but not limited to, efficiency, selectability, inducibility, desired expression level, and cell- or tissue-preferential expression. In different embodiments, the Cas-encoding sequence can be placed under the control of any of a number of promoters that are capable of directing expression in at least some progenitor cells of germline tissues, so that egg and pollen cells comprise the mutations.

Preparation of the nucleic acids disclosed herein can be accomplished using techniques in molecular biology, biochemistry, chromatin structure and analysis, computational chemistry, cell culture, recombinant DNA, and related fields. These techniques are described, for example, in Sambrook et al. Molecular Cloning: A Laboratory Manual, 2nd ed., Cold Spring Harbor Laboratory Press, 1989; and in Ausubel et al., Current Protocols In Molecular Biology, John Wiley & Sons, New York, 1987.

CRISPR-Associated (Cas) Genes

CRISPR/Cas systems are known in the art and can be engineered for directed genome editing. Cas genes encode RNA-guided DNA endonuclease enzymes capable of introducing a double strand break in a double helical nucleic acid sequence. Nucleases engineered to introduce single strand breaks can also be suitably adapted for use with the present invention. The Cas enzyme can be directed to make the double stranded break at a target site within a gene using a guide RNA. A Cas enzyme can be guided by a guide polynucleotide (e.g., a guide RNA) to recognize and introduce a sequence-specific double strand break at a site determined by the guide polynucleotide. A Cas enzyme can be from any appropriate species (e.g., an archaea or bacterial species). For example, a Cas enzyme can be from *Streptococcus pyogenes*, *Pseudomonas aeruginosa*, or *Escherichia coli*. In some cases, a Cas enzyme can be a type I (e.g., type IA, IB, IC, ID, IE, or IF), type II (e.g., IIA, IIB, or IIC), or type III (e.g., IIIA or IIIB) Cas enzyme. The encoded Cas enzyme can be any appropriate homolog or Cas fragment in which the enzymatic function (i.e., the ability to introduce a sequence-specific strand breaks in a double helical nucleic acid sequence) is retained. In some cases, a Cas enzyme can be codon optimized for expression in particular cells, such as dicot or monocot plant cells. See, for example, the CRISPR/Cas profiles database available on the National Center for Biotechnology Information website (available at ncbi.nih.gov/pub/wolf/_suppl/CRISPRclass/crispr-Pro.html). In some embodiments, a Cas gene is from *Streptococcus pyogenes*. Examples of Cas genes that can be used as described herein include, without limitation, Cas3, Cas4, Cas6, Cas8a, Cas8b, Cas8c, Cas9, Cas10, Cas10d, Cmr5, Cpf1 (Zetsche et al., 2015 "Cpf1 Is a Single RNA Guided Endonuclease of a Class 2 CRISPR-Cas System" Cell 163, 759-771), Cse1, Csm2, Csn2, and Csy1 genes. In some embodiments, a Cas gene is a *Streptococcus pyogenes* Cas9 gene (SEQ ID NO: 1).

Any appropriate CRISPR/Cas system can be used as described herein. Examples of CRISPR/Cas systems that can used as described herein include, without limitation, those are described elsewhere (e.g. U.S. Pat. Nos. 8,697,359; 8,771,945; 8,795,965; 8,865,406; 10 8,871,445; 8,889,356; 8,889,418; 8,895,308; 8,906,616; 8,932,814; 8,945,839; 8,993,233; 8,999,641; 9,115,348; U.S. Pat. App. Pub. Nos. 2011/0223638; 2014/0068797; 2014/0302563; 2014/0315985; 2015/0152398; 2015/0284697; and Schaeffer et al. 2015 *Plant Sci.* 240:130-42).

Additional features that can be used to control and/or enhance the CRISPR/Cas system include, for example, protospacer adjacent motifs, spacers (e.g., target spacers), and termination signals (see, e.g., Mali et al., 2013 *Science* 339:823-826). A gRNA-expressing transgene can include a protospacer adjacent motif (PAM) sequence. Without being bound by theory, it is believed that PAMs to be important for type I (e.g., type IA, IB, IC, ID, IE, or IF) and type II (e.g., IIA, IIB, or IIC) CRISPR-Cas systems, but are not necessary in type III (e.g., IIIA or IIIB) CRISPR-Cas systems. For example, it is believed that a type I or type II Cas enzyme will recognize and cleave a gene sequence having a PAM sequence at the 3'-end. A PAM sequence can be on a coding strand or a noncoding strand of a target gene. A PAM sequence on a coding strand can be, for example, 5'-NGG-3' where N is any nucleotide followed by two guanine (G) nucleotides or 5'-NGA-3' where N is any nucleotide followed by a guanine (G) residue and an adenine (A) residue. A PAM sequence on a non-coding strand can be, for example, 5'-CCN-3' where N is any nucleotide following two cysteine (C) residues. A nucleic acid molecule having a gRNA expressing transgene as described herein can also include at least one target spacer. Thus, a target spacer corresponding to a sequence upstream of a PAM can be used to ensure binding of a gRNA to a target site within a gene and enable Cas enzyme activity at a nearby cleavage site within the gene.

Transgenic Plants and Methods of Making Transgenic Plants

In some embodiments this document relates to transgenic plants having at least one nucleic acid molecule described herein (e.g., having a promoter operably linked to at least one sequence to be transcribed). As used herein, a transgenic "plant" can constitute part or all of a whole plant. For example, a plant can include plant cells, explants, seed, plants grown from said seed, and grain having at least one nucleic acid molecule described herein. A transgenic plant also refers to progeny of an initial transgenic plant provided the progeny inherits a nucleic acid molecule described herein.

Transgenic Plants

A transgenic plant provided herein can be a parent plant including a nucleic acid molecule having a first promoter operably linked to at least one transgene. A parent plant can include any combination of promoters and transgenes described herein. For example, a first parent plant provided herein can include a first nucleic acid molecule having a first promoter operably linked to a first sequence, a second parent plant provided herein can include a second nucleic acid molecule having a second promoter operably linked to a second sequence, and so on. Preferably, expression of a first or a second transgene in a parent plant does not cause any phenotype in a parent plant. As such, a parent plant can be chosen based on the absence of any phenotype resulting from expression of the transgene. A first parent plant can include a first nucleic acid molecule as described herein. For example, a first parent plant can include a first nucleic acid molecule having a first promoter operably linked to at least one first transgene. The first promoter can be a ubiquitous promoter (e.g. a Pol III promoter). The first transgene can be a gRNA-expressing transgene.

A second parent plant can include a second nucleic acid molecule as described herein. For example, a second parent plant can include a second nucleic acid molecule having a second promoter operably linked to a second transgene. The second promoter can be a regulated promoter (e.g., a tissue-specific promoter or a developmentally-specific promoter), or a ubiquitously expressing promoter. The second transgene can be a Cas-expressing transgene. In some embodiments, a second parent plant can include a second nucleic acid molecule having a developmentally-specific floral meristem Zm Zap 1 promoter (SEQ ID NO: 5) operably linked to at least one Cas9-encoding sequence (SEQ ID NO: 1). Expression of at least one Cas9-e encoding sequence in, for example, the floral meristems of the second parent plant may produce germline cells harboring different mutations, and thus a single plant can give rise to progeny with different mutations in the same genomic target. But in general, mutations can be kept in germ cells by Cas and gRNA co-expression in cellular progenitors, thus ensuring that the mutations become heritable. Accordingly, co-expression of the gRNA-expressing transgene and a Cas expressing transgene can be designed to occur so as to edit the cells of the gametophytes, the generative or sperms cells in the pollen, or the megaspore mother cell or the egg cell in the embryo sac, or the zygote.

A transgenic plant can also be a progeny resulting from a cross between a first parent plant and parent plant as described herein. Progeny include descendants of a particular plant or plant line. Progeny of an instant plant include seed formed on F1, F2, F3, and subsequent generation plants, seeds formed on BC1, BC2, BC3, and subsequent generation plants, or seeds formed on F1BC1, F1BC2, F1BC3, and subsequent generation plants. Seed produced by a transgenic plant can be grown and then selfed (or out-crossed and selfed) to obtain seed homozygous for a mutation or transgene of interest. Progeny can include transgenic seed produced by crossing a first parent plant and second parent plant as described herein as well as transgenic plants grown from those transgenic seed.

Methods for Making Transgenic Plants

Nucleic acid molecules as described herein can be introduced into a plant or plant cell by any appropriate means in order to establish a transgenic plant. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be used in the methods described herein.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass composition-modulating polypeptide whose expression has not previously been confirmed in particular recipient cells.

Techniques for introducing nucleic acid molecules into monocotyledonous and dicotyledonous plants are known in the art, and include, without limitation, *Agrobacterium* mediated transformation, viral vector-mediated transformation, electroporation and particle gun transformation, e.g., U.S. Pat. Nos. 5,538,880; 5,204,253; 5,591,616; 6,013,863; and 6,329,571. If a cell or tissue culture is used as the recipient tissue for transformation, plants can be regenerated from transformed cultures by techniques known to those skilled in the art.

Growing Transgenic Plants

Transgenic plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

It is often convenient to maintain Cas transgenes and gRNA transgenes in different parents, and then produce mutations by crossing the parents to obtain mutated seeds. gRNA-expressing transgenes can be stacked as needed. Then, crosses to the Cas transgene parents result in mutated progeny.

Mutations by Transient Transfection

In some embodiments the methods can be practiced at least in part without transgene expression. Accordingly, tissue culture materials such as protoplasts can be transfected with pre-assembled ribonucloeoproteins complexes of purified Cas and gRNA (see Woo et al., Nature Biotechnology 2015, 33: 1162-1165). Plants regenerated from tissue culture often comprise the intended mutations. gRNAs can be mixed in different combinations before transfection to produce candidates that combine the designed mutations as desirable. This technique can be especially useful in species where sexual crossing is difficult or impossible, as for *Miscanthus×giganteus* or *Saccharum officianarum*. pre-assembled gRNA-Cas9 ribonucloeoproteins.

Species

The methods described herein can be applied to organisms capable of genetic modification and sexual recombination. For example, the methods described herein can be applied to plants (e.g., plant species of importance to agriculture), fungi (e.g., yeast), protozoans, and animals (e.g., fish such as salmon or zebra fish, fruit flies, or earthworms). In some cases, the methods described herein can be applied to monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

For example, suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*. In some embodiments, suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* (triticum—wheat×rye) or bamboo.

Additional examples of suitable species include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum*, or hybrids thereof (e.g., *Pennisetum purpureum×Pennisetum typhoidum*).

In some embodiments, a suitable species can be a wild, weedy, or cultivated *Miscanthus* species and/or variety such as, but not limited to, *Miscanthus×giganteus, Miscanthus sinensis, Miscanthus×ogiformis, Miscanthus floridulus, Miscanthus transmorrisonensis, Miscanthus oligostachyus, Miscanthus nepalensis, Miscanthus sacchariflorus, Miscanthus×giganteus* 'Amuri', *Miscanthus×giganteus* 'Nagara', *Miscanthus×giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern Osten', *Miscanthus sinensis* var. *gracillimus, Miscanthus sinensis* var. *variegates, Miscanthus sinensis* var. *purpurascens, Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower' (U.S. Patent No. PP14,743), *Miscanthus* var. 'Gold Bar' (U.S. Patent No. PP15,193), *Miscanthus* var. 'Gracillimus', *Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Patent No. PP13,008), *Miscanthus* var. 'Lottum', *Miscanthus* var. 'Malepartus', *Miscanthus* var. 'Morning Light', *Miscanthus* var. 'Mysterious Maiden' (U.S. Patent No. PP16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen' (aka 'Little Dot'), *Miscanthus* var. 'Rigoletto', *Miscanthus* var. 'Sarabande', *Miscanthus* var. 'Silberpfeil' (aka. Silver Arrow), *Miscanthus* var. 'Silverstripe', *Miscanthus* var. 'Super Stripe' (U.S. Patent No. PP18,161), *Miscanthus* var. 'Strictus', or *Miscanthus* var. 'Zebrinus'.

In some embodiments, a suitable species can be a wild, weedy, or cultivated *sorghum* species and/or variety such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum×almum, Sorghum×sudangrass* or *Sorghum×drummondii*.

Thus, the methods described herein can be applied to a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the methods described herein can be applied to hybrids of different species or varieties of a specific species (e.g., *Saccharum* sp.×*Miscanthus* sp., *Sorghum* sp.×*Miscanthus* sp., e.g., *Panicum virgatum*×*Panicum amarum, Panicum virgatum*×*Panicum amarulum*, and *Pennisetum purpureum*×*Pennisetum typhoidum*).

An elite plant line or elite plant variety can be an agronomically superior plant line that has resulted from many cycles of breeding and selection for superior agronomic performance. Generally, an elite variety is a collection of plants that has been selected for a particular characteristic or combination of characteristics or traits, uniform and stable in those characteristics, and when propagated by appropriate means, retains those characteristics. An elite variety may have a high uniformity level at least with respect to specific genomic regions. For example, at least 90% of the individuals of an elite variety may exhibit a specific genotypic profile, as it may be detected and characterized with the respective molecular markers. Numerous elite plant lines are available and known to those of skill in the art of breeding for any cultivated plants. Traits that may be considered to confer elitism include, without limitation, good lodging resistance, reduced bacterial infection susceptibility, good seed set, good pollen set, good roots, good cold germination, good combining ability, tolerance to pests, tolerance to disease, tolerance to drought, tolerance to salts or metals, uniform floral timing, good fertilizer use efficiency, high yield as an inbred, high yield as a hybrid, good plant height, and optionally herbicide resistance or tolerance. In some cases, an elite line or elite cultivar might not itself exhibit such traits, but rather it is considered elite because it exhibits the ability to serve as one parent of an elite hybrid.

Crossing

In some aspects, the methods described herein are based in part on segregation of heterozygous mutations in sexual crossing. The recombination step often involves crossing of two different plants, i.e., male and female, rather than self-fertilization of self-compatible plants. Typically, hybrids can be produced by preventing self-pollination of female parent plants (i.e., seed parents), and permitting pollen from male parent plants to fertilize female parent plant, and allowing F1 hybrid seeds to form on the female plants. Self-pollination of female plants can be prevented by physically emasculating the flowers at an early stage of flower development. Alternatively, pollen formation can be prevented on the female parent plants using a form of male sterility. For example, male sterility can be cytoplasmic male sterility (CMS), nuclear male sterility, genetic male sterility such as temperature or photoperiod-sensitive genetic male sterility, molecular male sterility wherein a transgene or mutation inhibits microsporogenesis and/or pollen formation, or be produced by self-incompatibility. Female parent plants containing CMS are particularly useful. Some crop species such as corn, *sorghum*, canola, and rice have well known hybridization systems based on cytoplasmic male sterility (CMS). In embodiments in which the female parent plants are CMS, the male parent plants typically contain a fertility restorer gene to ensure that the F1 hybrids are fertile.

The parent plants can be grown as substantially homogeneous adjoining populations to facilitate natural cross-pollination from the male parent plants to the female parent plants. The F1 seed formed on the female parent plants can be selectively harvested by conventional means. One also can grow the two parent plants in bulk and harvest a blend of F1 hybrid seed formed on the female parent and seed formed upon the male parent as the result of self-pollination.

A hybridization system based on a two component design also can be adopted in species where CMS or physical emasculation options are not widely available. Accordingly, a line could be developed that is homozygous for a target transgene coding for the cytotoxic barnase sequence. A different line has an activator transgene with a DNA binding domain complementary to upstream activating sequence of the barnase target and a transcription activating domain capable of driving tanscription, and driven by an anther specific promoter. The two lines are crossed to produce the female for the cross needed to produce the testing population. The male plant for the cross which produces the testing population, on the other hand, is homozygous for a barnase-inactivating barstar sequence. The barstar transgene could be either a target transgene for a two component system, possibly with the same UAS as the barnase transgene, or could be a direct fusion gene. Of course, other transgenes or mutations would also be present in the male and female progenitors of the testing population. Alternatively, similarly to the canola MS8/RF3 hybridization system, male sterility can be achieved with a barnase sequence driven by a tapetum-specific promoter (Mariani et al., Nature 357, 384-387, 1992), which can be used in conjunction with a linked herbicide tolerance gene for female propagation. Fertility can be restored when needed by crossing with a plant having a construct directing expression of barstar sequence in the same cells as the barnase. Suitable promoters may be found in the literature, including Kato et al., 2010 Plant Mol. Biol. Rep 28: 381-387, Luo et al., 2006 Plant Mol. Biol 62(3): 397-408, Gupta et al., 2007 Plant Cell Rep. 26(11): 1919-31, Liu et al., 2013 Planta 238(5): 845-57, and Goldberg et al., 1993 Plant Cell 5: 1217-1229.

Nevertheless, self-fertilization of a self-compatible species is also feasible to carry out the methods provided herein. Selfing of a plant with heterozygous mutations can provide by meiotic recombination needed for a testing population. Selfing of heterozygous materials may also be performed at an earlier or intermediate step of providing a testing population to produce plants with a genetic composition of heterozygous and/or homozygous mutations that may be desirable for phenotyping, producing, or propagating.

Testing Populations

A population of individuals having different combinations of mutations needs to be made, and then phenotyped. There are many ways of making a suitable testing population.

In many cases, a Cas-expressing transgene is present in one parent of a cross, and gRNA-expressing transgenes are present in the other parent. It is often desirable for the Cas-expressing transgene to be homozygous in the parent, so the entire population formed by the cross accumulates mutations. The gRNA transgenes can also be homozygous in the parent, although all or some gRNA-expressing transgenes may also be heterozygous in certain experimental designs. The heterozygous transgenes will segregate in the progeny, and thus contribute to a population comprising individuals with either wild type or mutated genomic targets.

If the Cas transgene is expressed early in development, the progeny of the very first cross between a Cas-expressing transgene parent and a gRNAs-expressing parent could itself be a testing population. This is because relatively uniform genotypes are produced throughout the tissues of such individuals, so the phenotypes observed in this population are likely to be heritable. The individuals of the population will have different sets of mutations caused by the random NHEJ repair mechanism.

In most cases, it is desirable to produce a testing population that recombines mutations first generated in progenitor individuals. One reason for this is to "shuffle" the mutations and thus increase the diversity of the testing population, thus increasing the chances of seeing phenotypes caused by specific pairs or combinations of mutations. Also, especially if a high numbers of genomic targets are addressed, it is desirable to have a testing population with individuals comprising mutations only in different subsets of genomic targets. Another reason for producing testing populations by crossing individuals with the original germline mutations is to segregate transgenes away from the testing population. A Cas-expressing transgene may be problematic if present in certain testing populations as it may produce new unintended mutations.

In most embodiments, the testing population contains mutations recombined by meiotic segregation. Thus one or both parents have at least a subset of the mutations of interest in a heterozygous state, and they give rise to progeny, i.e. a testing population, with the expected recombination of mutations. In some embodiments, each mutation in a heterozygous state will segregate during meiosis, forming gametes either containing or free of the mutation. This meiotic segregation is used in the methods provided herein, so that parental plants carrying many mutations of interest generate progeny with many different combinations of the parental mutations.

The genetic background of a testing population is in many embodiments as homogenous as possible, so as to have as little individual to individual variation as possible, as this variation would interfere with the phenotype to be scored that is attributable to individual mutation combinations. Thus, transgenes may first be introgressed, if needed, in near isogenic lines, and then the various crosses could be planned to form the testing population. A testing population, however, is often the F1 seed of parents of complementary heterotic groups, as understanding the effect of mutations within the heterotic background of a commercially relevant hybrid is desirable. Either or both parent may comprise mutations, and the mutations may be made by gRNAs that are completely identical between the parents or progenitors of the parents, completely different, partly overlapping, or with at least a subset of the initial gRNAs directed to different residues of the same genomic targets.

There are many types of crosses that can produce testing populations. In many cases, forming heterozygous individuals by crossing individuals having germline mutations to wild type is appropriate. It is desirable, however, to have a testing population with individuals homozygous for at least some mutations so as to produce phenotypes of recessive alleles. Consequently, selfing or sibling crossing is needed, or, if heterosis needs to be maintained, mutations can be generated independently or introgressed into complementary genetic backgrounds.

There are many ways in which parental plants having heterozygous mutations of interest can be obtained. For example, for self-compatible species, it is easy to make by selfing and selection a parent stock that is homozygous for the mutations of interest. Heterozygous mutations will then result by crossing homozygous plants with a plant null for the respective mutations. For self-incompatible species, fixing homozygous mutations in a propagating population is also feasible, and molecular characterization of individual progenitors would be especially helpful. Creating double haploids can also be useful, if feasible for a particular species, when needed to obtain plants homozygous for desired mutations.

In some embodiments testing populations are made by crossing parents with heterogeneous mutant makeup. Crosses may be made randomly starting with parents of diverse but known mutation mixture composition. As long as pollination occurs randomly, the genetic structure of the progeny or testing population can be inferred from the distribution of mutations in the parents. This approach may be convenient in certain cases, such as when working with obligate outcrossing species or with populations of improvement rounds.

In some embodiments, the parent plants also can be homozygous for one or more mutations. In some embodiments, the parent plants are heterozygous at loci of interest, with both alleles mutated from the genomic target wild type.

In some embodiments, mutations may be present in both the male and female parents of the cross that makes the testing population. In other embodiments, all the heterozygous mutations may be present in a single parent. This approach is desirable when transformation of one parent is comparatively easy, so that introgression of mutations into a parent of a different genetic background is not necessary.

Phenotyping

Populations of progeny plants can be screened and/or selected for those members of the population that have a trait or phenotype, or a combination of traits or phenotypes conferred by the particular combinations of mutations that is distinguishable from control plants. A control plant refers to a plant that does not contain one or more of the mutations in a plant of interest, but otherwise has the same or similar genetic background. A suitable control plant can be a non-mutant wild type plant, a non-mutant and optionally non-transgenic segregant from a mutagenesis experiment, a plant that contains one or more mutations other than the one or more mutations of interest, or a plant that contains a subset of mutations. Phenotyping can be performed in a greenhouse and/or laboratory and/or in the field. In some embodiments, a population of plants can be selected that has improved heterosis, grain yield, tolerance to abiotic stress such as drought stress, osmotic stress, or nitrogen deficiency, soil aluminum, cold stress, frost stress, density stress, heat stress, oxidative stress, low light tolerance, herbicide stress, as well as improved water use efficiency, nitrogen use efficiency, phosphate use efficiency, seed oil or protein content, lignin content, biotic or pest resistance, biomass, chemical composition, plant architecture, flowering time, and/or biofuel conversion properties. In some cases, selection and/or screening can be carried out over multiple rounds of mutagenesis. Selection and/or screening can be carried out over one or more generations, and/or in more than one geographic location. In some cases, mutant plants can be grown and selected under conditions which induce a desired phenotype or are otherwise necessary to produce a desired phenotype in a mutant plant. In addition, selection and/or screening can be applied during a particular developmental stage in which the phenotype is expected to be exhibited by the plant. But, in many cases a phenotypic measure is yield of harvestable material under typical field cultivation conditions, i.e. without an intentionally applied selection pressure. Selection and/or screening can be carried out to choose those mutant plants having a statistically significant difference in yield (e.g., grain, vegetative biomass, or stem sucrose yield) relative to a control plant that lacks the combination of mutations. Selection and/or screening can be carried out to choose those mutant plants having a statistically significant difference in an abiotic stress tolerance level relative to a control plant that lacks the transgene. While the focus is most often on individuals with mutation combinations exhibiting improved performance, it is sometimes useful to identify stacks of significantly impaired performance over a control. Identification of undesirable mutations can be useful in designing subsequent improvement rounds so as to eliminate or minimize their occurrence.

To test for density stress tolerance, the testing population can be planted at an excessive density for the respective genetic background controls, and yield of individual plants scored for identifying the best performing individuals (see, for example, Mansfield and Humm, 2014, Crop Science, 57:157-173).

A heterotic group comprises a set of genotypes that perform well when crossed with genotypes from a different or complementary heterotic group. Inbred lines are classified into heterotic groups, and are further subdivided into families within a heterotic group, based on several criteria such as pedigree, molecular marker-based associations, and performance in hybrid combinations (see e.g. Smith at al. (1990) Theor. Appl. Gen. 80:833-840). For example for corn, the two most widely used heterotic groups in the United States are referred to as "Iowa Stiff Stalk Synthetic" (BSSS) and "Lancaster" or "Lancaster Sure Crop" (sometimes referred to as NSS, or iron-Stiff Stalk).

To test for nitrogen use efficiency, seeds of a testing population can be planted in a field using standard agronomic practices for the region, along with wild type controls of the same genetic background. Fertilizer is applied at about 50% of the optimal level for the respective location, so that yield of wild type plants is negatively impacted. See, Example 3.

Aside from pre-defined phenotypical observations to be made on testing populations such as those appropriate to screen for stress tolerances, the appearance of nearby planted negative controls can be useful in comparing to individuals in the testing population for observation of phenotypic differences that may be caused by some mutation combinations. Non-limiting examples of traits to be observed for example in corn include ear diameter, ear height, ear leaf length, ear leaf weight, ear length, ear position, ear number, grain color, kernel length, kernel number, kernel row arrangement, kernel row number, kernel type, kernel width, leaf length, leaf width, tassel size, tassel type, and uppermost ear shape, and others traits described, for example, in the Maize Traits for Fieldbooks. See the world wide web at "cril.cimmyt.org/confluence/display/MBP/Activity+2.1.2+-+Maize+Traits+for+Fieldbooks."

The methods provided can be used to generate a very large number of different combinations of mutations. But very large numbers can also have drawbacks, so in designing combinations it is often desirable to limit the number of combinations. A limit can sometimes be imposed by the need to replicate individual genotypes so to understand the statistical significance of the phenotypes observed, and as such this limit is correlated with the size of any designed study. But, a limited "unit" of related variability is also helpful in side-by-side comparisons. For example, a single parent having four gRNAs can generate two different mutations in each allele of the four genomic targets. If first crossed to the wild type and the progeny then selfed, the mutations can form 1296 different combinations in homozygous and heterozygous states. Planting a population with having no more than this variability on a contiguous and identifiable plot helps by minimizing the environmental variability exposure and allowing for manageable comparative phenotyping. In other words, when related genotypes are replicated in a defined area, individuals can be readily examined for visually noticeable differences. As such, it is desirable to design variability units that occupy generally no more than about half a hectare or about one acre. For example, 1296 corn genotypes replicated 10-fold, i.e. about 13,000 plants, are typically planted on about one acre.

When seeking to first sort through the candidate mutations, it is preferable to make and phenotype a population of plants of a uniform genetic background if possible. However, a reduced number of candidates can be tested in variable genetic backgrounds. When the tested populations are sufficiently large, the interaction of different mutation combinations with known QTLs can thus be determined. Consequently, the methods provided herein can be used in conjunction with traditional breeding selections to produce cultivars with improved traits.

Genotyping

As described herein, plants that are identified as having an improved phenotypic feature can be genotyped using any methodology. Genotyping will often involve sequencing of the genomic target of the mutated materials of interest, i.e. at least around the residues targeted by gRNA used in mutagenesis, to determine the precise mutation introduced in specific individuals. Genotype refers to the combination of mutations present in an individual plant, which can be determined by a variety of methods known in the art, such as PCR with genomic target-specific primers or Southern blotting. Genotype can also refer to the combination of alleles that determines a characteristic or trait, and it can be indirectly characterized using markers or directly characterized by nucleic acid sequencing. Suitable markers include a genetic marker, or some other type of marker. The genotype can reflect the sequence of a portion of a chromosome, an entire chromosome, a portion of the genome, or of the entire genome. In some embodiments, leaf punches from individuals either to be selected for testing or identified as having an improved phenotypic feature can be genotyped. In some embodiments, seed chipping, in which the genetics of the seed can be assessed without destroying the seed, is used to select a subset of individuals from the progeny population for use as a testing. See, for example U.S. Pat. No. 7,502,113. Accordingly, a population can be created that mixes a large number of mutations. Subsequently, as it may become desirable as informed by new performance data, a subpopulation comprising only a defined subset of mutations, and possibly lacking transgenes such as a Cas-expressing transgene, can be selected and studied. Or similarly, individuals from a large population can be eliminated from a study by genotyping plants before planting if they are deemed to contain mutation combinations that are undesirable.

Improvement Rounds

Once a combination of mutations is identified by any means as having a desirable phenotypic performance, the improved materials can be subjected to additional rounds of improvement by adapting the methods used to identify the combination. In one type of improvement, the desired mutations are maintained in the background of all the plants of a testing population, and additional mutations combinations are also stacked. Mutation combinations can be maintained in the genetic background by making a testing population using individuals related by lineage to individuals of selected phenotypes. Alternatively, the combined genomic targets identified can be maintained as subject of de novo mutation in new testing populations, which may generate additional pairs or combinations of mutations of interest. Some of the additional mutations can be second site mutations in the same genomic targets that are part of the originally identified combination of mutations.

In some embodiments, improvements may be made using the top performing materials from a phenotyped population. For example, the best individuals can be crossed to each other and their progeny phenotyped. When the diversity of original mutations is large, this approach may more quickly result in recognition of improved combinations. This approach works well when the testing population is made up of inbred lines or uniform true breeding populations. When the testing population is made up of hybrid plants, it is possible to make one or more corresponding populations by crosses to isogenic parents so as to cause similar mutation segregation as in the hybrid testing population.

The improvement rounds can be cycled as many times as needed to develop mutation combinations of incrementally enhanced performance in the respective assays or field conditions.

The invention will be further described in the following examples, which do not limit the scope of the invention described in the claims.

EXAMPLES

Example 1: Selecting Salt Tolerance Targets

To rice make plants with enhanced salt tolerance, genomic targets comprising SEQ ID NOs: 6-10 are selected. Mutations of these targets are expected to impact the soil salt sensitivity of mutant plants. Pairs or combinations of mutations in these targets are therefore likely to produce a higher resistance to salt phenotype.

Example 2: RNA Targeting

SEQ ID NOs: 11-20 (which include the PAM 5'NGG3' for the *Streptococcus pyogenes* Cas9) can serve as RNA targeting sequences for different residues of the genomic target represented by SEQ ID NO: 6.

Example 3: gRNA-Expressing Transgenes

A transformation vector comprising gRNAs expressing genes is made. The vector comprises five tandem expression cassettes, each made up of the promoter of SEQ ID NO: 3 operably linked to a gRNA sequence made up of a RNA targeting sequence of fused to a scaffolding sequence, and followed 3' by a Pol III terminator. The five expression cassettes of this vector have the target RNAs of SEQ ID Nos: 20-24 (which include the PAM 5'NGG3' for the *Streptococcus pyogenes* Cas9), designed to mutate genomic targets comprising SEQ ID NOs: 6-10. The vectors are used in *Agrobacterium*-mediated transformation of rice.

Example 4: Selecting Corn Ear Morphology Targets

To make corn plants with enhanced grain yield, genomic targets comprising SEQ ID NOs: 26-39 are selected. Mutations of these targets are expected to impact the ear morphology of mutant plants. Pairs or combinations of mutations in these targets are therefore likely to produce corn cobs with higher grain yield.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a combination of genetic mutations that improves a phenotype of a plant, wherein said method comprises:

(a) selecting a plurality of genomic targets for mutation, wherein said plurality of genomic targets comprises at least one of SEQ ID NOs: 26-39, (b) making a plant cell comprising a plurality of different gRNAs designed to mutate the genomic targets and a Cas9 polypeptide, wherein a plant descended from the plant cell has a plurality of germline mutations, (c) sexually crossing a first parental plant comprising at least a subset of the germline mutations to a second parental plant to produce a progeny population, (d) phenotyping the progeny population to select an individual with improved phenotype, and (e) genotyping the selected individual to identify the combination of genetic mutations that improves the phenotype of the plant.

2. The method of claim 1, wherein said plurality of genomic targets comprises at least four of SEQ ID NOs: 26-39.

3. The method of claim 1, wherein said first and second parental plants are *Zea mays*.

4. The method of claim 1, wherein a subset of said plurality of different gRNAs are designed to mutate distinct residues of the same genomic target.

5. The method of claim 1, wherein a subset of said plurality of different gRNAs is designed to mutate residues within conserved sequences of paralogous genes.

6. The method of claim 1, wherein making a plant cell comprises inserting gRNA-expressing transgenes.

7. The method of claim 1, wherein making a plant cell comprises contacting the cell with pre-assembled gRNA-Cas9 ribonucloeoproteins.

8. The method of claim 1, wherein making a plant cell comprises adding a Cas9 polypeptide-expressing transgene.

9. The method of claim 8, wherein adding the Cas9 polypeptide-expressing transgene comprises crossing to a plant having the Cas9 polypeptide-expressing transgene.

10. The method of claim 8, wherein the first parental plant is a progeny of selfing the plant having the germline mutations.

11. The method of claim 8, wherein the first parental plant is a progeny of a cross of the plant having germline mutations to a wild type plant.

12. The method of claim 8, wherein the first parental plant is a progeny of a cross of the plant having mutated germline to another plant, whereby the germline mutations of the first parental plant are heterozygous.

13. The method of claim 8, wherein the first parental plant does not comprise the Cas9 polypeptide-expressing transgene.

14. The method of claim 1, wherein the second plant has germline mutations.

15. The method of claim 1, wherein said first and second parental plants are isogenic and belong to complementary heterotic groups.

16. The method of claim 1, wherein said method comprises repeating steps (a) through (e), wherein said selecting of step (a) comprises genomic targets determined to be present within said selected individual in step (d).

17. The method of claim 1, wherein said method comprises repeating steps (a) through (e), wherein said first or said second parental plants are related by lineage to an individual selected in step (d).

18. A method for making a collection of seeds, wherein the embryonic cells of said seeds comprise a combination of genetic mutations identified by the method of claim 1.

19. The method of claim 1, wherein said first parental plant and said second parental plant are selected from the group consisting of *Zea mays, Sorghum bicolor, Triticum aestivum,* and *Oryza sativa*.

20. The method of claim 1, wherein said first parental plant or said second parental plant is cytoplasmically male sterile.

21. The method of claim 1, wherein said selecting of step (d) is based at least in part on performance under field testing conditions.

22. The method of claim 1, wherein said selecting of step (d) is based at least in part on water use efficiency, nitrogen use efficiency, seed oil content, or plant density stress performance.

23. The method of a claim 1, wherein phenotyping said progeny comprises using seed chipping to select a subset of individuals from said progeny population.

* * * * *